United States Patent [19]
Fujita et al.

[11] Patent Number: 6,017,467
[45] Date of Patent: Jan. 25, 2000

[54] PROPIOLONITRILE DERIVATIVES AND LIQUID CRYSTAL COMPOSITIONS COMPRISING THE SAME

[75] Inventors: Atsuko Fujita, Chiba; Shuichi Matsui, Ichihara; Hiroyuki Takeuchi, Ichihara; Kazutoshi Miyazawa, Ichihara; Norio Tamura, Ichihara; Norihisa Hachiya, Yashio; Etsuo Nakagawa, Ichihara, all of Japan

[73] Assignee: Chisso Corporation, Osaka, Japan

[21] Appl. No.: 08/874,229

[22] Filed: Jun. 13, 1997

[30] Foreign Application Priority Data

Jun. 28, 1996 [JP] Japan ................... 8-187004

[51] Int. Cl.⁷ ................ C09K 19/52; C09K 19/300; C07C 255/45; C07D 319/06
[52] U.S. Cl. ............... 252/299.01; 252/299.61; 252/299.63; 252/299.64; 252/299.65; 252/299.66; 252/299.67; 558/425; 570/127; 570/129; 544/303; 549/369
[58] Field of Search ............... 252/299.01, 299.61, 252/299.63, 299.64, 299.65, 299.66, 299.67; 558/425; 570/127, 129; 544/303; 549/369

[56] References Cited

FOREIGN PATENT DOCUMENTS

| | | |
|---|---|---|
| 40 27 458 A1 | 8/1991 | Germany . |
| 55-9012 | 1/1980 | Japan . |
| 58-110527 | 7/1983 | Japan . |
| 59-122440 | 7/1984 | Japan . |
| 59-1399353 | 8/1984 | Japan . |
| 59-176221 | 10/1984 | Japan . |
| 59-190958 | 10/1984 | Japan . |
| 60-19756 | 1/1985 | Japan . |
| 60-169455 | 9/1985 | Japan . |
| 60-188358 | 9/1985 | Japan . |
| 4-501275 | 3/1992 | Japan . |
| 4-503523 | 6/1992 | Japan . |
| 2 111 992 | 7/1983 | United Kingdom . |

OTHER PUBLICATIONS

Chemical Abstracts, vol. 102, No. 25, Jun. 24, 1985, Abstract No. 220593.
Chemical Abstracts, vol. 104, No. 18, May 5, 1986, Abstract No. 160058.
Chemical Abstracts, vol. 104, No. 14, Apr. 7, 1986, Abstract No. 120516.
Chemical Abstracts, vol. 102, No. 1, Jan. 7, 1985, Abstract No. 0059964.

*Primary Examiner*—Shean C. Wu
*Attorney, Agent, or Firm*—Oblon, Spivak, McClelland, Maier & Neustadt, P.C.

[57] ABSTRACT

A propiolonitrile derivative of formula (I)

(1)

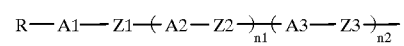

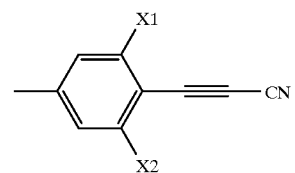

wherein n1 and n2 each independently stand for 0 or 1; A1, A2 and A3 each independently represent a 1,4-phenylene, a 1,4-phenylene substituted by one or more fluorine atoms, a trans-1,4-cyclohexylene, a 1,3-dioxane-2,5-diyl or a 1,3-pyrimidine-2,5-diyl; Z1, Z2 and Z3 each independently represent a single bond, ethylene, ethenylene, ethynylene, carbonyloxy, oxycarbonyl, methyleneoxy, oxymethylene, 1,4-butylene or 1,4-butenylene; R represents a saturated, aliphatic hydrocarbyl radical of 1–10 carbons, an unsaturated, aliphatic hydrocarbyl radical of 2–10 carbons, a saturated or unsaturated, aliphatic hydrocarbyl radical of 1–10 carbons containing one or more ether linkages (—O—) in the chain and a saturated or unsaturated, fluoro-substituted aliphatic hydrocarbyl radical of 1–10 carbons containing one or more fluorine atoms in the chain; X1 and X2 each independently represent H, F or Cl;

provided that at least one of X1 and X2 is F or Cl, when both n1 and n2 are 0, Z1 represents a single bond, ethylene, carbonyloxy or oxycarbonyl and R represents alkyl or alkoxy; or when n1 is 1, n2 is 1 or 0, Z1 and Z2 each independently represent a single bond or ethylene, Z3 represents ethylene and R represents alkyl or alkoxy.

33 Claims, No Drawings

PROPIOLONITRILE DERIVATIVES AND LIQUID CRYSTAL COMPOSITIONS COMPRISING THE SAME

FIELD OF THE INVENTION

This invention relates to a liquid crystalline compound consisting of new propiolonitrile derivatives, a liquid crystal composition comprising the same and a liquid crystal display element using said composition.

BACKGROUND OF THE INVENTION

A display element utilizing the characteristics of liquid crystal materials such as optical anisotropy and dielectric anisotropy has been extensively used in the applications including watch, calculator or the like. Liquid crystal phase includes a nematic phase, a smectic phase and a cholesteric phase. In practical use, the nematic phase is most conventional. The display modes in this case can include a twisted nematic (TN) mode, a dynamic scattering (DS) mode, a guest/host mode, a DAP (deformation of aligned phases) mode or the like. A large number of the liquid crystalline compounds used for the display modes have been developed, but there is no commercial example for a display element in which a single compound is encapsulated. It is required that liquid crystal materials for display element exhibit a liquid crystal phase over a broad temperature range centering in room temperature, have a good stability towards moisture, light, heat, air, electric fields and electromagnetic radiation under the environment in which a display element is used, and have sufficient characteristics to drive a display element.

The physical values such as optical anisotropy, dielectric anisotropy and electrical conductivity required for liquid crystal materials are dependent on mode of the display and configuration of the element. In particular, the liquid crystal materials for the STN mode which have been recently applied to the liquid crystal display of high quality level should have high elastic constant ratio (k3/k1) and dielectric anisotropy, and low viscosity to obtain good display having high steepness and quick response rate.

However, a single compound satisfying these requirements at the same time is not known yet and the liquid crystal materials used in the current display are the composition comprising a mixture of liquid crystalline compounds having each of the characteristics. If a single compound having different characteristics is mixed each other, frequency and temperature dependences are higher, which makes it difficult to obtain uniform display under each use environment. Thus, a compound having high elastic constant ratio, high dielectric anisotropy, optical anisotropy close to the predetermined constants, broad liquid crystal temperature range, high compatibility with other liquid crystals, good stability and low viscosity not injuring a response rate is an important key to obtain a display of the STN mode having very reduced frequency and temperature dependences and good characteristics.

As the liquid crystalline compounds having high elastic constant ratio, high dielectric anisotropy and relatively low viscosity, alkenyl compounds of the following formula (A) are generally known in Japanese Patent Kokai 59-176221. Those compounds are comparatively narrow in the nematic liquid crystal temperature range and so require a combined use with the compounds having high clearing points to compensate the narrow temperature range, where they are used as an ingredient of the liquid crystal composition. In general, however, the compound having high clearing point exhibits high viscosity. Therefore, an addition of the above-mentioned alkenyl compounds results in an increase in the viscosity of the total composition. Cinnamonitrile derivatives of the following formula (B) wherein R is alkyl of 1–8 carbons are also known as a liquid crystalline compound in Japanese Patent Kokai 55-9012, but they may have poor stability towards light. Further, propiolonitrile derivatives of the following formula (C) wherein R is a straight-chain alkyl of 1–9 carbons or a straight-chain alkoxy of 1–9 carbons are known in Japanese Patent Kokai 58-110527, which have broad liquid crystal range, relatively high dielectric anisotropy and elastic constant ratio, but further improvement may be desired.

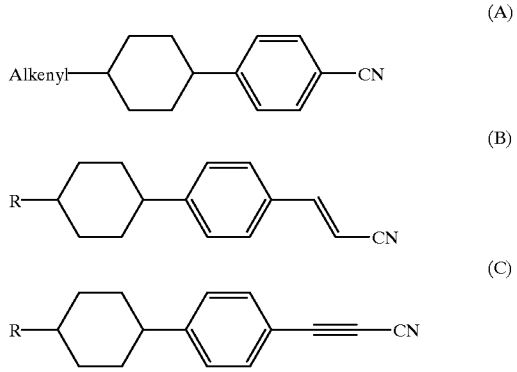

SUMMARY OF THE INVENTION

An object of the present invention is to provide a new liquid crystalline compound having excellent properties as an ingredient of a liquid crystal composition such as broad liquid crystal temperature range, high dielectric anisotropy and good compatibility with other liquid crystalline compounds, while keeping the properties of the composition such as low viscosity and being capable of providing high elastic constant ratio.

Another object of the invention is to provide a liquid crystal composition comprising the liquid crystalline compound and a liquid crystal display element using said liquid crystal composition.

We have found that a group of the compounds exhibit unique liquid crystal characteristics, by varying a combination of the six-membered rings and bridges therebetween, the substituents on the six-membered rings and the position of the substituents in the propiolonitrile derivatives of the above formula (C).

DETAILED DESCRIPTION OF THE INVENTION

The present invention provides propiolonitrile derivatives of formula (1)

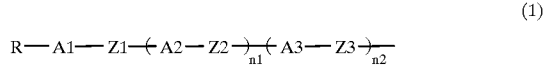

-continued

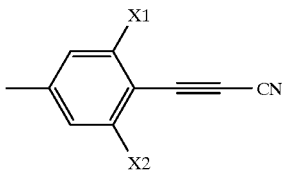

wherein n1 and n2 each independently stand for 0 or 1; A1, A2 and A3 each independently represent a 1,4-phenylene, 1,4-phenylene substituted by one or more fluorine atoms, a trans-1,4-cyclohexylene, a 1,3-dioxane-2,5-diyl or a 1,3-pyrimidine-2,5-diyl; Z1, Z2 and Z3 each independently represent a single bond, ethylene, ethenylene, ethynylene, carbonyloxy, oxycarbonyl, methyleneoxy, oxymethylene, 1,4-butylene or 1,4-butenylene; R represents a saturated, aliphatic hydrocarbyl radical of 1–10 carbons, an unsaturated, aliphatic hydrocarbyl radical of 2–10 carbons, a saturated or unsaturated, aliphatic hydrocarbyl radical of 1–10 carbons containing one or more ether linkages (—O—) in the chain and a saturated or unsaturated, fluoro-substituted aliphatic hydrocarbyl radical of 1–10 carbons containing one or more fluorine atoms in the chain; X1 and X2 each independently represent H, F or Cl;

provided that at least one of X1 and X2 is F or Cl, when both n1 and n2 are 0, Z1 represents a single bond, ethylene, carbonyloxy or oxycarbonyl and R represents alkyl or alkoxy; or when n1 is 1, n2 is 1 or 0, Z1 and Z2 each independently represent a single bond or ethylene, Z3 represents ethylene and R represents alkyl or alkoxy.

The present invention also provides liquid crystal compositions comprising at least two ingredients containing at least one of the propiolonitrile derivatives of formula (1), more specifically liquid crystal compositions comprising as a first ingredient, at least one of the propiolonitrile derivatives of formula (1) and as a second ingredient, at least one of a compound of formula (2) and/or at least one of a compound of formula (3). Further, the invention provides liquid crystal display elements composed of said liquid crystal compositions.

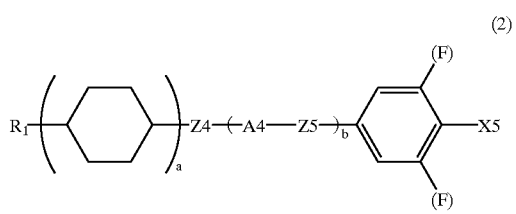

in which a is 1 or 2; b is 0 or 1; A4 represents a trans-1,4-cyclohexylene or a 1,4-phenylene which may be substituted by one or more fluorine atoms; Z4 and Z5 each independently represent a single bond, ethylene or ethenylene; $R_1$ respresents an alkyl group of 1–10 carbons and X5 represents F, $CF_3$, $OCF_3$, $OCF_2H$ or Cl; and (F) stands for the case where the phenyl ring may be substituted by F.

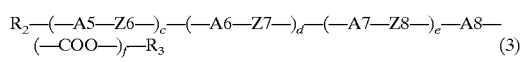

in which c, d, e and f each independently is 0 or 1; A5, A6 and A7 each independently represent a trans-1,4-cyclohexylene, a 1,4-phenylene which may be substituted by one or more fluorine atoms, a 1,3-dioxane-2,5-diyl or a 1,3-pyrimidine-2,5-diyl; A8 represents a trans-1,4-cyclohexylene or 1,4-phenylene which may be substituted by one or more fluorine atoms; Z6, Z7 and Z8 each independently represent a single bond, ethylene, ethenylene, ethynylene, 1-butene-3-ynylene or carbonyloxy; $R_2$ represents a saturated or unsaturated hydrocarbyl radical of 1 to 10 carbons optionally having one or more ether linkages (—O—) in the chain; and $R_3$ represents —CN, —F, —$OCF_3$, —$OCF_2H$, —$CF_3$, —$CF_2H$, —$CFH_2$ or a saturated or unsaturated aliphatic hydrocarbyl radical of 1 to 10 carbons optionally having one or more ether linkages in the chain.

The propiolonitrile derivatives of the present invention have excellent properties as the ingredient of a liquid crystal composition, e.g. broad liquid crystal temperature range, high dielectric anisotropy and good compatibility with other liquid crystalline compounds, while keeping the properties of the composition such as low viscosity and being capable of providing high elastic constant ratio.

In the propiolonitrile derivatives of formula (1), the terminal group R represents a saturated, aliphatic hydrocarbyl radical of 1–10 carbons; an unsaturated, aliphatic hydrocarbyl radical of 2–10 carbons; a saturated or unsaturated, aliphatic hydrocarbyl radical of 1–10 carbons containing one or more ether linkages (—O—) in the chain; and a saturated or unsaturated, fluoro-substituted aliphatic hydrocarbyl radical of 1–10 carbons containing one or more fluorine atoms in the chain.

The term "saturatred aliphatic hydrocarbyl radical" includes a straight or branched-chain alkyl group of 1–10 carbons, specific examples of which can include ethyl, methyl, n-propyl, i-propyl, n-butyl, i-butyl, t-butyl, pentyl, 2-methylbutyl, hexyl, 2-methylpentyl, 3-methylpentyl, heptyl, 2-methylhexyl, octyl, 2-ethylhexyl, 3-methylheptyl, nonyl, decyl or the like.

The term "unsaturated aliphatic hydrocarbyl radical" includes an alkynyl and alkenyl group of 1–10 carbons containing one unsaturated moiety in the straight- or branched-chain and an alkadienyl group of 1–10 carbons containing two unsaturated moieties in the chain, specific examples of which can include vinyl, allyl, 1-butenyl, 3-butenyl, 3-methyl-1-butenyl, 1-pentenyl, 3-pentenyl, 4-methyl-3-pentenyl, 3-nonenyl, ethynyl, propynyl, 1-butynyl, butadienyl, 1,5-hexadienyl or the like.

The term "saturated aliphatic hydrocarbyl radical containing one or more ether linkages (—O—) in the chain" includes a straight- or branched-chain alkoxy, alkoxyalkyl and alkoxyalkoxy groups in which the alkyl moiety has 1–10 carbons, specific examples of which can include methoxy, ethoxy, isopropoxy, butoxy, pentyloxy, hexyloxy, heptyloxy, octyloxy, 2-ethylhexyloxy, nonyloxy, decyloxy, methoxymethyl, methoxyethyl, ethoxymethyl, propoxymethyl, propoxypropyl, ethoxymethoxy, propoxyethoxy or the like.

The term "unsaturated aliphatic hydrocarbyl radical containing one or more ether linkages (—O—) in the chain" includes a straight- or branched-chain alkenyloxy, alkynyloxy and alkenyloxyalkyl groups of 1–10 carbons, specific examples of which can include allyloxy, 2-butenyloxy, pentenyloxy, propynyloxy, allyloxymethyl or the like.

The term "saturated or unsaturated, fluoro-substituted aliphatic hydrocarbyl radical" includes fluoroalkyl, fluoroalkenyl, fluoroalkoxy, fluoroalkoxyalkyl and fluoroalkenyloxy groups in which the alkyl moiety has 1–10 carbons, specific examples of which can include fluoromethyl, difluoromethyl, trifluoromethyl, fluoroethyl, difluoroethyl, trifluoroethyl, perfluoroethyl, 2,2-difluorovinyl, 4-fluoro-3-butenyl, 4,4-difluoro-3-butenyl, fluoromethoxy, difluoromethoxy, trifluoromethoxy, trifluoromethoxymethyl, 3-fluoro-1-propenyloxy or the like.

The propiolonitrile derivatives of formula (1) can be classified into a two ring system of formula (1a) wherein both n1 and n2 are 0, a three ring system of formula (1b) wherein n1 is 1 and n2 is 0 and a four ring system of formula (1c) wherein both n1 and n2 are 1.

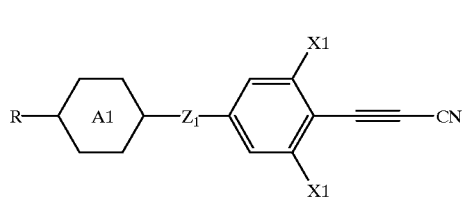
(1a)

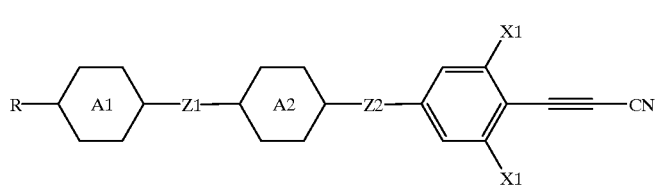
(1b)

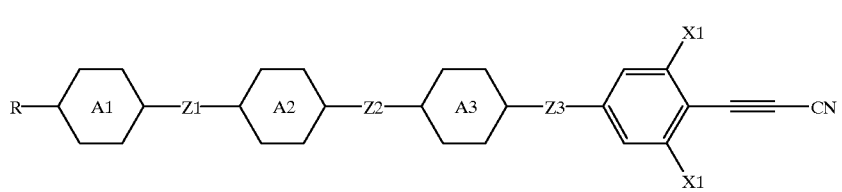
(1c)

In the above formulas, A1, A2, A3, Z1, Z2, Z3, R, X1 and X2 have the same meaning as defined above.

The two ring system compounds of formula (1a) have a liquid crystal temperature range at approximately room temperature and a lower viscosity, and also are excellent materials which are not easy to precipitate a crystal when used as an ingredient for the liquid crystal composition. The liquid crystal display using the two ring system compounds can conduct a display at more quick response rate than the case of using other cyclic compounds of larger number of six membered rings. More specific examples of the two ring system compounds are represented by the following formulas (1a-1) to (1a-28) wherein R has the same meaning as defined above, Alkyl stands for alkyl of 1–10 carbons, Alkenyl stands for alkenyl of 2–10 carbons and (F) stands for the case where the phenyl ring may be substituted by F.

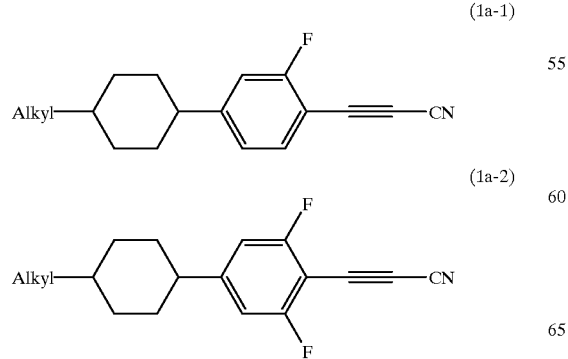
(1a-1)

(1a-2)

-continued

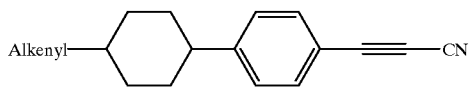
(1a-3)

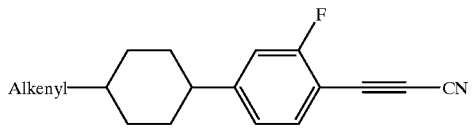
(1a-4)

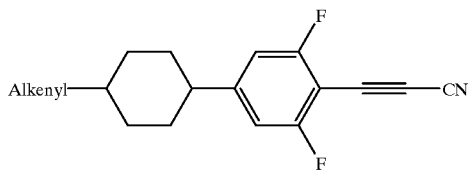
(1a-5)

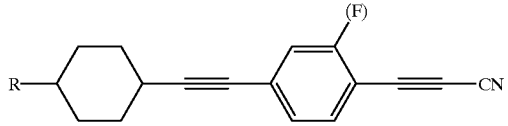
(1a-6)

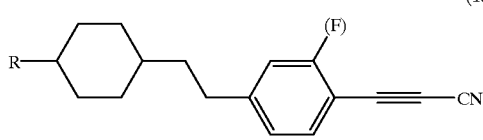
(1a-7)

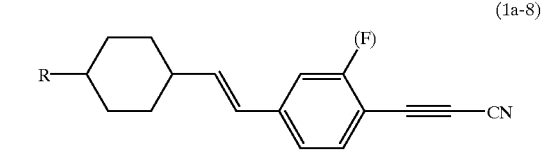
(1a-8)
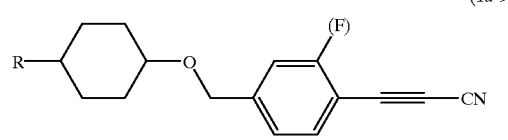
(1a-9)
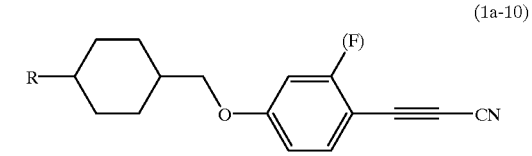
(1a-10)
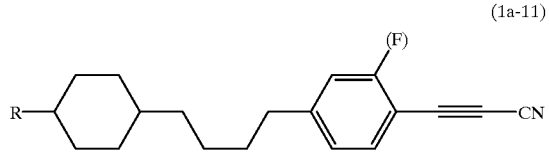
(1a-11)
(1a-12)
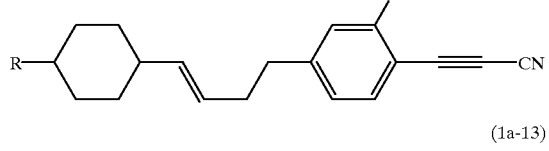
(1a-13)
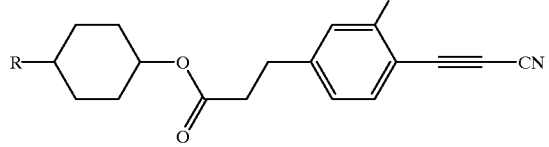
(1a-14)
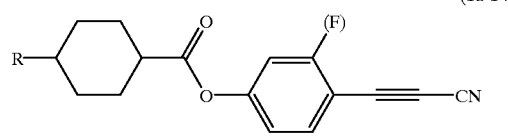
(1a-15)
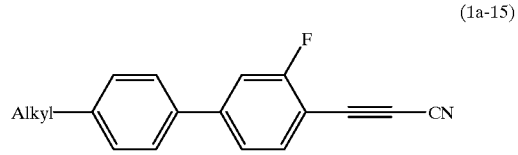
(1a-16)
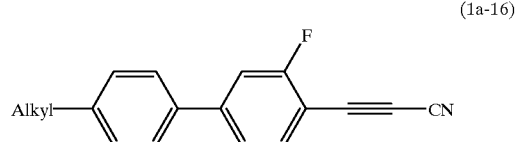
(1a-17)
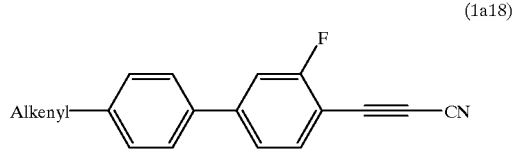
(1a-18)
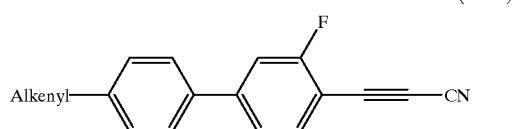
(1a-19)
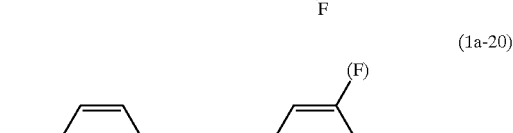
(1a-20)
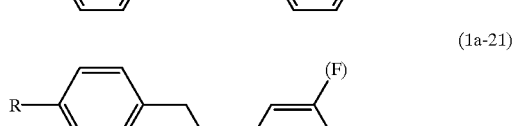
(1a-21)
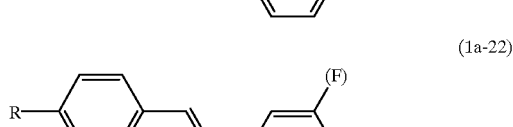
(1a-22)
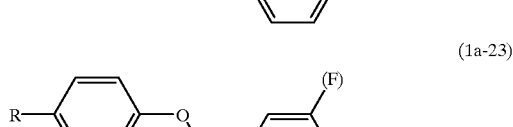
(1a-23)
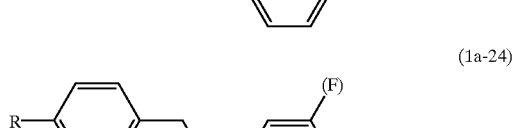
(1a-24)
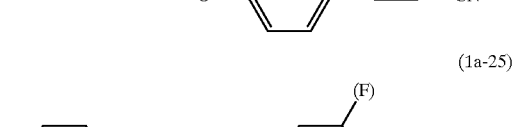
(1a-25)
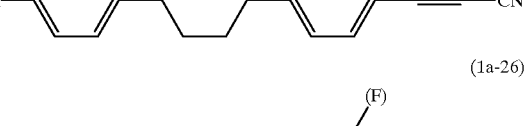
(1a-26)
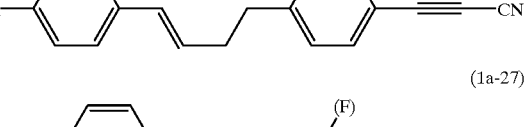
(1a-27)

(1a-28)

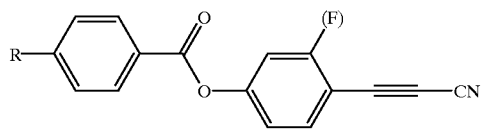

The three ring system compounds of formula (1b) have higher clearing points, good compatibility with other liquid crystalline compounds and higher elastic constant ratio required for obtaining good steepness of the liquid crystal composition.

More specific examples of the three ring system compounds are represented by the following formulas (1b-1) to (1b-81) wherein R, Alkyl, Alkenyl and (F) have the same meaning as defined above.

(1b-1)
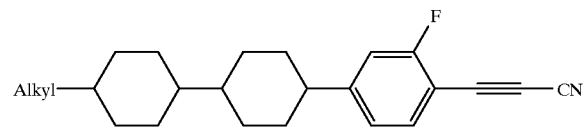

(1b-2)
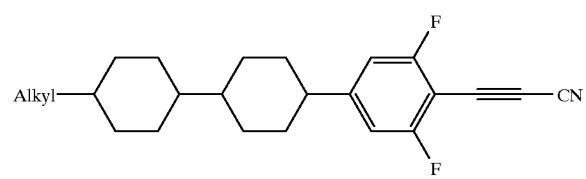

(1b-3)
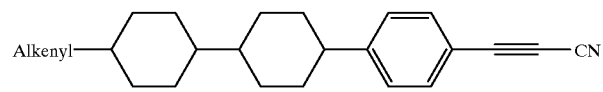

(1b-4)
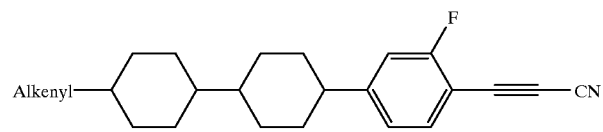

(1b-5)
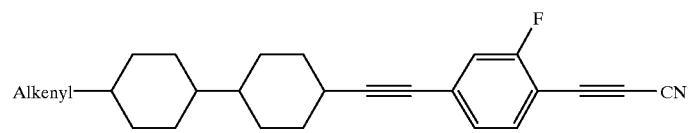

(1b-6)
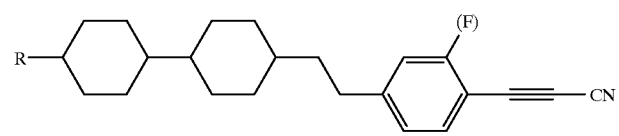

(1b-7)
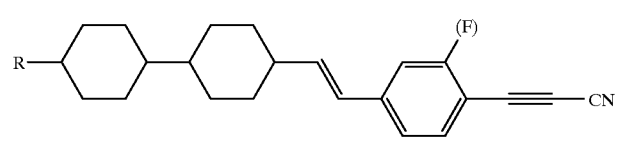

(1b-8)
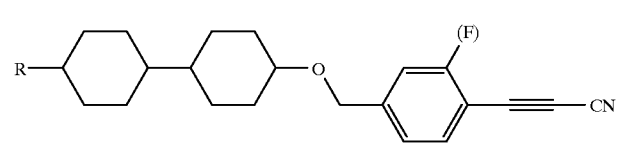

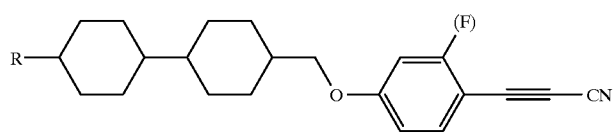
(1b-9)
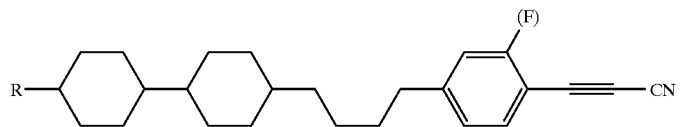
(1b-10)
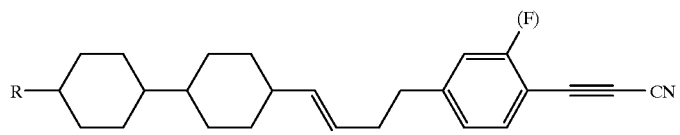
(1b-11)
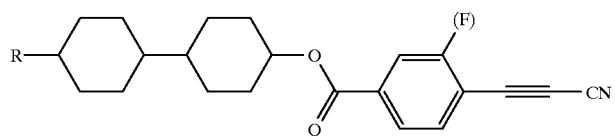
(1b-12)
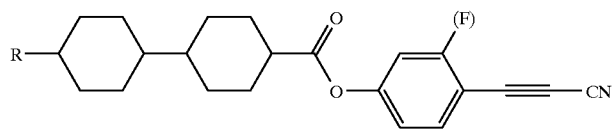
(1b-13)
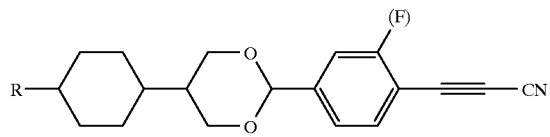
(1b-14)
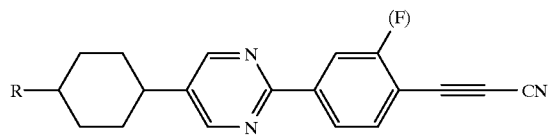
(1b-15)
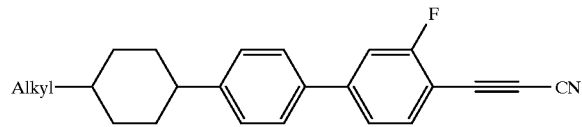
(1b-16)
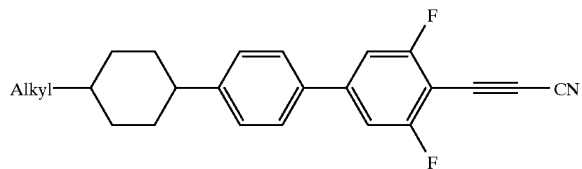
(1b-17)

-continued
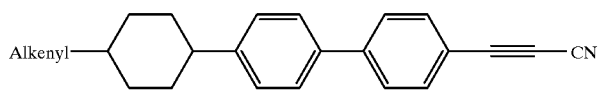
(1b-18)
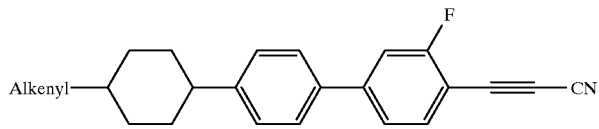
(1b-19)
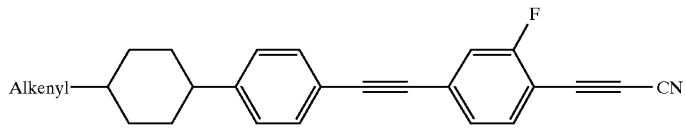
(1b-20)
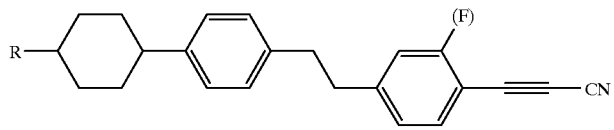
(1b-21)
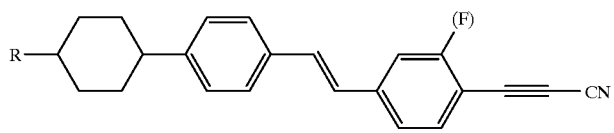
(1b-22)
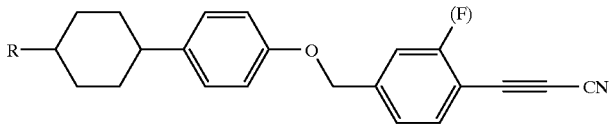
(1b-23)
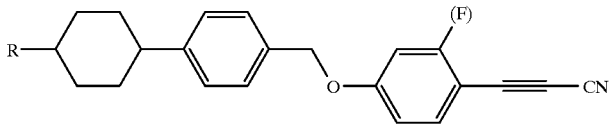
(1b-24)
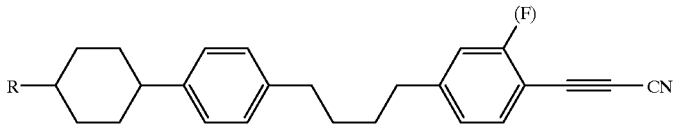
(1b-25)
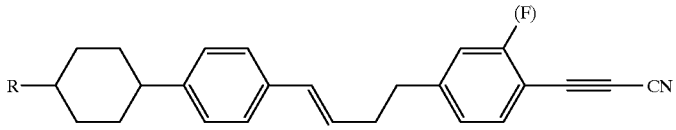
(1b-26)
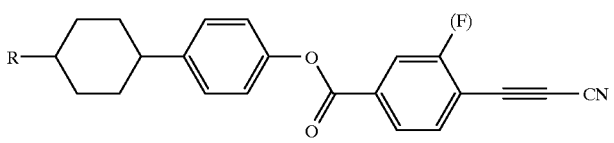
(1b-27)

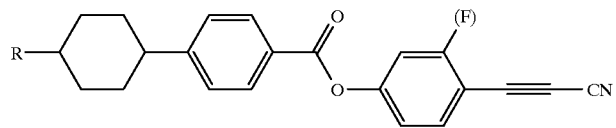
(1b-28)
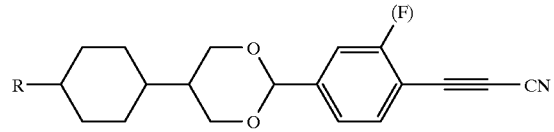
(1b-29)
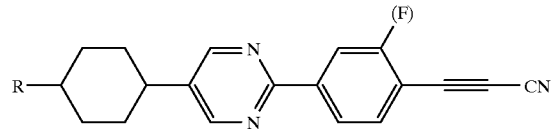
(1b-30)
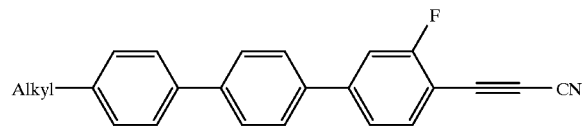
(1b-31)
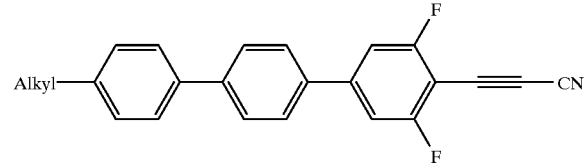
(1b-32)
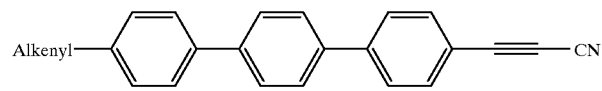
(1b-33)
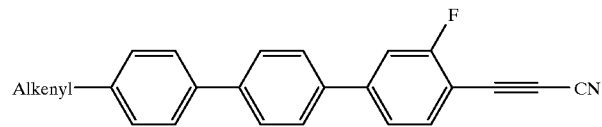
(1b-34)
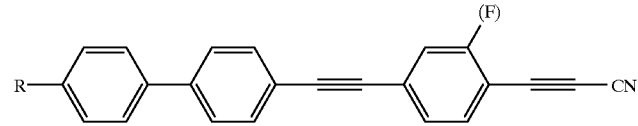
(1b-35)
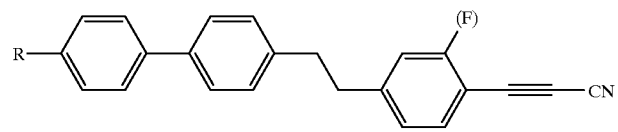
(1b-36)

-continued
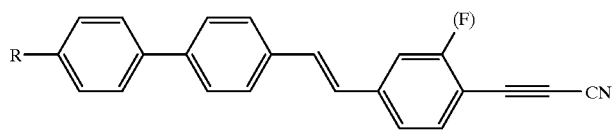
(1b-37)
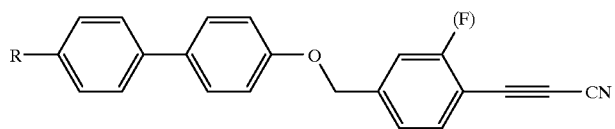
(1b-38)
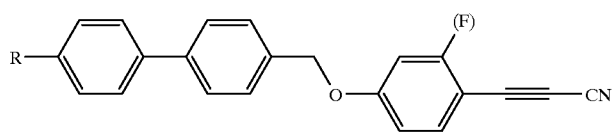
(1b-39)
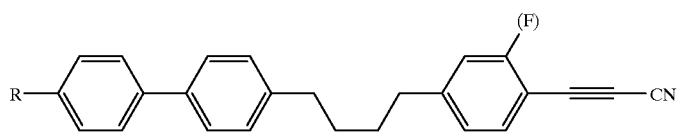
(1b-40)
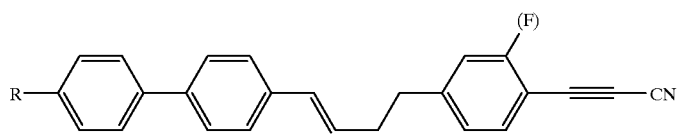
(1b-41)
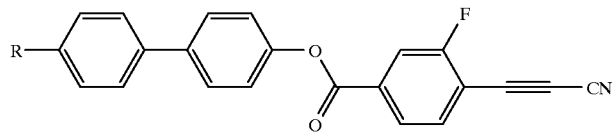
(1b-42)
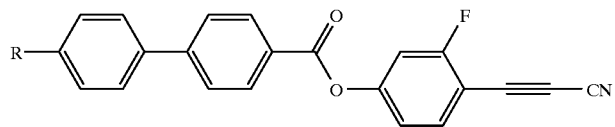
(1b-43)
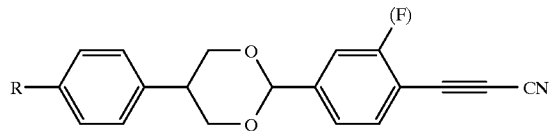
(1b-44)
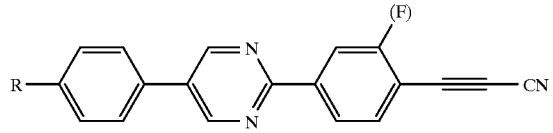
(1b-45)

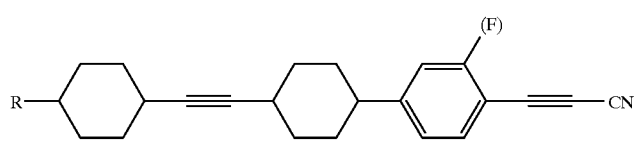
(1b-46)
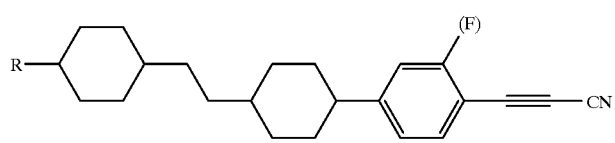
(1b-47)
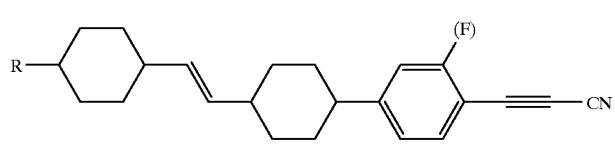
(1b-48)
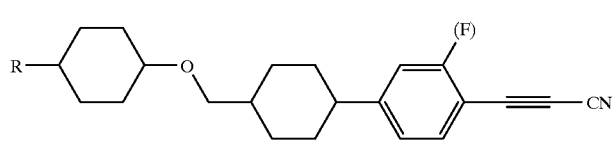
(1b-49)
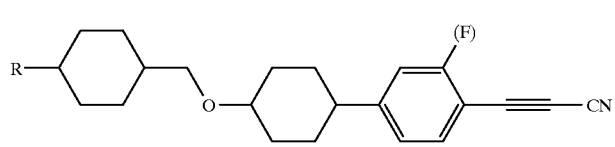
(1b-50)
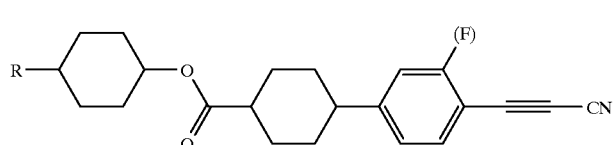
(1b-51)
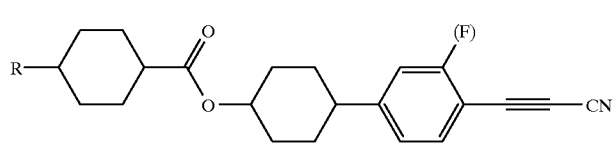
(1b-52)
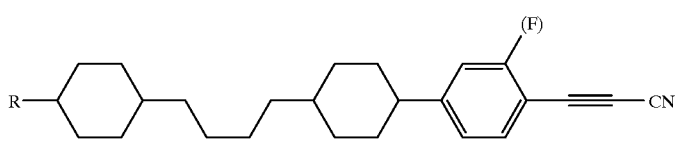
(1b-53)
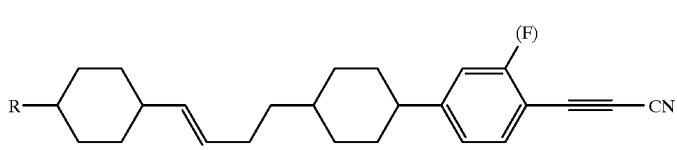
(1b-54)

-continued
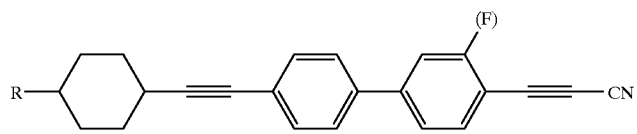
(1b-55)
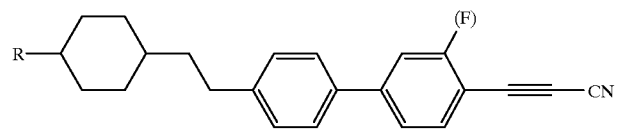
(1b-56)
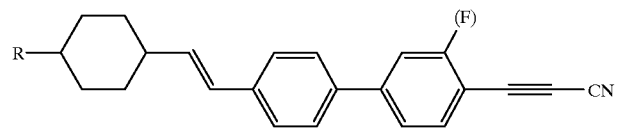
(1b-57)
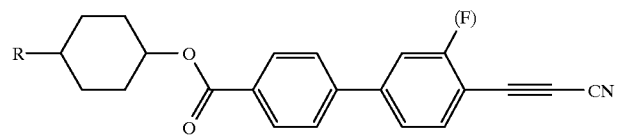
(1b-58)
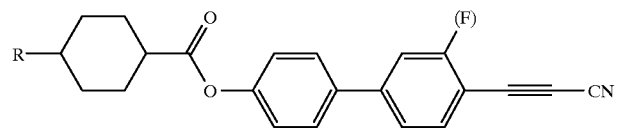
(1b-59)
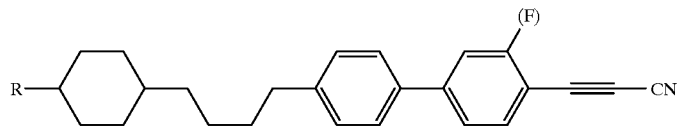
(1b-60)
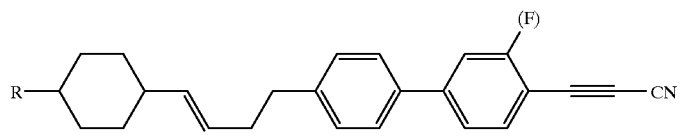
(1b-61)
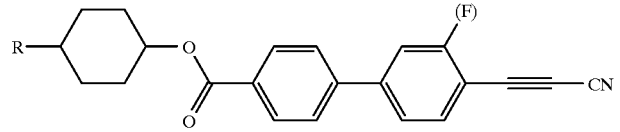
(1b-62)
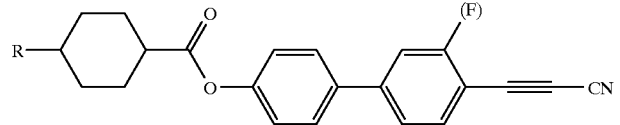
(1b-63)
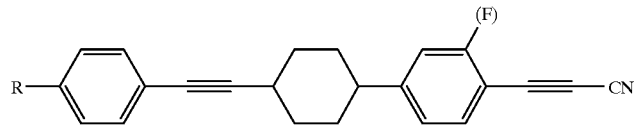
(1b-64)

-continued
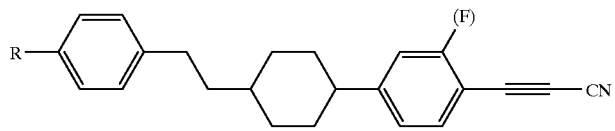
(1b-65)
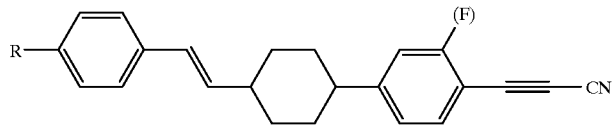
(1b-66)
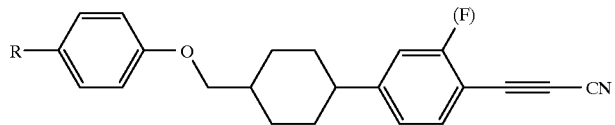
(1b-67)
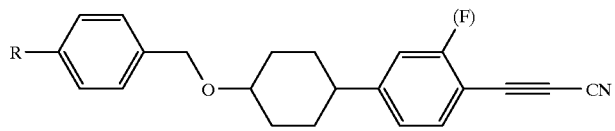
(1b-68)
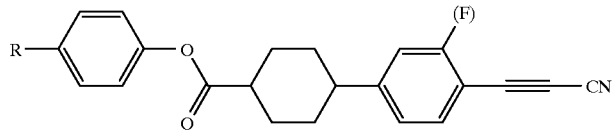
(1b-69)
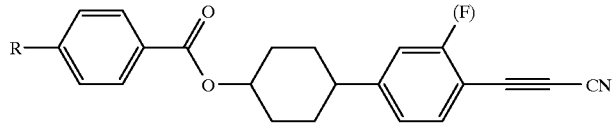
(1b-70)
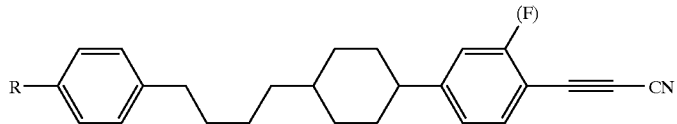
(1b-71)
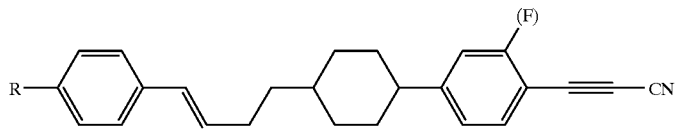
(1b-72)
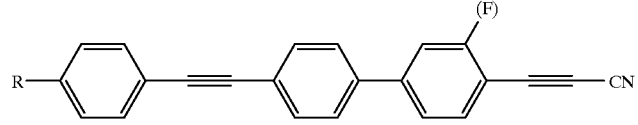
(1b-73)
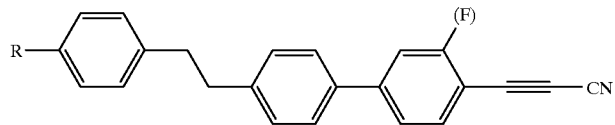
(1b-74)

-continued (1b-75)
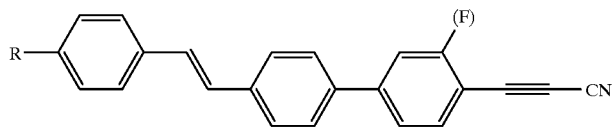

(1b-76)
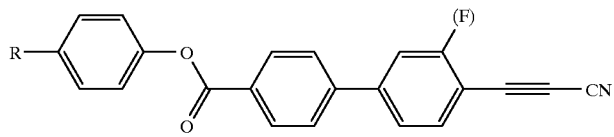

(1b-77)
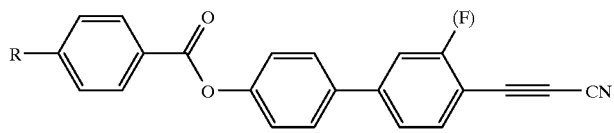

(1b-78)
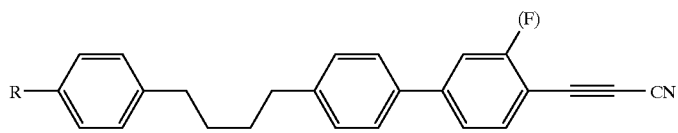

(1b-79)
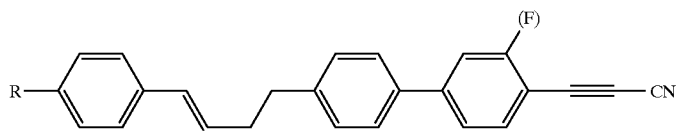

(1b-80)
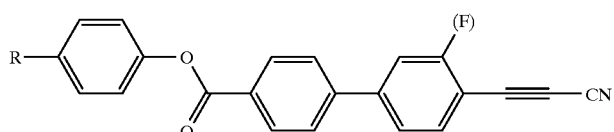

(1b-81)
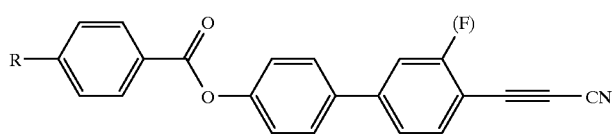

The four ring system compounds of formula (1c) have very high clearing points, higher elastic constant ratio and relatively higher optical anisotropy, and so they are very important as the ingredient constituting the liquid crystal composition. More specific examples of the four ring system compounds are represented by the following formulas (1c-1) to (1c-33) wherein A1, A2, A3, Alkyl, Alkenyl, R and (F) have the same meaning as defined above.

(1c-1)
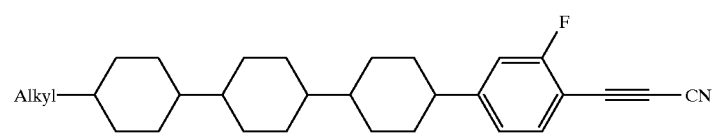

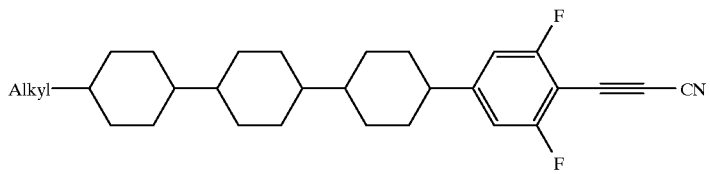
(1c-2)
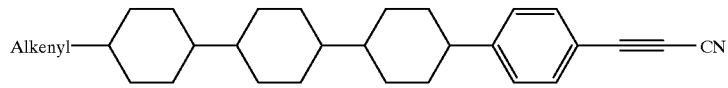
(1c-3)
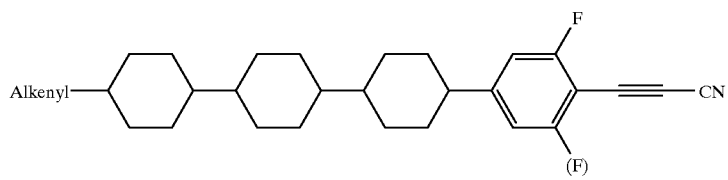
(1c-4)
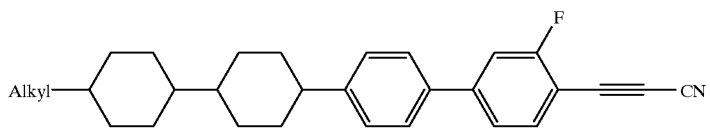
(1c-5)
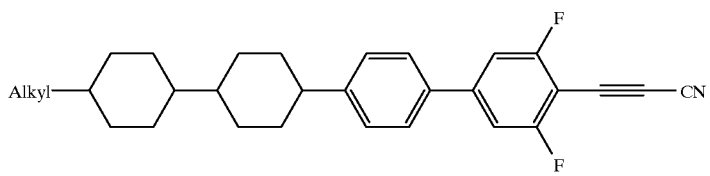
(1c-6)
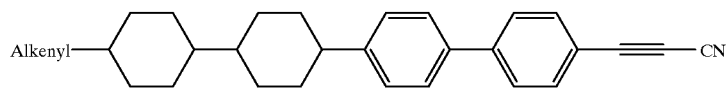
(1c-7)
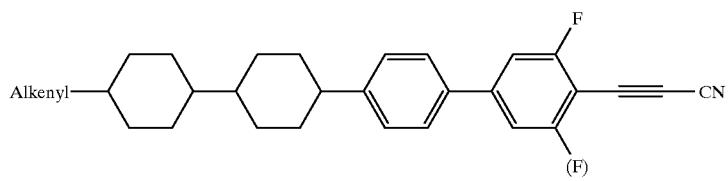
(1c-8)
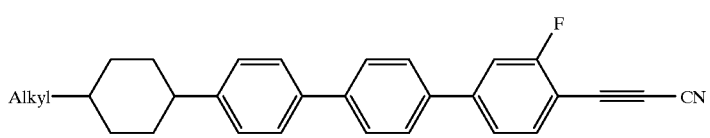
(1c-9)
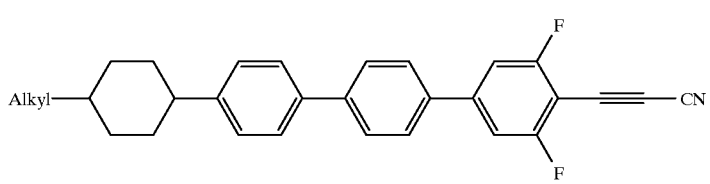
(1c-10)

-continued
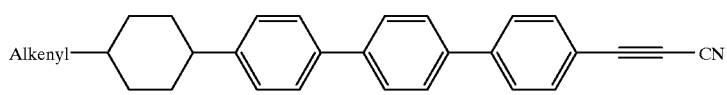
(1c-11)
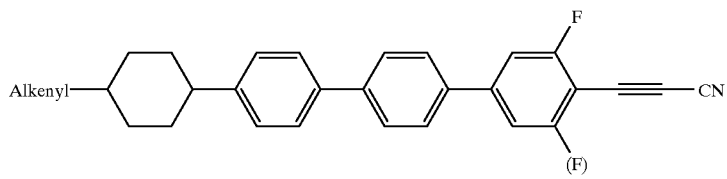
(1c-12)
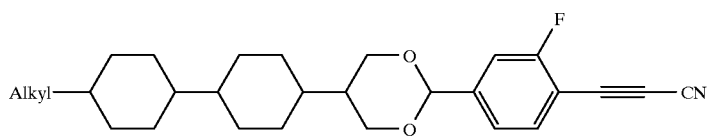
(1c-13)
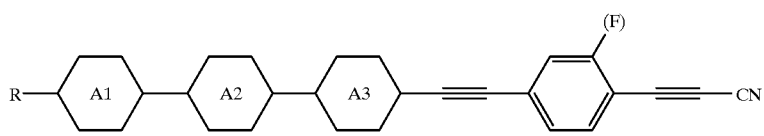
(1c-14)
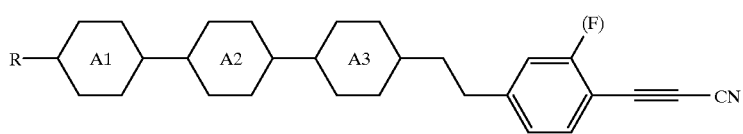
(1c-15)
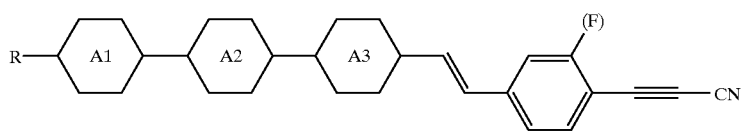
(1c-16)
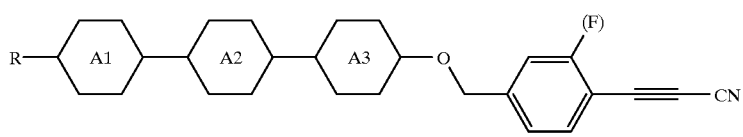
(1c-17)
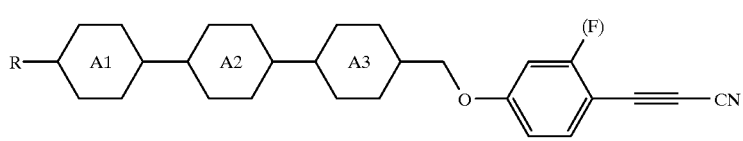
(1c-18)
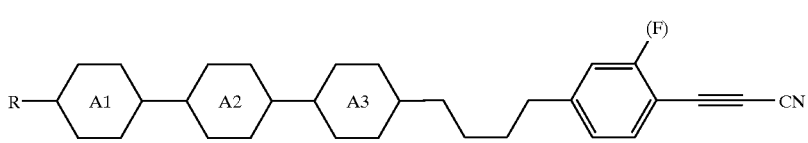
(1c-19)
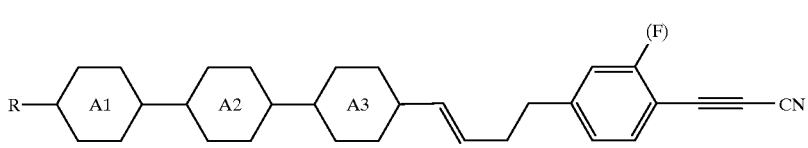
(1c-20)

-continued
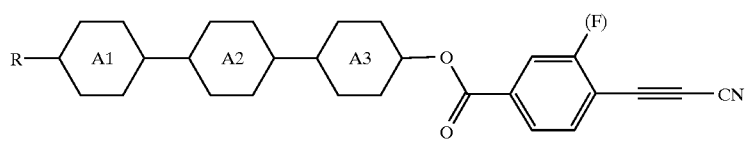
(1c-21)
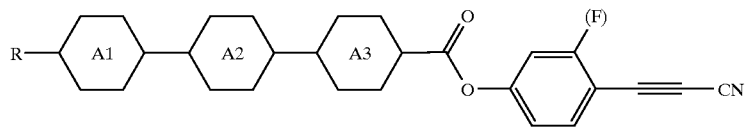
(1c-22)
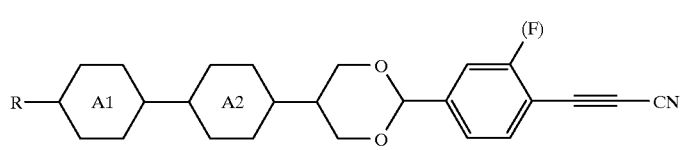
(1c-23)
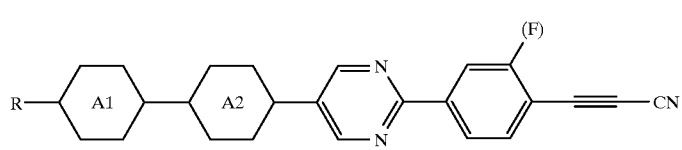
(1c-24)
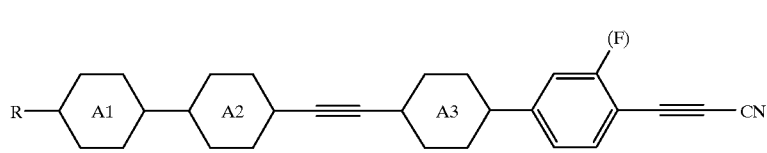
(1c-25)
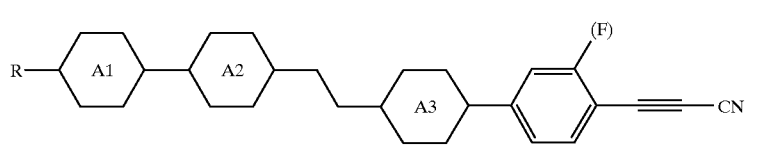
(1c-26)
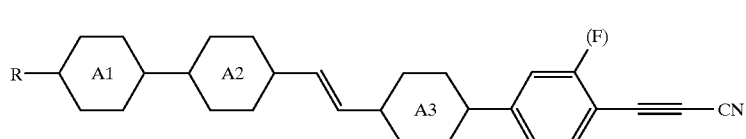
(1c-27)
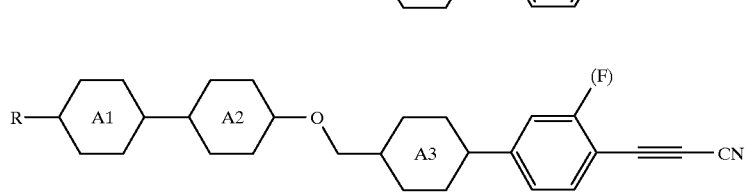
(1c-28)
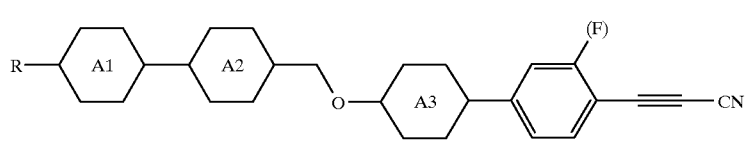
(1c-29)

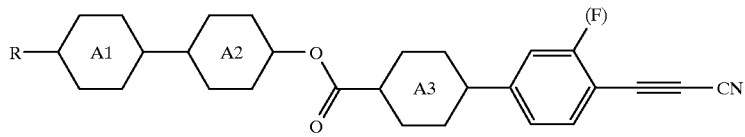
(1c-30)

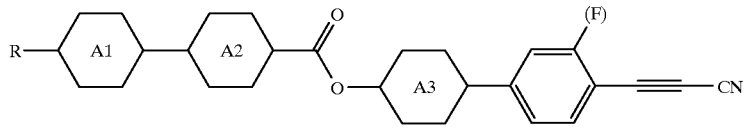
(1c-31)

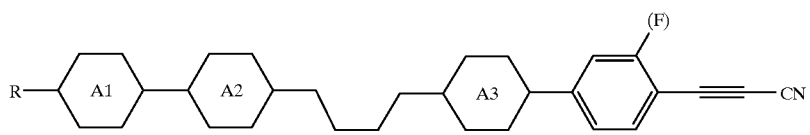
(1c-32)

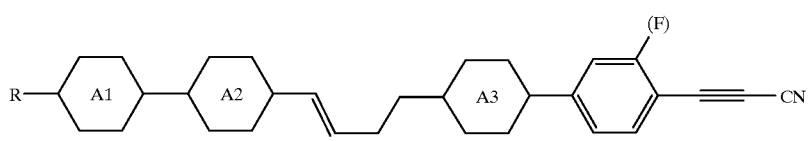
(1c-33)

The physical properties of the propiolonitrile derivatives can be adjusted to a desired level by choice and combination of rings A1, A2 and A3, choice and combination of bridges Z1, Z2 and Z3 between the rings and choice of a terminal group R and the substituents X1 and X2 on the ring in the molecular structure of formula (1), and thus the propiolonitrile derivatives of the present invention can be advantageously used as the ingredient of the liquid crystal composition having good characteristics.

The compounds of formula (1) wherein the terminal group R is alkyl or alkenyl, i.e. those of formulas (1a-1) to (1a-5), (1a-15) to (1a-19), (1b-1) to (1b-5), (1b-16) to (1b-20) and (1b-31) to (1b-34) as well as (1c-1) to (1c-13) have higher clearing points, higher elastic constant ratio, higher dielectric anisotropy and higher optical anisotropy, which are very suitable for the ingredients of the liquid crystal materials.

In particular, the compounds of formulas (1a-3) to (1a-5), (1a-17) to (1a-19), (1b-3) to (1b-5), (1b-18) to (1b-20), (1b-33) and (1b-34) as well as (1c-3, -4, -7, -8, -11 and -12) have higher elastic constant ratio and lower viscosity, which are useful as a display material of the STN mode.

The compounds of formula (1) wherein any one of Z1, Z2 and Z3 is ethylene, 1,4-butylene or 1,4-butenylene, i.e. those of formulas (1a-7,-11, -12, -21, -25 and -26), (1b-6, -10, -11, -21, -25, -26, -36, -40, -41, -47, -53, -54, -56, -60, -61, 65, -71, -72, 74, -78 and -79) as well as (1c-15, -19, -20, -26, -32 and -33) have higher compatibility and suitable broader nematic liquid crystal phase for the application of a liquid crystal display, thus being useful.

The compounds of formula (1) having a highly conjugated partial structure, i.e. those of formulas (1a-6, -8, -15 to -20, -22 and -26), (1b-5, -7, -16 to -20, -22, -26, -30, -31 to -43, -45, -46, -48, -55, -57, -64, -66 and -73 to -81) as well as (1c-5 to -12, -14, -16, -25 and -27) have broad liquid crystal temperature range and particularly higher optical anisotropy, which are useful as the liquid crystal materials for display having a thinner cell thickness. In particular, the compounds of formulas (1a-20 and -22 as well as 1b-20, -22, -35, -37, -55, -73 and -75) have beyond comparison high optical anisotropy, which are useful as the materials used in polymer dispersion type liquid crystal display elements.

The compounds of formula (1) wherein any one of Z1, Z2 and Z3 is oxycarbonyl or carbonyloxy or any one of A1, A2 and A3 is 1,3-dioxane-2,5-diyl or 1,3-pyrimidine-2,5-diyl, i.e. the ester, pyrimidine and dioxane derivatives represented by formulas (1a-13, -14, -27 and -28), (1b-12, -13, -14, -15, -27, -28, -29, -30, -42, -43, -44, -45, -51, -52, -58, -59, -62, -63, -69, -70, -76, -77, -80 and -81) as well as (1c-12, -13, -21, -22, -23 and -24) have especially high dielectric anisotropy, which are very suitable for the liquid crystal material for a low voltage driving display.

The compounds of formulas (1a-i) to (1a-14), (1b-1) to (1b-30) and (1b-46) to (1b-72) as well as (1c-1) to (1c-13) containing a cyclohexane ring in the backbone structure have broader liquid crystal temperature range and good compatibility with other liquid crystalline compounds.

In the propiolonitrile derivatives of formula (1), one or more hydrogens adjacent to a propiolonitrile group on the phenyl ring attached to the propiolonitrile may be substituted by a fluorine atom. Such F-containing compounds have higher dielectric anisotropy, which are useful as the ingredients of the liquid crystal composition for the STN with a view to setting the driving voltage lower. The compounds wherein the phenyl ring is not substituted by F can provide the liquid crystal composition with higher clearing points than the fluorine containing compounds.

The propiolonitrile derivatives of formula (1) according to the present invention can be synthesized by any of the following processes A to C.

A-1. Synthesis of the compounds of formula (1) wherein none of bridges Z1, Z2 and Z3 are ester linkage (carbonyloxy or oxycarbonyl)

The propiolonitrile derivatives of formula (1) wherein Z1, Z2 and Z3 each independently represent a single bond, ethylene, ethenylene, ethynylene, methyleneoxy, oxymethylene, 1,4-butylene or 1,4-butenylene and n1, n2, R, A1, A2, A3, X1 and X2 have the same meaning as defined above are prepared by cyanation of ethynylene halides of the following formula (4) wherein X3 is Cl, Br or I, n1, n2, R, A1, A2, A3, Z1, Z2, Z3, X1 and X2 have the same meaning as defined above, with the agents for cyanation.

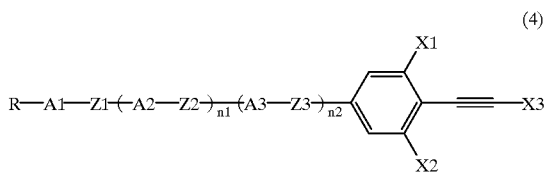

This reaction is generally carried out in an aprotic, polar solvent using as the cyanating agent, metal cyanides, preferably sodium cyanide, copper cyanide, potassium cyanide or the like. The amount of metal cyanides used ranges from one equivalent to a large excess based on the substrate, preferably 1–3 equivalents considering after-treatment. The preferred aprotic, polar solvents include tetrahydrofuran, dimethylformamide, acetonitrile, acetone, dioxane, N-methylpyrrolidone or the like. Especially preferable are tetrahydrofuran, acetonitrile, dimethylformamide and N-methylpyrrolidone, since they give good yield. The reaction temperature is selected from the ranges between room temperature and the boiling points of the chosen solvents, but the temperature in the neiborhood of boiling point of the solvent is preferable for prompt progress of the reaction.

For the purpose of securing prompt progress of the reaction and increasing the yield, the additives may be added. As the additives are preferable the salts such as lithium bromide, lithium chloride, sodium bromide, sodium iodide or the like.

The amount of additives added is selected from the range of 1–200 mole % based on the reaction substrate.

The halogenated ethynylenes of formula (4) which are starting materials in the reaction can be readily synthesized from the aldehyde compounds of formula (5) using the process disclosed in DE 4027458 or the process shown in the following reaction scheme in which Z1, Z2, Z3, n1, n2, R, A1, A2, A3, X1 and X2 have the same meaning as defined above.

ethynylene, methyleneoxy, oxymethylene, 1,4-butylene or 1,4-butenylene are prepared by an esterification reaction of a carboxylic acid compound of the following formula (6) with an alcohol compound of the following formula (7) or by an esterification reaction of an alcohol compound of the following formula (8) with a carboxylic acid compound of the following formula (9). In formulas (6) to (9), n'1, n"1, n'2 and n"2 are 0 or 1, and n'1+n"1=1, n'2+n"2=1, and R, A1, A2, A3, X1 and X2 have the same meaning as defined above.

As this esterification reaction can be employed most conventional process in which the reaction is carried out in a solvent inert to the reaction per se, such as toluene, xylene or the like and in the presence of an acid catalyst, while dehydrating azeotropically, a process in which the reaction is performed in an aprotic, polar solvent and in the presence of a base using a dehydrating agent for condensation such as DCC, and other processes. Suitable processes for the substrate can be employed.

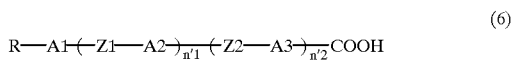

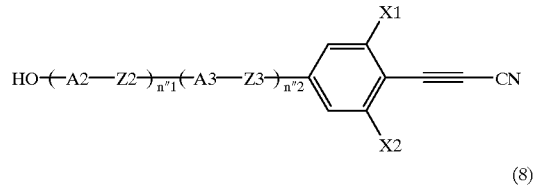

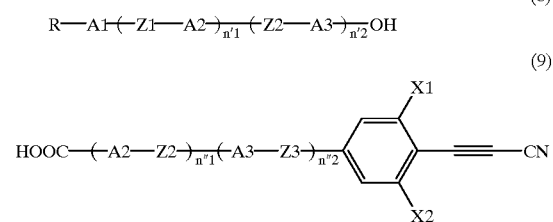

Alternatively, the propiolonitrile derivatives of the present invention can be synthesized by reacting the carboxylic acid compound of formula (6) or the carboxylic acid compound of formula (9) with a halogenation agent such as thionyl halide in an inert solvent to form the corresponding acid

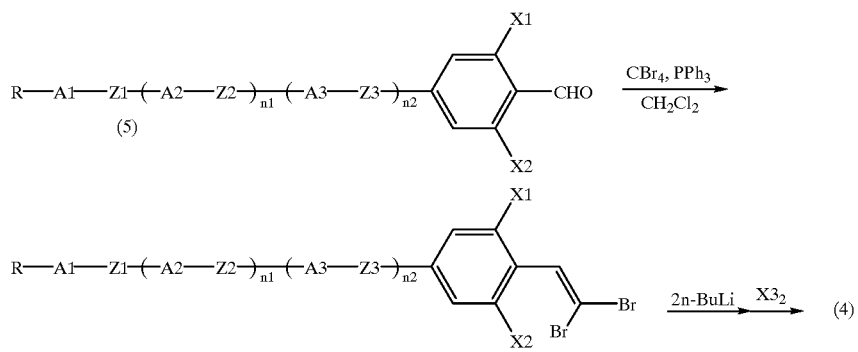

A-2. Synthesis of the compounds of formula (1) wherein any one of Z1, Z2 and Z3 is an ester linkage (carbonyloxy or oxycarbonyl)

The propiolonitrile derivatives of formula (1) wherein any one of Z1, Z2 and Z3 is carbonyloxy or oxycarbonyl and the other independently is a single bond, ethylene, ethenylene, halide of formula (10) or (11) wherein X4 represents Cl, Br or I and n'1, n"1, n'2, n"2, R, A1, A2, A3, Z1, Z2, Z3, X1 and X2 have the same meaning as defined above, followed by esterification with the alcohol compound of formula (7) or (8), and finally subjecting to dehydrohalogenation treatment in an inert solvent and in the presence of a base with no catalyst.

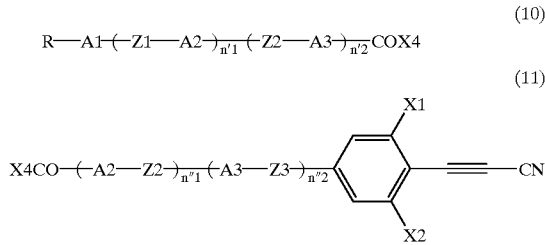

The alcohol compounds of formulas (7) and (9) which are starting materials in the present reaction are readily prepared by application of the later-mentioned process C or the methods known per se. The carboxylic acid compounds of formulas (6) and (8) are prepared for example by the methods disclosed in Japanese Patent Kokai 4-501275, 4-503523 or 59-122440.

B. Synthesis of the compounds of formula (1) not containing other unsaturated bond than the propiolonitrile group in the molecule The propiolonitrile derivatives of formula (1) wherein Z1, Z2 and Z3 each independently represents a single bond, ethylene, carbonyloxy, oxycarbonyl, methyleneoxy or 1,4-butylene and R represents a saturated hydrocarbyl can be prepared by reacting a cinnamonitrile derivative of the following formula (12) with bromine to form a dibromo compound of the following formula (13) and subjecting the dibromo compound to dehydrobromination with a base. In formulas (12) and (13), n1, n2, A1, A2, A3, X1 and X2 have the same meaning as defined above. The bromination of the cinnamonitrile derivative of formula (12) to the bibromo compound of formula (13) is carried out by adding one or more equivalents bromine based on the cinnamonitrile derivative at ordinary temperatures in an inert solvent such as chloroform, carbon tetrachloride, dichloroethylene, dichloromethane or the like. The dibromo compound of formula (13) can be reacted with one or more equivalents base, e.g. diazabicycloundecene, potassium butoxide, sodium hydride, in a solvent inert to the reaction such as tetrahydrofuran, dioxane, toluene, benzene, to provide the propiolonitrile derivative of formula (1).

The cinnamonitrile derivative of formula (12) is prepared by reacting the aldehyde compound of formula (5) with diethylcyanomethyl phosphonate and sodium hydride in an aprotic, polar solvent, as shown in the following reaction scheme (14).

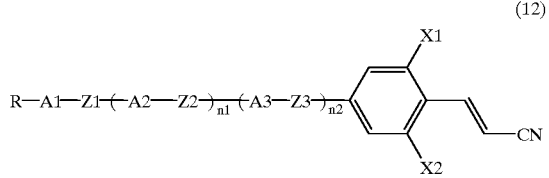

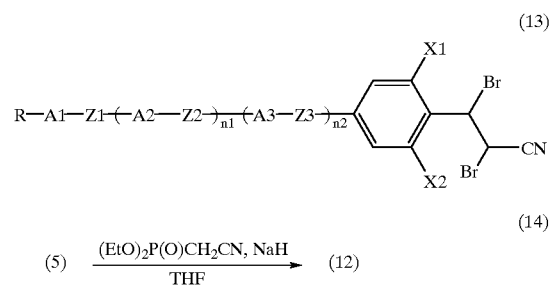

C. Synthesis of the compounds of formula (1) not containing a thermally unstable partial structure in the molecule The propiolonitrile derivative of formula (1) can be prepared by reacting an acid halide of the following formula (15) with cyanomethylenetriphenylphosphorane in a solvent inert to the reaction, e.g. benzene, toluene, monochlorobenzene, nitrobenzene, to provide a phosphorane derivative of the following formula (16) and heating the derivative under reduced pressure, e.g. at 200–300° C. for thermal decomposition. In formulas (15) and (16), n1, n2, A1, A2, A3, Z1, Z2, Z3, R, X1 and X2 have the same meaning as defined for the formula (1). The acid halide of formula (15) which is a starting material for this reaction can be prepared by reacting the carboxylic acid derivative prepared by oxidation of the aldehyde derivative of formula (5), with a halogenating agent such as thionyl halide.

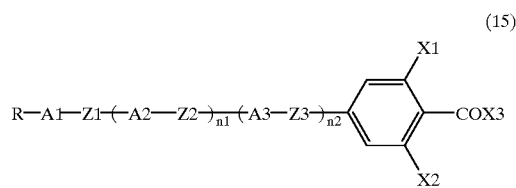

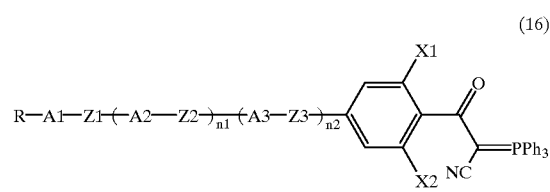

Specific examples of the propiolonitrile derivatives according to the present invention are shown in the following tables.

TABLE 1

| No. | R | A1-Z1 | n1 | n2 | X1 | X2 | |
|---|---|---|---|---|---|---|---|
| 1 | CH$_3$ | cyclohexyl | 0 | 0 | F | H | |
| 2 | n-C$_3$H$_7$ | cyclohexyl | 0 | 0 | F | H | CN 51.5° C., NI 96.9° C. |
| 3 | n-C$_3$H$_7$ | cyclohexyl | 0 | 0 | F | F | CI 66.9° C., NI 49.1° C. |
| 4 | n-C$_7$H$_{15}$ | cyclohexyl | 0 | 0 | F | H | |
| 5 | CH$_3$OCH$_2$ | cyclohexyl | 0 | 0 | F | H | |
| 6 | CH$_2$=CH | cyclohexyl | 0 | 0 | H | H | CN 66.8° C., NI 122.7° C. |
| 7 | CH$_2$=CHCH$_2$CH$_2$ | cyclohexyl | 0 | 0 | H | H | CN 65.4° C., NI 134.9° C. |
| 8 | CH$_2$=CHCH$_2$CH$_2$ | cyclohexyl | 0 | 0 | F | F | CN 58.3° C., NI 80.4° C. |
| 9 | CH$_2$=CH—(CH$_2$)$_2$—CH=CH | cyclohexyl | 0 | 0 | H | H | |
| 10 | CH$_2$=CHCH$_2$O | cyclohexyl | 0 | 0 | F | H | |

CN: Crystal to nematic transition temperature
NI: Nematic to isotropic phase transition temperature
CI: Crystal to isotropic phase transition temperature

TABLE 2
| No. | R | A1-Z1 | n1 | n2 | X1 | X2 |
|---|---|---|---|---|---|---|
| 11 | CH₃ | 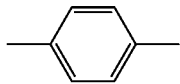 | 0 | 0 | F | H |
| 12 | n-C₃H₇ | 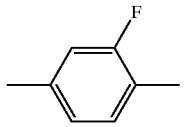 | 0 | 0 | F | H |
| 13 | n-C₅H₁₁ | 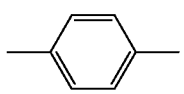 | 0 | 0 | F | H |
| 14 | n-C₇H₁₅ | 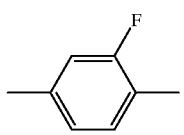 | 0 | 0 | F | H |
| 15 | CH₃OCH₂ | 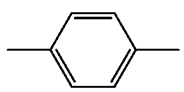 | 0 | 0 | F | H |
| 16 | CH₂=CH | 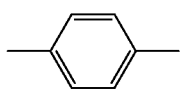 | 0 | 0 | H | H |
| 17 | CH₂=CHCH₂CH₂ | 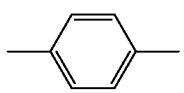 | 0 | 0 | F | H |
| 18 | CH₃CH=CH—(CH₂)₂ | 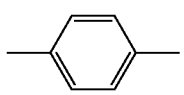 | 0 | 0 | H | H |
| 19 | CH₂=CH—(CH₂)₂—CH=CH | 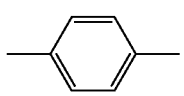 | 0 | 0 | H | H |
| 20 | CH₂=CHCH₂O | 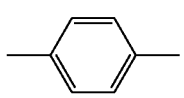 | 0 | 0 | F | H |
TABLE 3
| No. | R | A1-Z1 | n1 | n2 | X1 | X2 |
|---|---|---|---|---|---|---|
| 21 | CH₃ | 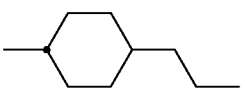 | 0 | 0 | F | H |

TABLE 3-continued
| No. | R | A1-Z1 | n1 | n2 | X1 | X2 | |
|---|---|---|---|---|---|---|---|
| 22 | n-C$_3$H$_7$ | 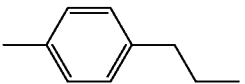 | 0 | 0 | F | H | |
| 23 | n-C$_5$H$_{11}$ | 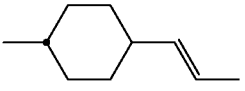 | 0 | 0 | H | H | |
| 24 | n-C$_7$H$_{15}$ | 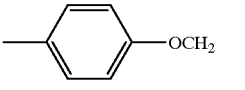 | 0 | 0 | F | H | |
| 25 | CH$_3$ | 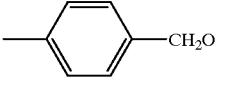 | 0 | 0 | F | H | |
| 26 | n-C$_3$H$_7$ | 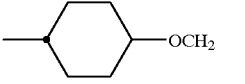 | 0 | 0 | H | H | |
| 27 | n-C$_5$H$_{11}$ | 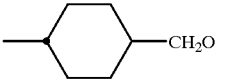 | 0 | 0 | F | H | |
| 28 | n-C$_7$H$_{15}$ | 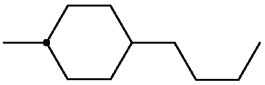 | 0 | 0 | H | H | |
| 29 | CH$_3$ | 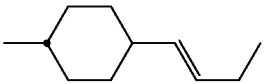 | 0 | 0 | H | H | |
| 30 | n-C$_3$H$_7$ | 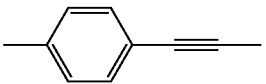 | 0 | 0 | F | H | CN 60.4° C., NI 128.2° C. |

TABLE 4

| No. | R | A1-Z1 | n1 | n2 | X1 | X2 |
|---|---|---|---|---|---|---|
| 31 | CH$_2$=CH | cyclohexyl-CH$_2$CH$_2$- | 0 | 0 | H | H |
| 32 | CH$_2$=CH(CH$_2$)$_2$ | cyclohexyl-CH$_2$CH$_2$- | 0 | 0 | F | H |
| 33 | CH$_3$CH=CH(CH$_2$)$_2$ | cyclohexyl-CH=CH- | 0 | 0 | H | H |
| 34 | CH$_2$=CH | phenyl-OCH$_2$- | 0 | 0 | F | H |
| 35 | CH$_2$=CH(CH$_2$)$_2$ | phenyl-CH$_2$O- | 0 | 0 | F | H |
| 36 | CH$_3$CH=CH(CH$_2$)$_2$ | cyclohexyl-OCH$_2$- | 0 | 0 | H | H |
| 37 | CH$_2$=CH | cyclohexyl-CH$_2$O- | 0 | 0 | F | H |
| 38 | CH$_2$=CH(CH$_2$)$_2$ | cyclohexyl-CH$_2$CH$_2$CH$_2$- | 0 | 0 | H | H |
| 39 | CH$_3$CH=CH(CH$_2$)$_2$ | cyclohexyl-CH=CHCH$_2$- | 0 | 0 | H | H |
| 40 | CH$_2$=CHCH$_2$O | cyclohexyl-C≡C- | 0 | 0 | F | H |

TABLE 5

| No. | R | A1-Z1 | n1 | A2-Z2 | n2 | X1 | X2 |
|---|---|---|---|---|---|---|---|
| 41 | CH$_3$ | cyclohexyl- | 1 | cyclohexyl-CH$_2$CH$_2$- | 0 | F | H |

TABLE 5-continued

| No. | R | A1-Z1 | n1 | A2-Z2 | n2 | X1 | X2 |
|---|---|---|---|---|---|---|---|
| 42 | n-C$_3$H$_7$ | (cyclohexyl) | 1 | (phenyl)-propyl | 0 | F | H |
| 43 | n-C$_5$H$_{11}$ | (cyclohexyl) | 1 | (cyclohexyl)-propyl | 0 | F | H |
| 44 | n-C$_7$H$_{15}$ | (cyclohexyl) | 1 | (phenyl)-OCH$_2$ | 0 | F | H |
| 45 | CH$_3$OCH$_2$ | (cyclohexyl) | 1 | (phenyl)-CH$_2$O | 0 | F | H |
| 46 | CH$_2$=CH | (cyclohexyl) | 1 | (cyclohexyl)-OCH$_2$ | 0 | H | H |
| 47 | CH$_2$=CHCH$_2$CH$_2$ | (cyclohexyl) | 1 | (cyclohexyl)-CH$_2$O | 0 | F | H |
| 48 | CH$_3$CH=CH—(CH$_2$)$_2$ | (cyclohexyl) | 1 | (cyclohexyl)-butyl | 0 | H | H |
| 49 | CH$_2$=CH—(CH$_2$)$_2$—CH=CH | (cyclohexyl) | 1 | (cyclohexyl)-CH=CH-ethyl | 0 | H | H |
| 50 | CH$_2$=CHCH$_2$O | (cyclohexyl) | 1 | (cyclohexyl)-C≡CH | 0 | F | H |

TABLE 6

| No. | R | A1-Z1 | n1 | A2-Z2 | n2 | X1 | X2 |
|---|---|---|---|---|---|---|---|
| 51 | CH$_3$ | (phenyl) | 1 | (cyclohexyl)-propyl | 0 | F | H |
| 52 | n-C$_3$H$_7$ | (fluorophenyl) | 1 | (phenyl)-propyl | 0 | H | H |

TABLE 6-continued

| No. | R | A1-Z1 | n1 | A2-Z2 | n2 | X1 | X2 |
|---|---|---|---|---|---|---|---|
| 53 | n-C$_5$H$_{11}$ | phenyl- | 1 | cyclohexyl-propyl | 0 | F | H |
| 54 | n-C$_7$H$_{15}$ | phenyl(F)- | 1 | phenyl-OCH$_2$ | 0 | H | H |
| 55 | CH$_3$OCH$_2$ | phenyl- | 1 | phenyl-CH$_2$O | 0 | F | H |
| 56 | CH$_2$=CH | phenyl- | 1 | cyclohexyl-OCH$_2$ | 0 | H | H |
| 57 | CH$_2$=CHCH$_2$CH$_2$ | phenyl- | 1 | cyclohexyl-CH$_2$O | 0 | F | H |
| 58 | CH$_3$CH=CH—(CH$_2$)$_2$ | phenyl- | 1 | cyclohexyl-butyl | 0 | H | H |
| 59 | CH$_2$=CH—(CH$_2$)$_2$—CH=CH | phenyl- | HI | cyclohexyl-CH=CH-propyl | 0 | H | H |
| 60 | CH$_2$=CHCH$_2$O | phenyl- | 1 | phenyl-C≡C- | 0 | F | H |

TABLE 7

| No. | R | A1-Z1 | n1 | A2-Z2 | n2 | X1 | X2 |
|---|---|---|---|---|---|---|---|
| 61 | CH$_3$ | cyclohexyl-ethyl | 1 | cyclohexyl- | 0 | F | H |
| 62 | n-C$_3$H$_7$ | phenyl-ethyl | 1 | cyclohexyl- | 0 | F | H |
| 63 | n-C$_5$H$_{11}$ | cyclohexyl-CH=CH | 1 | cyclohexyl- | 0 | H | H |

TABLE 7-continued
| No. | R | A1-Z1 | n1 | A2-Z2 | n2 | X1 | X2 |
|---|---|---|---|---|---|---|---|
| 64 | n-C$_7$H$_{15}$ | 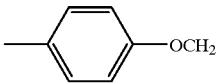 | 1 | 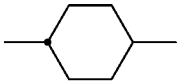 | 0 | F | H |
| 65 | CH$_3$OCH$_2$ | 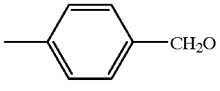 | 1 | 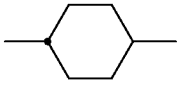 | 0 | F | H |
| 66 | CH$_2$=CH | 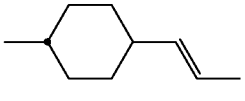 | 1 | 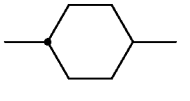 | 0 | H | H |
| 67 | CH$_2$=CHCH$_2$CH$_2$ | 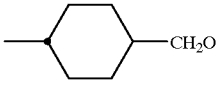 | 1 | 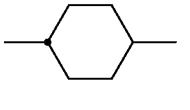 | 0 | F | H |
| 68 | CH$_3$CH=CH—(CH$_2$)$_2$ | 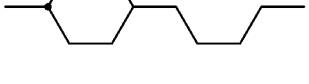 | 1 | 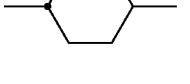 | 0 | H | H |
| 69 | CH$_2$=CH—(CH$_2$)$_2$—CH=CH | 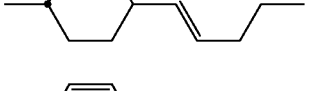 | 1 | 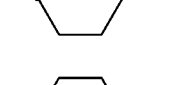 | 0 | H | H |
| 70 | CH$_2$=CHCH$_2$O |  | 1 | 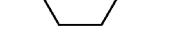 | 0 | F | H |
TABLE 8
| No. | R | A1—Z1 | n1 | A2—Z2 | n2 | X1 | X2 |
|---|---|---|---|---|---|---|---|
| 71 | CH$_3$ | 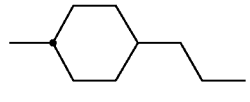 | 1 |  | 0 | F | H |
| 72 | n-C$_3$H$_7$ | 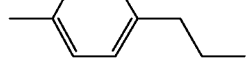 | 1 | 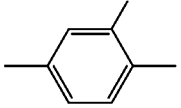 | 0 | H | H |
| 73 | n-C$_5$H$_{11}$ | 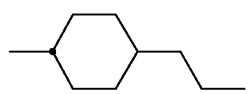 | 1 |  | 0 | F | H |
| 74 | n-C$_7$H$_{15}$ | 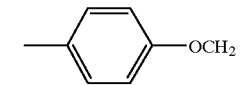 | 1 |  | 0 | F | H |

TABLE 8-continued

| No. | R | A1—Z1 | n1 | A2—Z2 | n2 | X1 | X2 |
|---|---|---|---|---|---|---|---|
| 75 | $CH_3OCH_2$ | 4-phenyl-CH₂O— | 1 | 2-fluoro-phenyl | 0 | F | F |
| 76 | $CH_2=CH$ | cyclohexyl-OCH₂— | 1 | phenyl | 0 | H | H |
| 77 | $CH_2=CHCH_2CH_2$ | cyclohexyl-CH₂O— | 1 | phenyl | 0 | F | H |
| 78 | $CH_3CH=CH—(CH_2)_2$ | cyclohexyl-(CH₂)₃— | 1 | phenyl | 0 | H | H |
| 79 | $CH_2=CH—(CH_2)_2—CH=CH$ | cyclohexyl-CH=CH-CH₂— | 1 | phenyl | 0 | H | H |
| 80 | $CH_2=CHCH_2O$ | phenyl-C≡C— | 1 | phenyl | 0 | F | H |

TABLE 9

| No. | R | A1—Z1 | n1 | A2—Z2 | n2 | X1 | X2 |
|---|---|---|---|---|---|---|---|
| 81 | $CH_3$ | cyclohexyl | 1 | cyclohexyl | 0 | F | H |
| 82 | $n\text{-}C_3H_7$ | cyclohexyl | 1 | phenyl | 0 | F | H |
| 83 | $n\text{-}C_5H_{11}$ | cyclohexyl | 1 | cyclohexyl | 0 | F | H |
| 84 | $n\text{-}C_7H_{15}$ | cyclohexyl | 1 | phenyl | 0 | F | H |
| 85 | $CH_3OCH_2$ | cyclohexyl | 1 | cyclohexyl | 0 | F | H |

TABLE 9-continued

| No. | R | A1—Z1 | n1 | A2—Z2 | n2 | X1 | X2 |
|---|---|---|---|---|---|---|---|
| 86 | $CH_2=CH$ | cyclohexyl | 1 | cyclohexyl | 0 | H | H |
| 87 | $CH_3CH=CH$ | cyclohexyl | 1 | cyclohexyl | 0 | H | H |
| 88 | $CH_3CH=CH-(CH_2)_2$ | cyclohexyl | 1 | cyclohexyl | 0 | H | H |
| 89 | $CH_2=CH-(CH_2)_2-CH=CH$ | cyclohexyl | 1 | cyclohexyl | 0 | H | H |
| 90 | $CH_2=CHCH_2O$ | cyclohexyl | 1 | phenyl | 0 | F | H |

TABLE 10

| No. | R | A1—Z1 | n1 | A2—Z2 | n2 | X1 | X2 |
|---|---|---|---|---|---|---|---|
| 91 | $CH_3$ | phenyl | 1 | cyclohexyl | 0 | F | H |
| 92 | $n\text{-}C_3H_7$ | phenyl | 1 | phenyl | 0 | F | H |
| 93 | $n\text{-}C_5H_{11}$ | phenyl | 1 | cyclohexyl | 0 | F | H |
| 94 | $n\text{-}C_7H_{15}$ | phenyl | 1 | phenyl | 0 | F | H |
| 95 | $CH_3OCH_2$ | phenyl | 1 | cyclohexyl | 0 | F | H |
| 96 | $CH_2=CH$ | phenyl | 1 | phenyl | 0 | H | H |

TABLE 10-continued

| No. | R | A1—Z1 | n1 | A2—Z2 | n2 | X1 | X2 |
|---|---|---|---|---|---|---|---|
| 97 | CH$_2$=CHCH$_2$CH$_2$ | phenyl | 1 | cyclohexyl | 0 | F | H |
| 98 | CH$_3$CH=CH—(CH$_2$)$_2$ | phenyl | 1 | phenyl | 0 | H | H |
| 99 | CH$_2$=CH—(CH$_2$)$_2$—CH=CH | phenyl | 1 | cyclohexyl | 0 | H | H |
| 100 | CH$_2$=CHCH$_2$O | phenyl | 1 | phenyl | 0 | F | H |

TABLE 11

| No. | R | A1—Z1 | n1 | A2—Z2 | n2 | A3—Z3 | X1 | X2 |
|---|---|---|---|---|---|---|---|---|
| 101 | CH$_3$ | cyclohexyl | 1 | cyclohexyl | 1 | phenyl | F | H |
| 102 | n-C$_3$H$_7$ | cyclohexyl | 1 | phenyl | 1 | phenyl | F | H |
| 103 | n-C$_5$H$_{11}$ | cyclohexyl | 1 | cyclohexyl | 1 | phenyl | F | F |
| 104 | n-C$_7$H$_{15}$ | cyclohexyl | 1 | phenyl | 1 | phenyl | F | H |
| 105 | CH$_3$OCH$_2$ | cyclohexyl | 1 | cyclohexyl | 1 | phenyl | F | H |
| 106 | CH$_2$=CH | cyclohexyl | 1 | phenyl | 1 | phenyl | H | H |
| 107 | CH$_2$=CHCH$_2$CH$_2$ | cyclohexyl | 1 | cyclohexyl | 1 | phenyl | F | H |

TABLE 11-continued

| No. | R | A1—Z1 | n1 | A2—Z2 | n2 | A3—Z3 | X1 | X2 |
|---|---|---|---|---|---|---|---|---|
| 108 | CH₃CH=CH—(CH₂)₂ | cyclohexyl | 1 | phenyl | 1 | phenyl | H | H |
| 109 | CH₂=CH—(CH₂)₂—CH=CH | cyclohexyl | 1 | cyclohexyl | 1 | phenyl | H | H |
| 110 | CH₂=CHCH₂O | cyclohexyl | 1 | phenyl | 1 | phenyl | F | H |

TABLE 12

| No. | R | A1—B1 | n1 | A2—Z2 | n2 | A3—Z3 | X1 | X2 |
|---|---|---|---|---|---|---|---|---|
| 111 | CH₃ | cyclohexyl | 1 | cyclohexyl | 1 | phenyl-CH₂CH₂- | F | H |
| 112 | n-C₃H₇ | cyclohexyl | 1 | phenyl | 1 | phenyl-CH₂CH₂- | F | H |
| 113 | n-C₅H₁₁ | cyclohexyl | 1 | cyclohexyl | 1 | phenyl-CH₂O- | F | F |
| 114 | n-C₇H₁₅ | cyclohexyl | 1 | phenyl | 1 | phenyl-OCH₂- | F | H |
| 115 | CH₃OCH₂ | cyclohexyl | 1 | cyclohexyl | 1 | phenyl-C≡C- | F | H |
| 116 | CH₂=CH | cyclohexyl | 1 | phenyl | 1 | phenyl-CH₂CH₂- | H | H |
| 117 | CH₂=CHCH₂CH₂ | cyclohexyl | 1 | cyclohexyl | 1 | phenyl-CH₂CH₂- | F | H |
| 118 | CH₃CH=CH—(CH₂)₂ | cyclohexyl | 1 | phenyl | 1 | phenyl-CH₂O- | H | H |

TABLE 12-continued

| No. | R | A1—B1 | n1 | A2—Z2 | n2 | A3—Z3 | X1 | X2 |
|---|---|---|---|---|---|---|---|---|
| 119 | $CH_3CH=CH-(CH_2)_2$ | cyclohexyl | 1 | cyclohexyl | 1 | phenyl-OCH$_2$ | H | H |
| 120 | $CH_2=CHCH_2O$ | cyclohexyl | 1 | phenyl | 1 | phenyl-C≡CH | F | H |

TABLE 13

| No. | R | A1—Z1 | n1 | A2—Z2 | n2 | A3—Z3 | X1 | X2 |
|---|---|---|---|---|---|---|---|---|
| 121 | $CH_3$ | cyclohexyl | 1 | cyclohexyl-CH$_2$CH$_2$ | 1 | phenyl | F | H |
| 122 | n-$C_3H_7$ | cyclohexyl | 1 | phenyl-CH$_2$CH$_2$ | 1 | phenyl | F | H |
| 123 | n-$C_5H_{11}$ | cyclohexyl | 1 | cyclohexyl-CH=CH | 1 | phenyl | F | F |
| 124 | n-$C_7H_{15}$ | cyclohexyl | 1 | phenyl-OCH$_2$ | 1 | phenyl | F | H |
| 125 | $CH_3OCH_2$ | cyclohexyl | 1 | cyclohexyl-OCH$_2$ | 1 | phenyl | F | H |
| 126 | $CH_2=CH$ | cyclohexyl | 1 | phenyl-CH$_2$O | 1 | phenyl | H | H |
| 127 | $CH_2=CHCH_2CH_2$ | cyclohexyl | 1 | cyclohexyl-CH$_2$O | 1 | phenyl | F | H |
| 128 | $CH_3CH=CH-(CH_2)_2$ | cyclohexyl | 1 | phenyl-C≡CH | 1 | phenyl | H | H |
| 129 | $CH_3CH=CH-(CH_2)_2$ | cyclohexyl | 1 | cyclohexyl-CH$_2$CH=CH | 1 | phenyl | H | H |
| 130 | $CH_2=CHCH_2O$ | cyclohexyl | 1 | phenyl-CH$_2$CH$_2$ | 1 | phenyl | F | H |

TABLE 14
| No. | R | A1—Z1 | n1 | A2—Z2 | n2 | A3—Z3 | X1 | X2 |
|---|---|---|---|---|---|---|---|---|
| 131 | $CH_3$ | 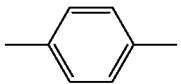 | 1 | 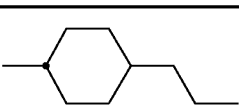 | 1 | 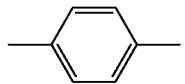 | F | H |
| 132 | $n-C_3H_7$ | 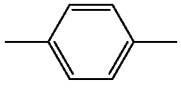 | 1 | 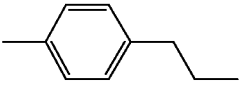 | 1 | 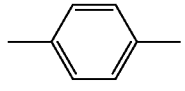 | F | H |
| 133 | $n-C_5H_{11}$ | 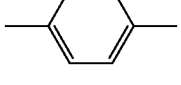 | 1 | 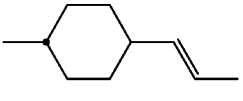 | 1 | 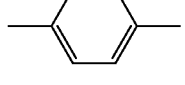 | F | F |
| 134 | $n-C_7H_{15}$ | 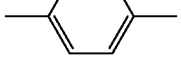 | 1 | 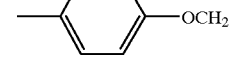 | 1 | 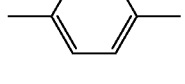 | F | H |
| 135 | $CH_3OCH_2$ | 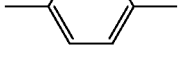 | 1 | 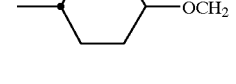 | 1 | 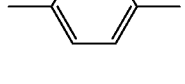 | F | H |
| 136 | $CH_2$=CH | 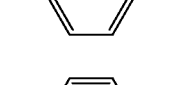 | 1 | 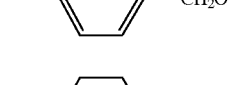 | 1 | 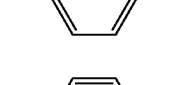 | H | H |
| 137 | $CH_2$=$CHCH_2CH_2$ | 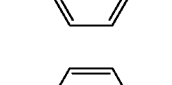 | 1 | 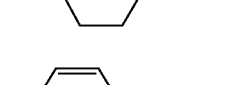 | 1 | 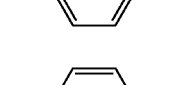 | F | H |
| 138 | $CH_3CH$=CH—$(CH_2)_2$ | 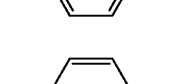 | 1 | 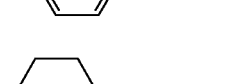 | 1 | 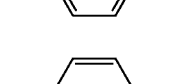 | H | H |
| 139 | $CH_3CH$=CH—$(CH_2)_2$ | 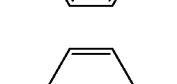 | 1 |  | 1 | 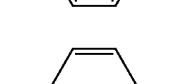 | H | H |
| 140 | $CH_2$=$CHCH_2O$ | 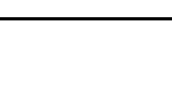 | 1 | 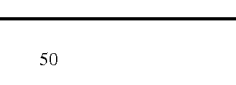 | 1 | 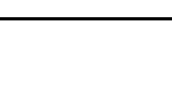 | F | H |
TABLE 15
| No. | R | A1-Z1 | n1 | n2 | X1 | X2 |
|---|---|---|---|---|---|---|
| 141 | $CH_3$ | 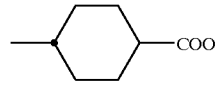 | 0 | 0 | F | H |

TABLE 15-continued

| No. | R | A1-Z1 | n1 | n2 | X1 | X2 |
|---|---|---|---|---|---|---|
| 142 | n-C$_3$H$_7$ | —⬡—COO | 0 | 0 | F | H |
| 143 | n-C$_5$H$_{11}$ | —⬡—COO | 0 | 0 | F | F |
| 144 | n-C$_7$H$_{15}$ | —⬡—COO | 0 | 0 | F | H |
| 145 | CH$_3$OCH$_2$ | —⬡—COO | 0 | 0 | F | H |
| 146 | CH$_2$=CH | —⬡—COO | 0 | 0 | H | H |
| 147 | CH$_2$=CHCH$_2$CH$_2$ | —⬡—COO | 0 | 0 | F | H |
| 148 | CH$_3$CH=CH—(CH$_2$)$_2$ | —⬡—COO | 0 | 0 | H | H |
| 149 | CH$_2$=CH—(CH$_2$)$_2$—CH=CH | —⬡—COO | 0 | 0 | H | H |
| 150 | CH$_2$=CHCH$_2$O | —⬡—COO | 0 | 0 | F | H |

TABLE 16

| No. | R | A1-Z1 | n1 | n2 | X1 | X2 |
|---|---|---|---|---|---|---|
| 151 | CH$_3$O | —⌬—COO | 0 | 0 | F | H |
| 152 | n-C$_3$H$_7$ | —⌬(F)—COO | 0 | 0 | F | H |

TABLE 16-continued

| No. | R | A1-Z1 | n1 | n2 | X1 | X2 | |
|---|---|---|---|---|---|---|---|
| 153 | n-C$_3$H$_7$ | —⟨phenyl⟩—COO | 0 | 0 | F | H | CN 76.5° C., NI 107.7° C. |
| 154 | n-C$_3$H$_7$ | —⟨phenyl⟩—COO | 0 | 0 | F | F | |
| 155 | C$_5$H$_{11}$ | —⟨phenyl⟩—COO | 0 | 0 | F | F | |
| 156 | CH$_2$=CH | —⟨phenyl⟩—COO | 0 | 0 | H | H | |
| 157 | CH$_2$=CHCH$_2$CH$_2$ | —⟨phenyl⟩—COO | 0 | 0 | F | H | |
| 158 | CH$_3$CH=CH—(CH$_2$)$_2$ | —⟨phenyl⟩—COO | 0 | 0 | H | H | |
| 159 | CH$_2$=CH—(CH$_2$)$_2$—CH=CH | —⟨phenyl⟩—COO | 0 | 0 | H | H | |
| 160 | CH$_2$=CHCH$_2$O | —⟨phenyl⟩—COO | 0 | 0 | F | H | |

TABLE 17

| No. | R | A1-Z1 | n1 | A2-Z2 | n2 | X1 | X2 | |
|---|---|---|---|---|---|---|---|---|
| 161 | CH$_3$ | —⟨cyclohexyl⟩— | 1 | —⟨cyclohexyl⟩—COO | 0 | F | H | |
| 162 | n-C$_3$H$_7$ | —⟨cyclohexyl⟩— | 1 | —⟨phenyl⟩—COO | 0 | F | H | CN 90.9° C., NI 254° C. (dec.) |
| 163 | n-C$_5$H$_{11}$ | —⟨cyclohexyl⟩— | 1 | —⟨cyclohexyl⟩—COO | 0 | F | H | |

TABLE 17-continued

| No. | R | A1-Z1 | n1 | A2-Z2 | n2 | X1 | X2 |
|---|---|---|---|---|---|---|---|
| 164 | n-C₇H₁₅ | cyclohexyl | 1 | phenyl-COO | 0 | F | H |
| 165 | CH₃OCH₂ | cyclohexyl | 1 | phenyl-COO | 0 | F | H |
| 166 | CH₂=CH | cyclohexyl | 1 | cyclohexyl-COO | 0 | H | H |
| 167 | CH₂=CHCH₂CH₂ | cyclohexyl | 1 | cyclohexyl-COO | 0 | F | H |
| 168 | CH₃CH=CH—(CH₂)₂ | cyclohexyl | 1 | cyclohexyl-COO | 0 | H | H |
| 169 | CH₂=CH—(CH₂)₂—CH=CH | cyclohexyl | 1 | cyclohexyl-COO | 0 | H | H |
| 170 | CH₂=CHCH₂O | cyclohexyl | 1 | cyclohexyl-COO | 0 | F | H |

TABLE 18

| No. | R | A1-Z1 | n1 | A2-Z2 | n2 | X1 | X2 |
|---|---|---|---|---|---|---|---|
| 170 | CH₃ | phenyl | 1 | cyclohexyl-COO | 0 | F | H |
| 171 | n-C₃H₇ | fluorophenyl | 1 | phenyl-COO | 0 | H | H |
| 172 | n-C₅H₁₁ | phenyl | 1 | cyclohexyl-COO | 0 | F | F |

TABLE 18-continued

| No. | R | A1-Z1 | n1 | A2-Z2 | n2 | X1 | X2 |
|---|---|---|---|---|---|---|---|
| 173 | n-C7H15 | (phenyl with F) | 1 | (phenyl-COO) | 0 | F | H |
| 174 | CH3OCH2 | (phenyl) | 1 | (phenyl-COO) | 0 | F | H |
| 175 | CH2=CH | (phenyl) | 1 | (cyclohexyl-COO) | 0 | H | H |
| 176 | CH2=CHCH2CH2 | (phenyl) | 1 | (cyclohexyl-COO) | 0 | F | H |
| 177 | CH3CH=CH—(CH2)2 | (phenyl) | 1 | (cyclohexyl-COO) | 0 | H | H |
| 178 | CH2=CH—(CH2)2—CH=CH | (phenyl) | 1 | (cyclohexyl-COO) | 0 | H | H |
| 180 | CH2=CHCH2O | (phenyl) | 1 | (phenyl-COO) | 0 | F | H |

TABLE 19

| No. | R | A1-Z1 | n1 | A1-Z2 | n2 | X1 | X2 |
|---|---|---|---|---|---|---|---|
| 181 | CH3 | (cyclohexyl-COO) | 1 | (cyclohexyl) | 0 | F | H |
| 182 | n-C3H7 | (phenyl-COO) | 1 | (cyclohexyl) | 0 | F | H |
| 183 | n-C5H11 | (cyclohexyl-COO) | 1 | (cyclohexyl) | 0 | F | H |
| 184 | n-C7H15 | (phenyl-COO) | 1 | (cyclohexyl) | 0 | F | H |

TABLE 19-continued

| No. | R | A1-Z1 | n1 | A1-Z2 | n2 | X1 | X2 |
|---|---|---|---|---|---|---|---|
| 185 | CH$_3$OCH$_2$ | —⟨phenyl⟩—COO | 1 | —⟨cyclohexyl⟩— | 0 | F | H |
| 186 | CH$_2$=CH | —⟨cyclohexyl⟩—COO | 1 | —⟨cyclohexyl⟩— | 0 | H | H |
| 187 | CH$_2$=CHCH$_2$CH$_2$ | —⟨cyclohexyl⟩—COO | 1 | —⟨cyclohexyl⟩— | 0 | F | H |
| 188 | CH$_3$CH=CH—(CH$_2$)$_2$ | —⟨cyclohexyl⟩—COO | 1 | —⟨cyclohexyl⟩— | 0 | H | H |
| 189 | CH$_2$=CH—(CH$_2$)$_2$—CH=CH | —⟨cyclohexyl⟩—COO | 1 | —⟨cyclohexyl⟩— | 0 | H | H |
| 190 | CH$_2$=CHCH$_2$O | —⟨phenyl⟩—COO | 1 | —⟨cyclohexyl⟩— | 0 | F | H |

TABLE 20

| No. | R | A1-Z1 | n1 | A1-Z2 | n2 | X1 | X2 |
|---|---|---|---|---|---|---|---|
| 191 | CH$_3$ | —⟨cyclohexyl⟩—COO | 1 | —⟨phenyl⟩— | 0 | F | H |
| 192 | n-C$_3$H$_7$ | —⟨phenyl⟩—COO | 1 | —⟨phenyl-F⟩— | 0 | H | H |

TABLE 20-continued

| No. | R | A1-Z1 | n1 | A1-Z2 | n2 | X1 | X2 |
|---|---|---|---|---|---|---|---|
| 193 | n-C$_5$H$_{11}$ | cyclohexyl-COO | 1 | phenyl | 0 | F | F |
| 194 | n-C$_7$H$_{15}$ | phenyl-COO | 1 | phenyl | 0 | F | H |
| 195 | CH$_3$OCH$_2$ | phenyl-COO | 1 | fluorophenyl (F) | 0 | F | F |
| 196 | CH$_2$=CH | cyclohexyl-COO | 1 | phenyl | 0 | H | H |
| 197 | CH$_2$=CHCH$_2$CH$_2$ | cyclohexyl-COO | 1 | phenyl | 0 | F | H |
| 198 | CH$_3$CH=CH—(CH$_2$)$_2$ | cyclohexyl-COO | 1 | phenyl | 0 | H | H |
| 199 | CH$_2$=CH—(CH$_2$)$_2$—CH=CH | cyclohexyl-COO | 1 | phenyl | 0 | H | H |
| 200 | CH$_2$=CHCH$_2$O | phenyl-COO | 1 | phenyl | 0 | F | H |

TABLE 21

| No. | R | A1-Z1 | n1 |
|---|---|---|---|
| 201 | CH$_3$ | —Cy—COO— | 1 |
| 202 | n-C$_3$H$_7$ | —Cy— | 1 |
| 203 | n-C$_5$H$_{11}$ | —Cy— | 1 |
| 204 | n-C$_7$H$_{15}$ | —Cy—COO— | 1 |
| 205 | CH$_3$OCH$_2$ | —Cy— | 1 |
| 206 | CH$_2$=CH | —Cy— | 1 |
| 207 | CH$_2$=CHCH$_2$CH$_2$ | —Cy—COO— | 1 |
| 208 | CH$_3$CH=CH—(CH$_2$)$_2$ | —Cy— | 1 |
| 209 | CH$_3$CH=CH—(CH$_2$)$_2$ | —Cy—(propyl) | 1 |
| 210 | CH$_2$=CHCH$_2$O | —Cy—COO— | 1 |

| No. | A2-Z2 | n2 | A3-Z3 | X1 | X2 |
|---|---|---|---|---|---|
| 201 | —Cy— | 1 | —Ph— | F | H |
| 202 | —Ph—COO— | 1 | —Ph— | F | H |
| 203 | —Cy— | 1 | —Ph—COO— | F | F |

TABLE 21-continued

| No. | A1-Z1 | n1 | A2-Z2 | X1 | X2 |
|---|---|---|---|---|---|
| 204 | propyl-phenyl | 1 | phenyl | F | H |
| 205 | cyclohexyl-COO | 1 | phenyl | F | H |
| 206 | phenyl | 1 | 2-F-phenyl-COO | H | H |
| 207 | cyclohexyl | 1 | phenyl | F | H |
| 208 | phenyl-COO | 1 | phenyl | H | H |
| 209 | cyclohexyl | 1 | phenyl-COO | H | H |
| 210 | phenyl | 1 | phenyl | F | H |

TABLE 22

| No. | R | A1–Z1 | n1 | A2—Z2 | n2 | A3–Z3 | X1 | X2 |
|---|---|---|---|---|---|---|---|---|
| 211 | $CH_3$ | phenyl-COO | 1 | cyclohexyl | 1 | phenyl | F | H |
| 212 | n-$C_3H_7$ | phenyl | 1 | phenyl-COO | 1 | phenyl | F | H |
| 213 | n-$C_5H_{11}$ | propyl-phenyl | 1 | cyclohexyl | 1 | phenyl-COO | F | F |
| 214 | n-$C_7H_{15}$ | phenyl-COO | 1 | phenyl | 1 | phenyl | F | H |

TABLE 22-continued

| No. | R | A1–Z1 | n1 | A2—Z2 | n2 | A3–Z3 | X1 | X2 |
|---|---|---|---|---|---|---|---|---|
| 215 | CH₃OCH₂ | phenyl | 1 | cyclohexyl-COO | 1 | pyridyl | F | H |
| 216 | CH₂=CH | phenyl-propyl | 1 | phenyl | 1 | fluorophenyl-COO | H | H |
| 217 | CH₂=CHCH₂ | phenyl-COO | 1 | cyclohexyl | 1 | pyridyl | F | H |
| 218 | CH₃CH=CH—(CH₂)₂ | phenyl | 1 | phenyl-COO | 1 | pyridyl | H | H |
| 219 | CH₃CH=CH—(CH₂)₂ | phenyl | 1 | cyclohexyl | 1 | phenyl-COO | H | H |
| 220 | CH₂=CHCH₂O | phenyl-COO | 1 | phenyl-propyl | 1 | pyridyl | F | H |

TABLE 23

| No. | R | A1–Z1 | n1 | n2 | X1 | X2 |
|---|---|---|---|---|---|---|
| 221 | CH₃ | 1,3-dioxanyl | 0 | 0 | F | H |
| 222 | n-C₃H₇ | pyrimidinyl | 0 | 0 | F | H |
| 223 | n-C₅H₁₁ | 1,3-dioxanyl | 0 | 0 | F | F |
| 224 | n-C₇H₁₅ | 1,3-dioxanyl | 0 | 0 | F | H |
| 225 | CH₃OCH₂ | pyrimidinyl | 0 | 0 | F | H |

TABLE 23-continued
| No. | R | A1-Z1 | n1 | n2 | X1 | X2 |
|---|---|---|---|---|---|---|
| 226 | CH$_2$=CH | 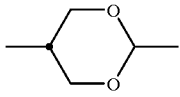 | 0 | 0 | H | H |
| 227 | CH$_2$=CHCH$_2$CH$_2$ | 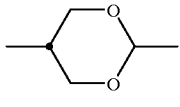 | 0 | 0 | F | H |
| 228 | CH$_3$CH=CH—(CH$_2$)$_2$ | 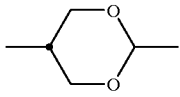 | 0 | 0 | H | H |
| 229 | CH$_2$=CH—(CH$_2$)$_2$—CH=CH | 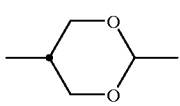 | 0 | 0 | H | H |
| 230 | CH$_2$=CHCH$_2$O | 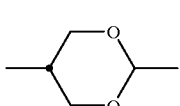 | 0 | 0 | F | H |
TABLE 24
| No. | R | A1-Z1 | n1 | A2-Z2 | n2 | A3-Z3 | X1 | X2 |
|---|---|---|---|---|---|---|---|---|
| 231 | CF$_3$ |  | 0 | — | 0 | — | F | H |
| 232 | n-C$_3$F$_7$ |  | 0 | — | 0 | — | H | H |
| 233 | CFH$_2$O |  | 1 | 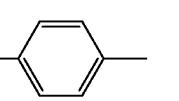 | 0 | — | F | F |
| 234 | CF$_2$HCH$_2$CH$_2$ | 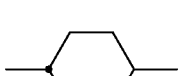 | 1 | 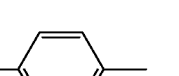 | 0 | — | F | H |
| 235 | CF$_3$OCH$_2$ | 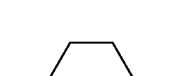 | 1 | 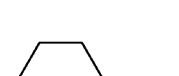 | 0 | — | F | H |
| 236 | CF$_2$=CH | 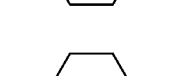 | 0 | — | 0 | — | H | H |

TABLE 24-continued

| No. | R | A1–Z1 | n1 | A2–Z2 | n2 | A3–Z3 | X1 | X2 |
|---|---|---|---|---|---|---|---|---|
| 237 | $CF_2=CHCH_2CH_2$ | ⌬— | 1 | ⌬— | 0 | — | F | H |
| 238 | $CF_3$ | ⌬— | 1 | ⏣— | 0 | — | H | H |
| 239 | $CF_2HCH_2$ | ⌬— | 1 | ⏣— | 0 | — | H | H |
| 240 | $CF_3CH_2CH_2O$ | ⌬— | 1 | ⏣—CH$_2$CH$_2$— | 1 | ⏣— | F | H |

The liquid crystal composition of the present invention comprises at least two ingredients containing at least one of the propiolonitrile derivatives of formula (1). The second ingredient may be different species of the propiolonitrile derivatives, but preferably at least one of other liquid crystalline compounds than the present propiolonitrile derivatives. It is preferable for producing excellent characteristics that the liquid crystal composition contains 0.1 to 99.9% by weight of the propiolonitrile derivative.

More specifically, the liquid crystal composition of the present invention comprises as a first ingredient, at least one of the propiolonitrile derivatives of formula (1) and as a second ingredient, at least one of the compounds of formula (2) and/or at least one of the compounds of formula (3).

The compounds of formula (2) are more specifically the liquid crystalline compounds of the following formulas (2a), (2b) and (2c) wherein a, Z4, Z5, $R_1$, X5 and (F) have the same meaning as defined above.

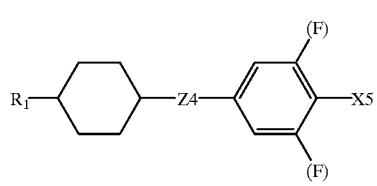

(2a)

(2b)

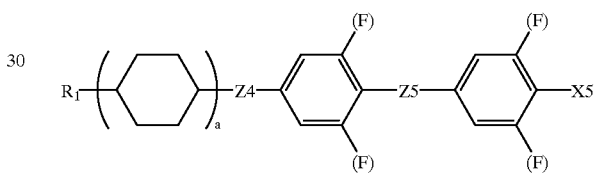

(2c)

Suitable examples of the compounds included in formulas (2a), (2b) and (2c) can include those of the following formulas (2a-1) to (2a-15), (2b-1) to (2b-48) and (2c-1) to (2c-55) in which $R_1$ has the same meaning as defined above.

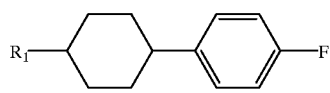

(2a-1)

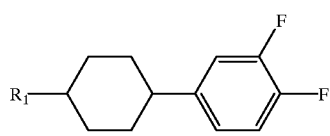

(2a-2)

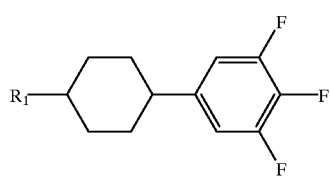

(2a-3)

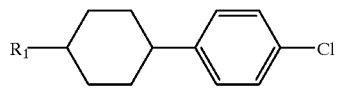

(2a-4)

-continued
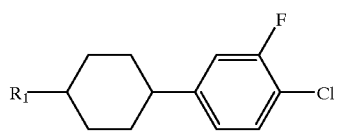 (2a-5)
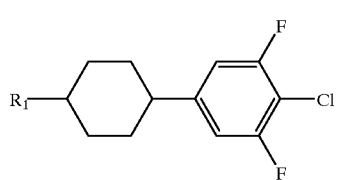 (2a-6)
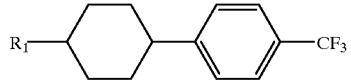 (2a-7)
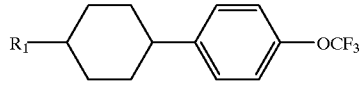 (2a-8)
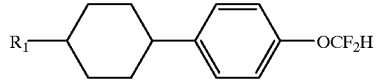 (2a-9)
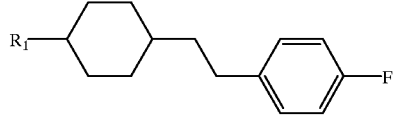 (2a-10)
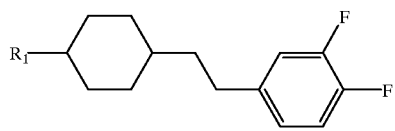 (2a-11)
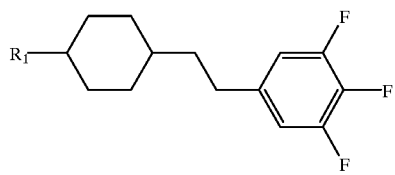 (2a-12)
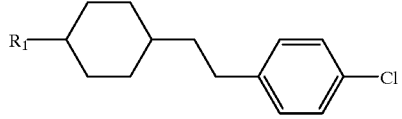 (2a-13)
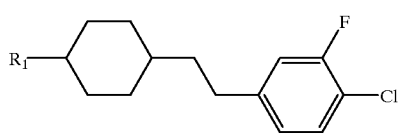 (2a-14)
-continued
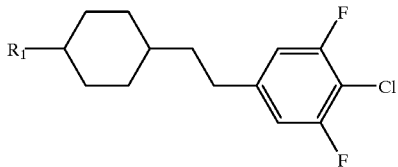 (2a-15)
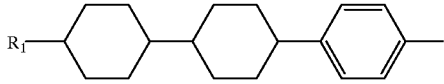 (2b-1)
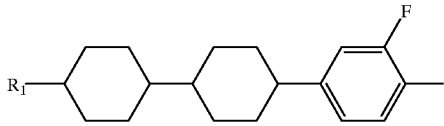 (2b-2)
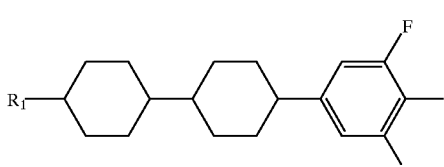 (2b-3)
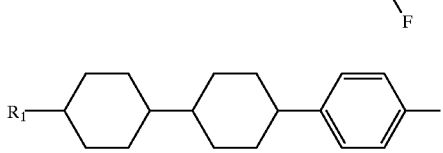 (2b-4)
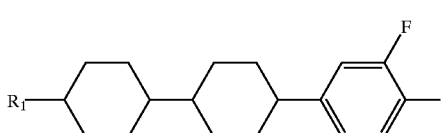 (2b-5)
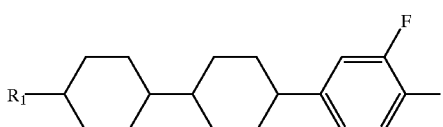 (2b-6)
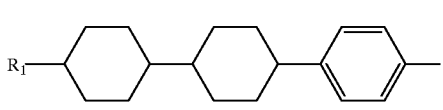 (2b-7)
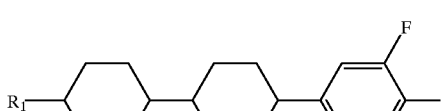 (2b-8)
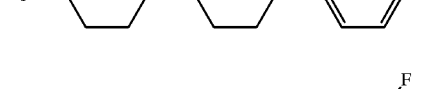 (2b-9)

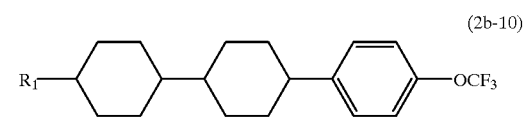
(2b-10)
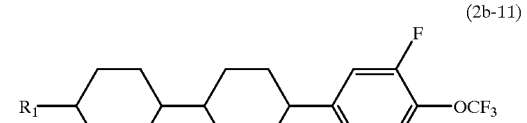
(2b-11)
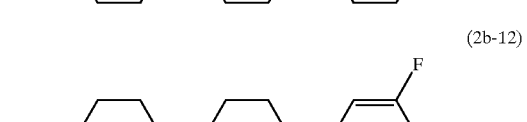
(2b-12)
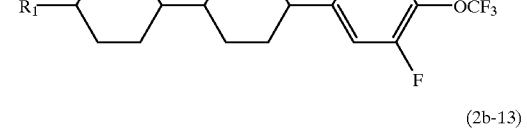
(2b-13)
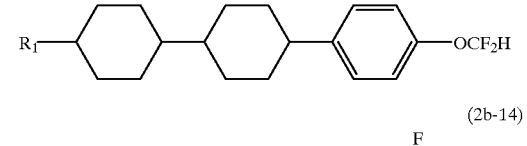
(2b-14)
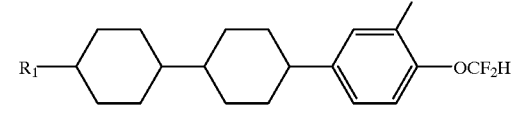
(2b-15)
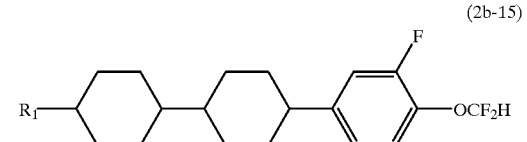
(2b-16)
(2b-17)
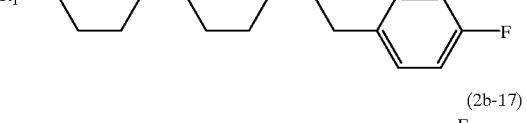
(2b-18)
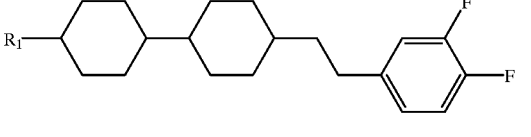
(2b-19)
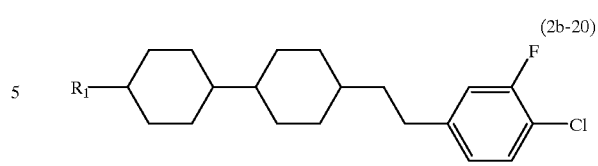
(2b-20)
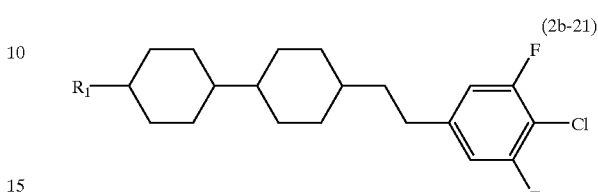
(2b-21)
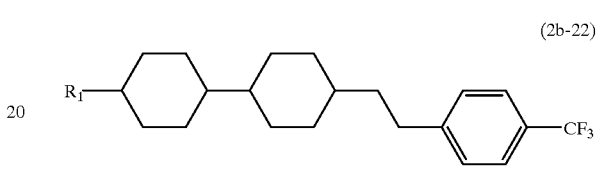
(2b-22)
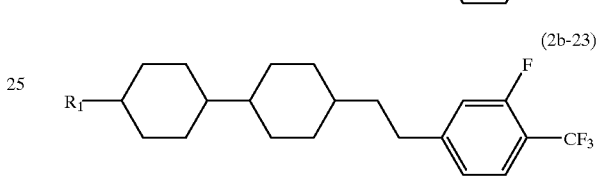
(2b-23)
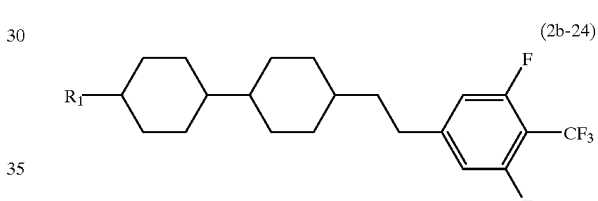
(2b-24)
(2b-25)
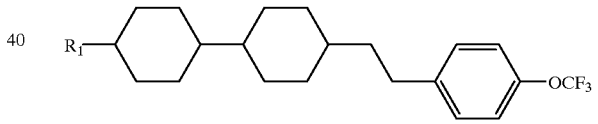
(2b-25)
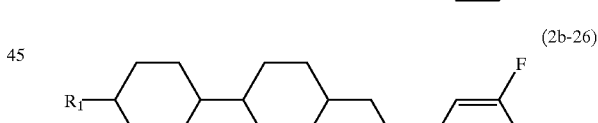
(2b-26)
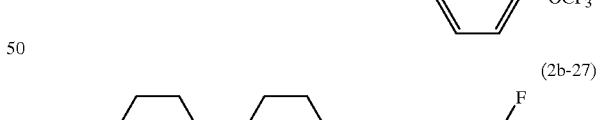
(2b-27)
(2b-28)

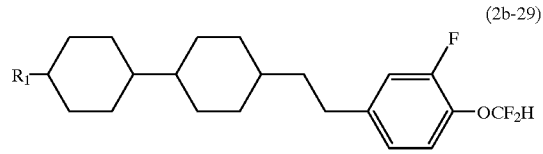
(2b-29)
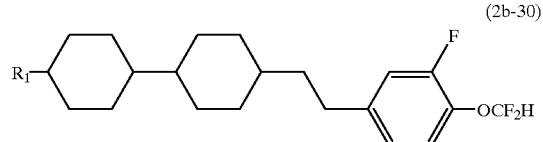
(2b-30)
(2b-31)
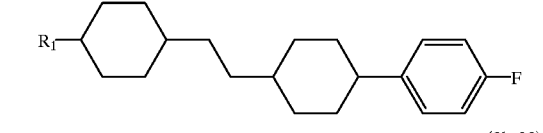
(2b-32)
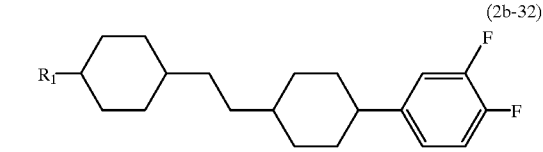
(2b-33)
(2b-34)
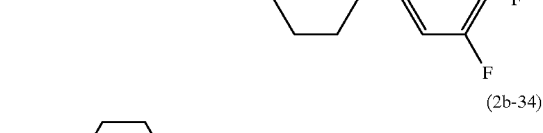
(2b-35)
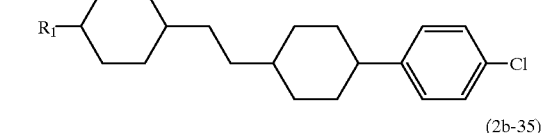
(2b-36)
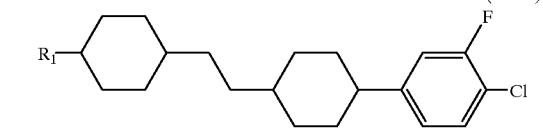
(2b-37)
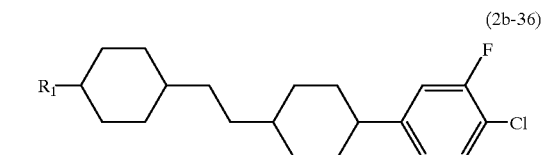
(2b-38)
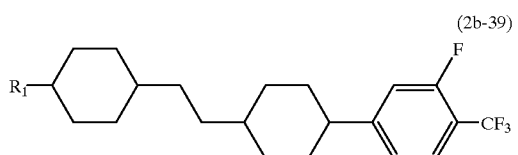
(2b-39)
(2b-40)
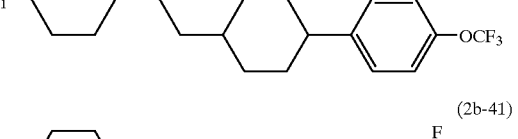
(2b-41)
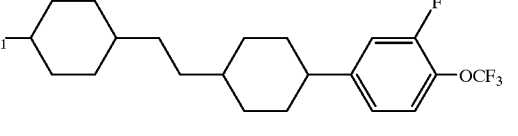
(2b-42)
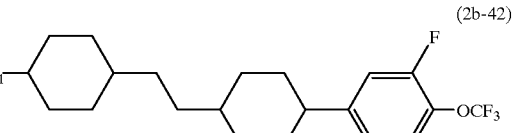
(2b-43)
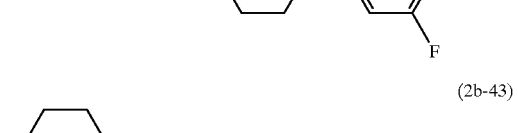
(2b-44)
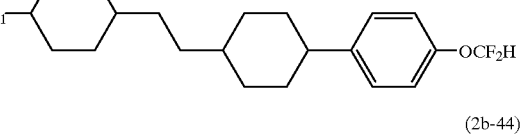
(2b-45)
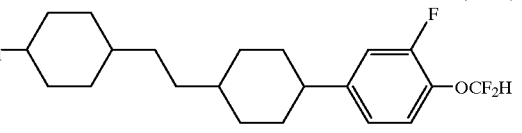
(2b-46)
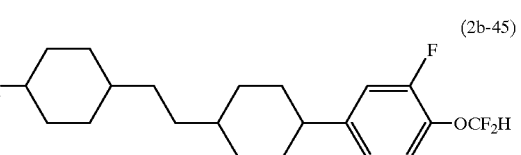
(2b-47)

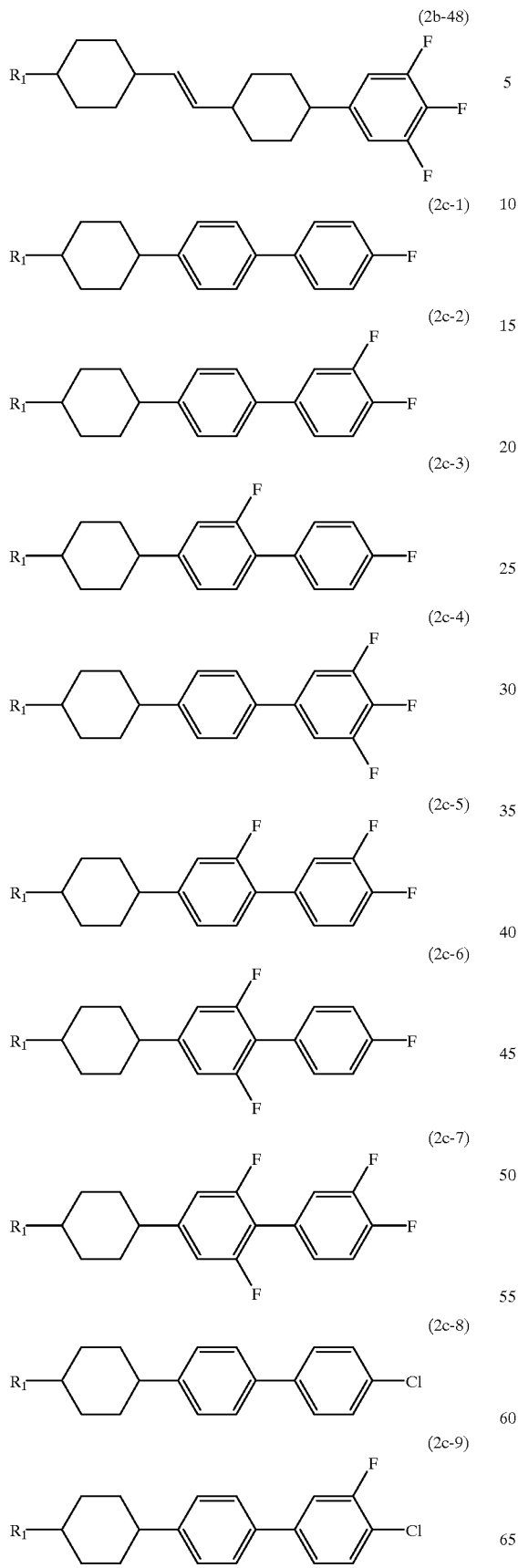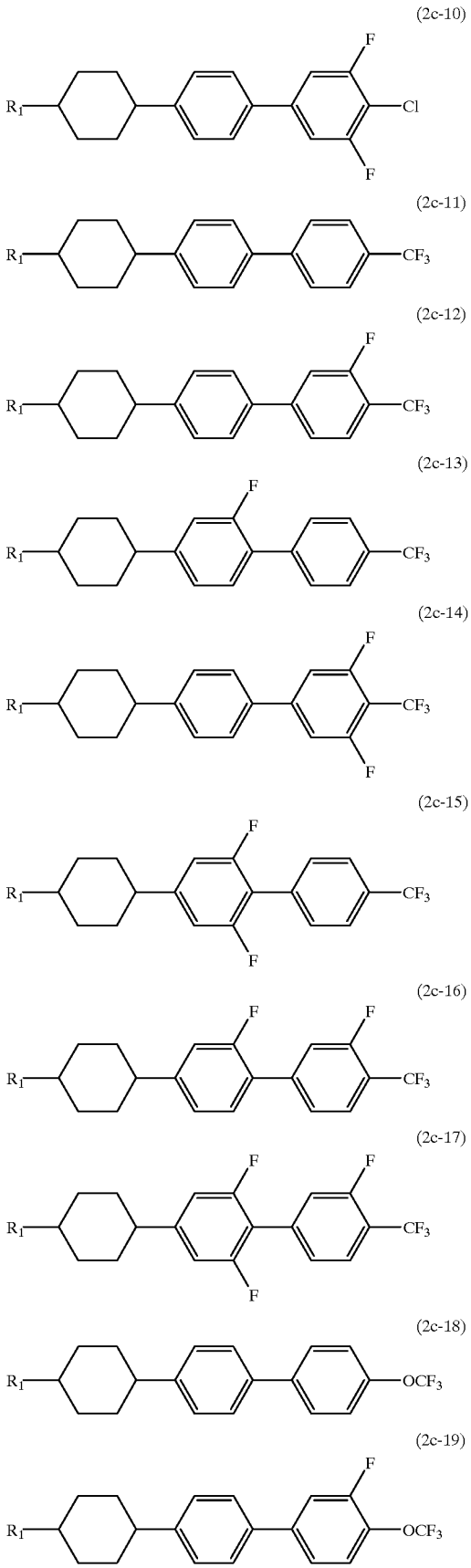

-continued
(2c-20)
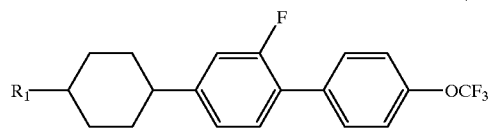
(2c-21)
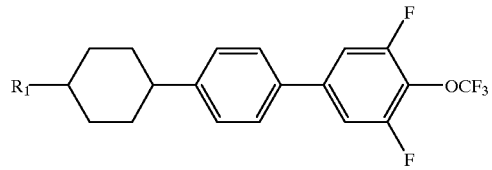
(2c-22)
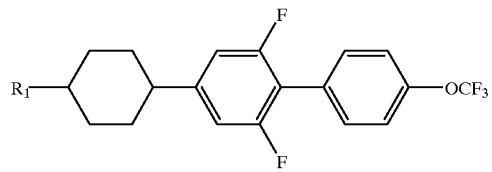
(2c-23)
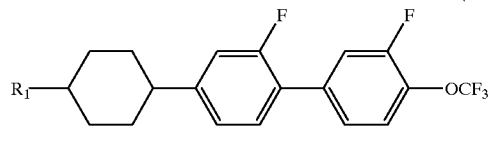
(2c-24)
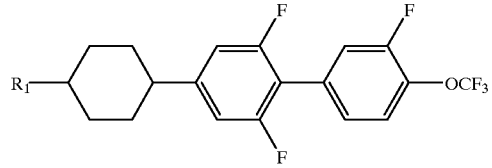
(2c-25)
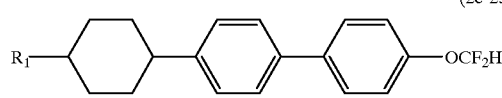
(2c-26)
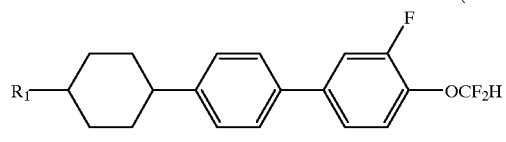
(2c-27)
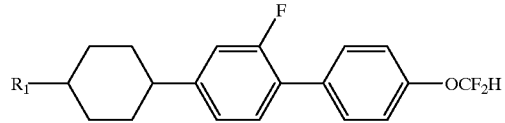
(2c-28)
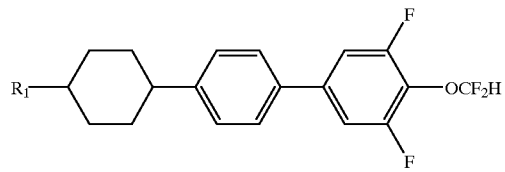
-continued
(2c-29)
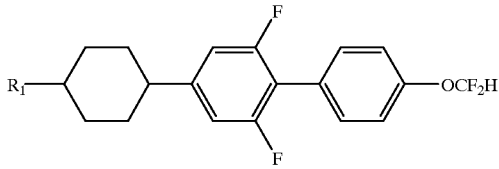
(2c-30)
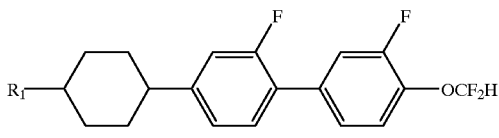
(2c-31)
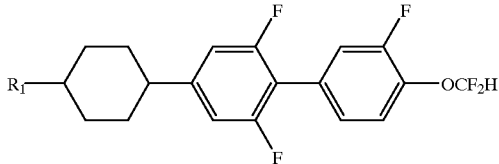
(2c-32)
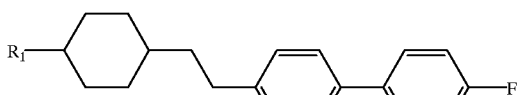
(2c-33)
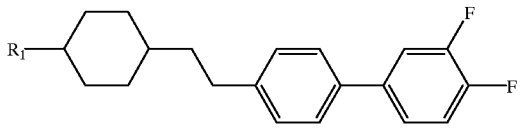
(2c-34)
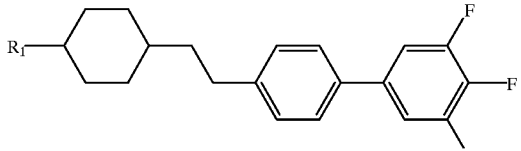
(2c-35)
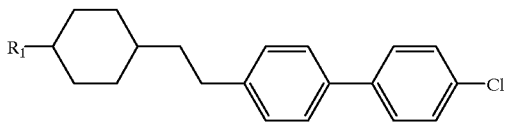
(2c-36)
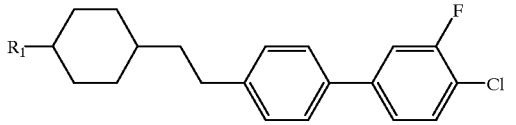
(2c-37)
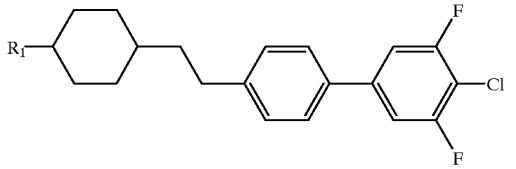

(2c-38) 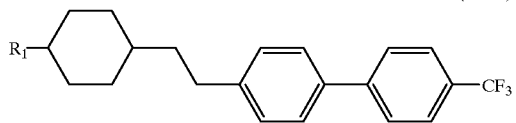
(2c-39) 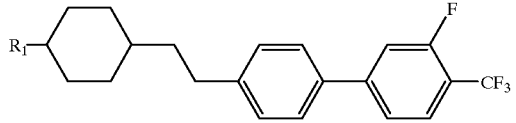
(2c-40) 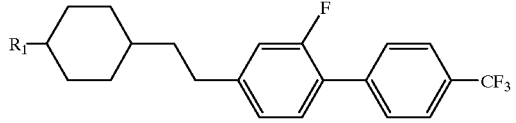
(2c-41) 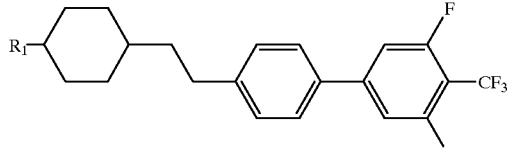
(2c-42) 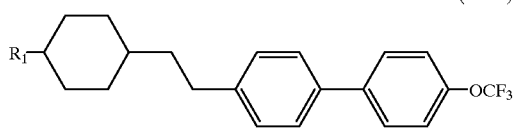
(2c-43) 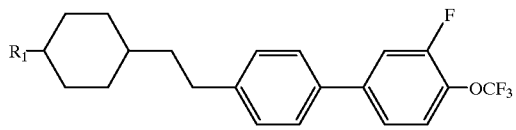
(2c-44) 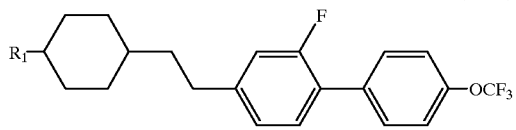
(2c-45) 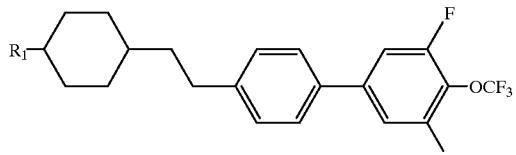
(2c-46) 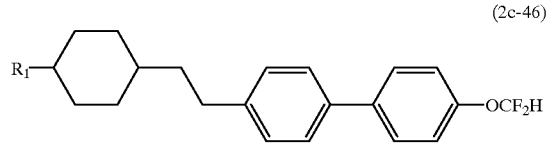
(2c-47) 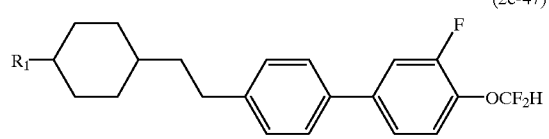
(2c-48) 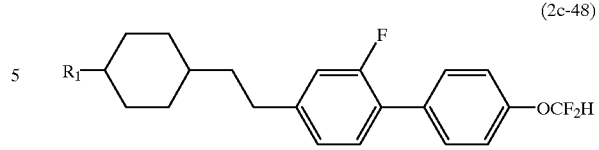
(2c-49) 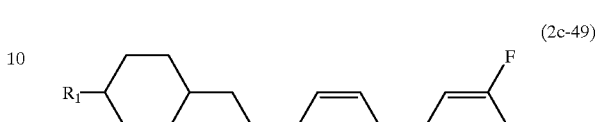
(2c-50) 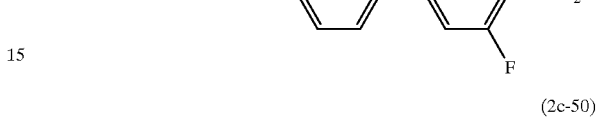
(2c-51) 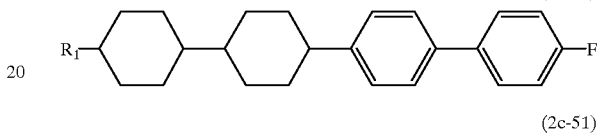
(2c-52) 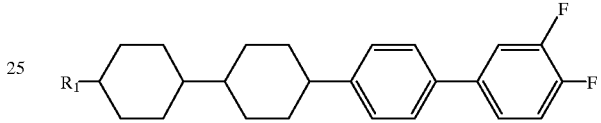
(2c-53) 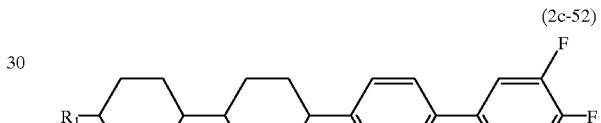
(2c-54) 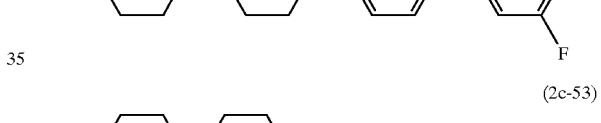
(2c-55) 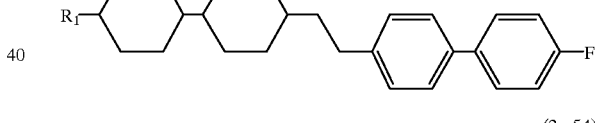
The compounds of formulas (2a) to (2c) exhibit a positive dielectric anisotropy, have very good heat and chemical stability.
More specific example of the compounds of formula (3) can include those of the following formulas (3a), (3b), (3c), (3d) and (3e).

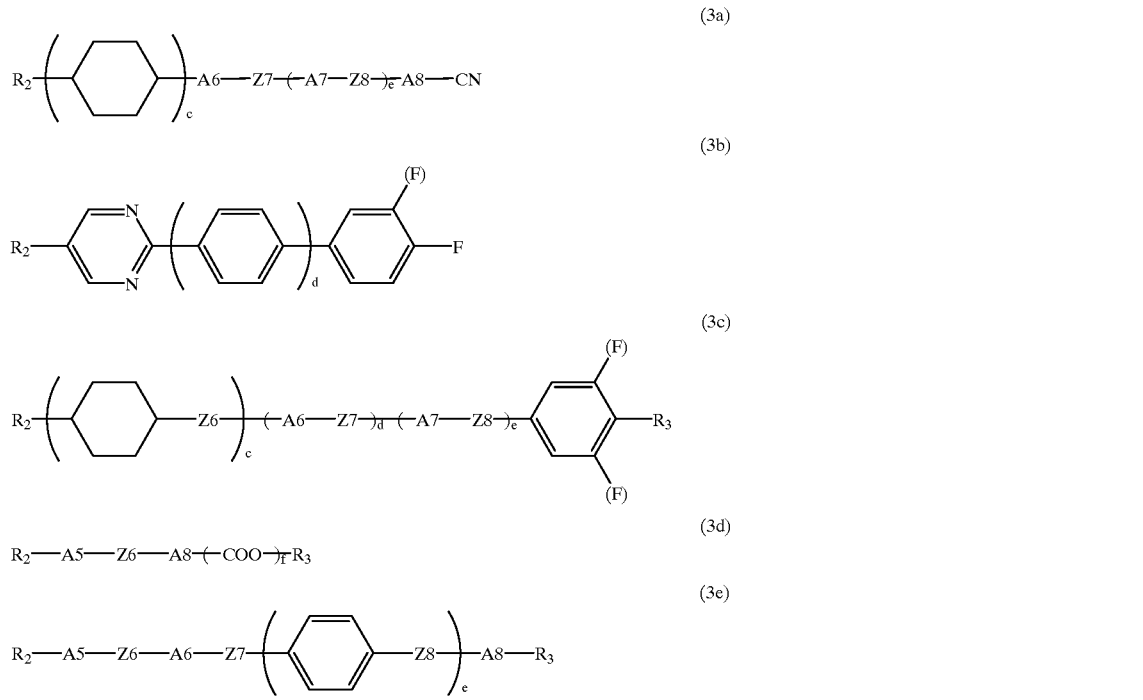

In formula (3a), c and e is 0 or 1, A8 represents 1,4-phenylene wherein the carbon atom at the 3- and/or 5-position (the carbon atom to which the terminal group CN is attached being at the 4-position) may be substituted by a fluorine atom or a trans-1,4-cyclohexylene, A6 represents a trans-1,4-cyclohexylene, 1,4-phenylene or 1,3-dioxane-2,5-diyl, A7 represents a trans-1,4-cyclohexylene, 1,4-phenylene or 1,3-pyrimidine-2,5-diyl, Z7 and Z8 each independently represent ethylene, carbonyloxy or a single bond, $R_2$ represents a saturated aliphatic hydrocarbyl radical of 1–10 carbons optionally having one or more ether linkages (—O—) in the chain or an unsaturated aliphatic hydrocarbyl radical of 2–10 carbons optionally having an ethenylene group in the terminal vinyl group and/or the chain and optionally having one or more ether linkages (—O—) in the chain. More specific examples of the compounds of formula (3a) can include those of the following formulas (3a-1) to (3a-24) in which R2 has the same meaning as defined above.

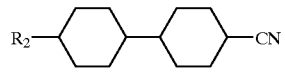
(3a-1)

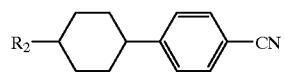
(3a-2)

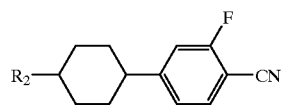
(3a-3)

-continued

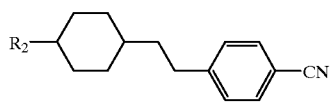
(3a-4)

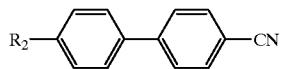
(3a-5)

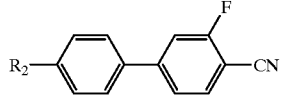
(3a-6)

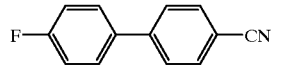
(3a-7)

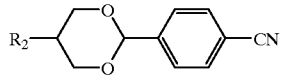
(3a-8)

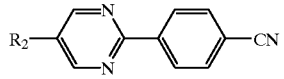
(3a-9)

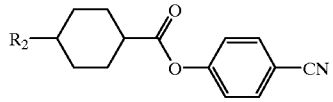
(3a-10)

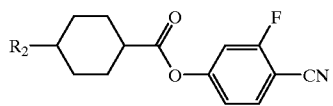
(3a-11)

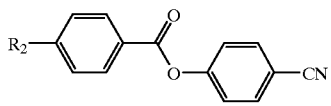 (3a-12)

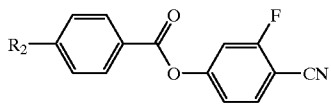 (3a-13)

 (3a-14)

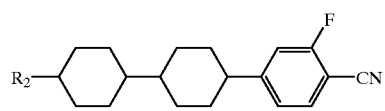 (3a-15)

 (3a-16)

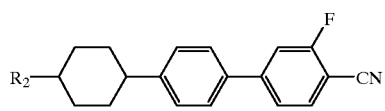 (3a-17)

 (3a-18)

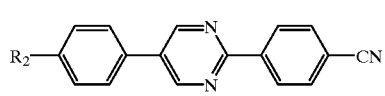 (3a-19)

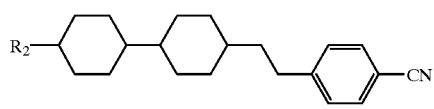 (3a-20)

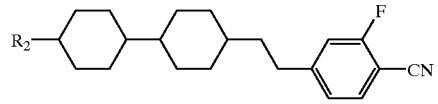 (3a-21)

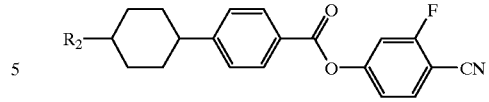 (3a-22)

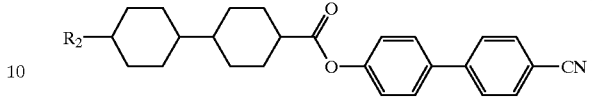 (3a-23)

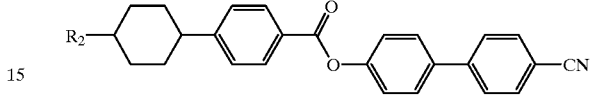 (3a-24)

In formula (3b), d is 0 or 1, $R_2$ is alkyl of 1–10 carbons and (F) stands for the case where the phenyl ring may be substituted by a fluorine atom. More specific examples of the compounds of formula (3b) are represented by the following formulas (3b-1) to (3b-3) in which R2 has the same meaning as defined above.

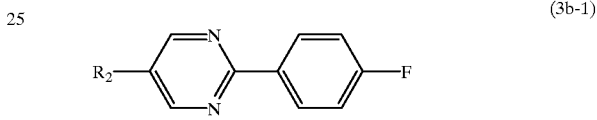 (3b-1)

 (3b-2)

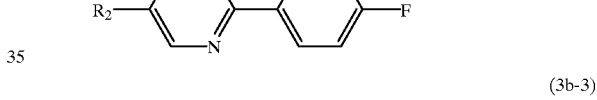 (3b-3)

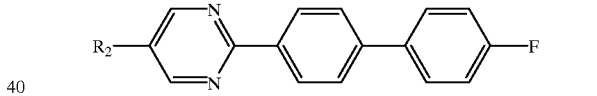

In formula (3c), c, d and e is 0 or 1 but the total of c, d and e (c+d+e) is at least 1, A6 and A7 each independently represent a trans-1,4-cyclohexylene or 1,4-phenylene, Z6 and Z7 each independently represent carbonyloxy or a single bond, Z8 represents carbonyloxy or ethynylene, $R_2$ represents alkyl of 1–10 carbons, $R_3$ represents F, —$OCF_3$, —$OCHF_2$, —$CF_3$ or —$CFH_2$ and (F) stands for the case where the phenyl group may be substituted by a fluorine atom. When $R_3$ represents —$OCF_3$, —$OCHF_2$, —$CF_3$ or —$CFH_2$, at least one of (F) is a fluorine atom. More specific examples of the compounds of formula (3c) are represented by the following formulas (3c-1) to (3c-28) in which $R_2$ has the same meaning as defined above.

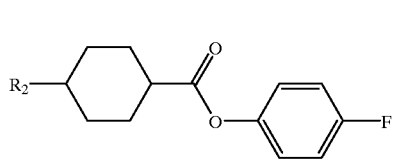 (3c-1)

-continued
(3c-2)
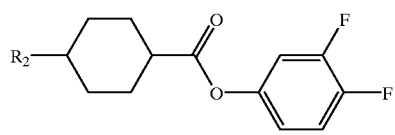
(3c-3)
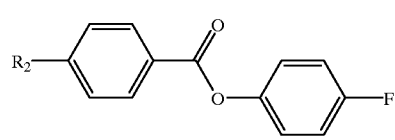
(3c-4)
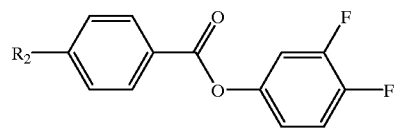
(3c-5)
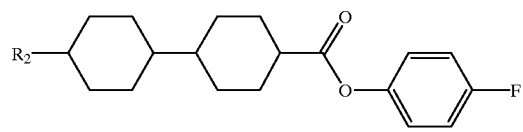
(3c-6)
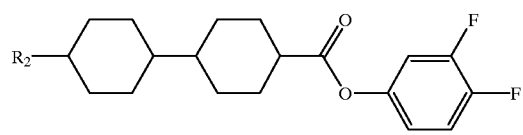
(3c-7)
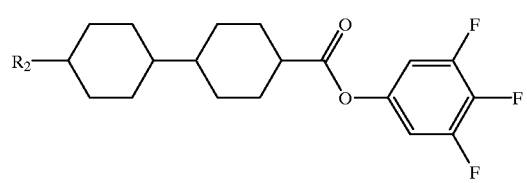
(3c-8)
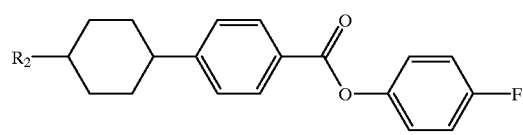
(3c-9)
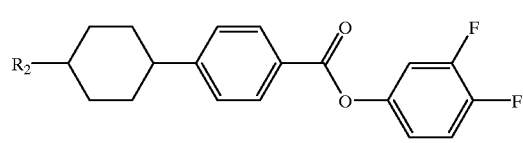
(3c-10)
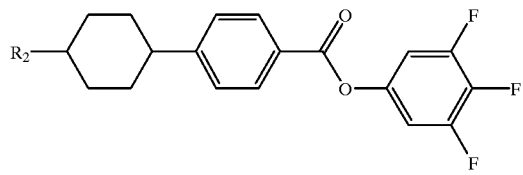
(3c-11)
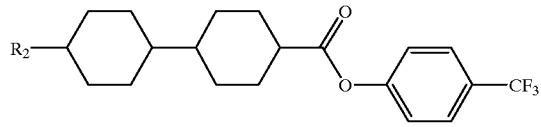

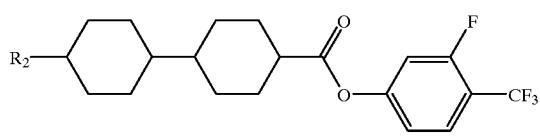
(3c-12)
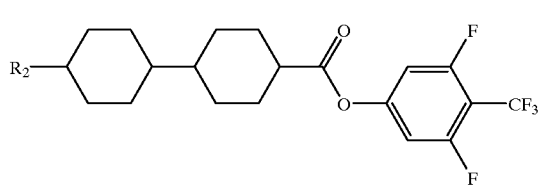
(3c-13)
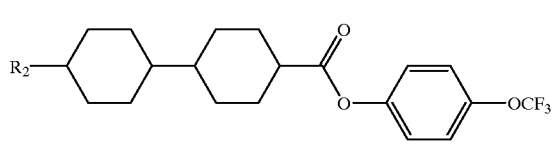
(3c-14)
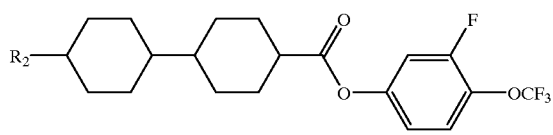
(3c-15)
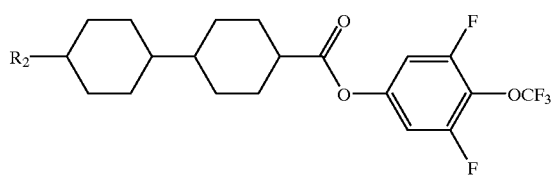
(3c-16)
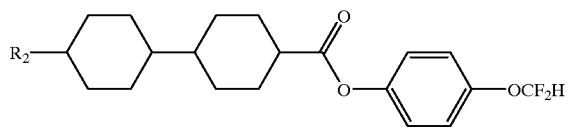
(3c-17)
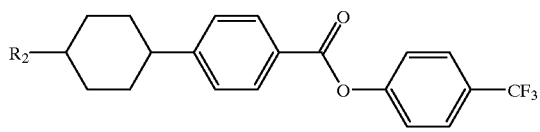
(3c-18)
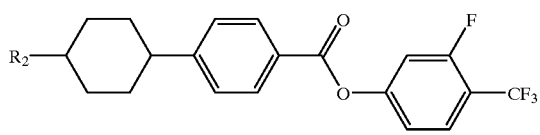
(3c-19)
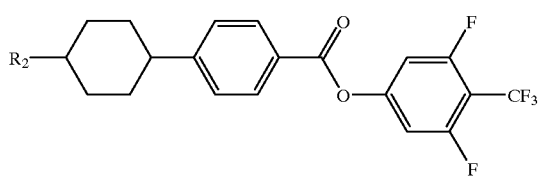
(3c-20)

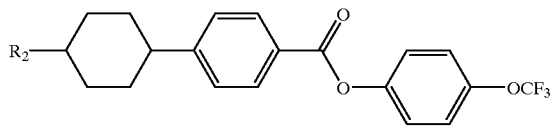
(3c-21)

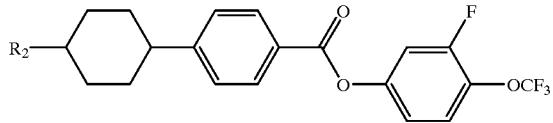
(3c-22)

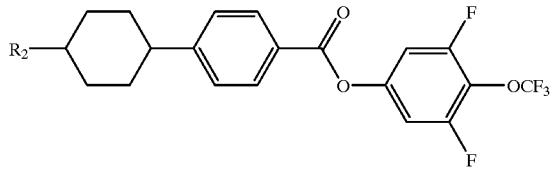
(3c-23)

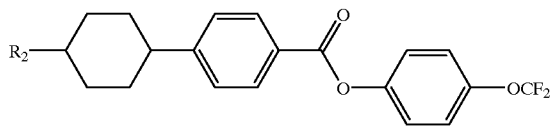
(3c-24)

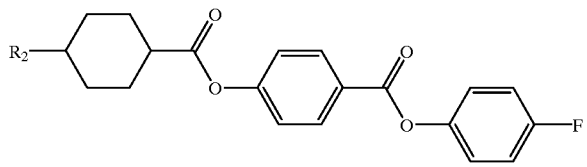
(3c-25)

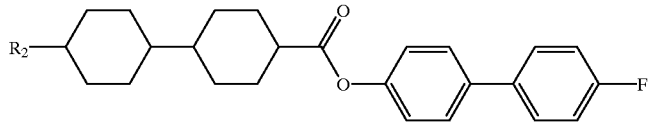
(3c-26)

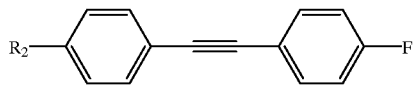
(3c-27)

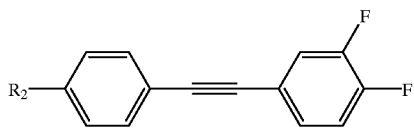
(3c-28)

In formula (3d), f is 0 or 1, A5 represents a trans-1,4-cyclohexylene, 1,3-pyrimidine-2,5-diyl or 1,4-phenylene, A8 represents a trans-1,4-cyclohexylene or 1,4-phenylene, Z6 represents ethynylene, carbonyloxy, ethylene, 1,2-ethynylene-3,4-ethenylene or a single bond, and $R_2$ and $R_3$ each independently represent a saturated aliphatic hydrocarbyl radical of 1-10 carbons optionally having one or more ether linkages (—O—) in the chain or an unsaturated aliphatic hydrocarbyl radical of 2–10 carbons optionally having an ethenylene group in the terminal vinyl group and/or the chain and optionally having one or more ether linkages (—O—) in the chain. More specific compounds of formula (3d) are represented by the following formulas (3d-1) to (3d-8) in which $R_2$ has the same meaning as defined above.

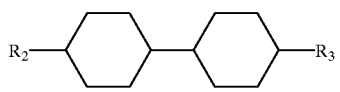
(3d-1)

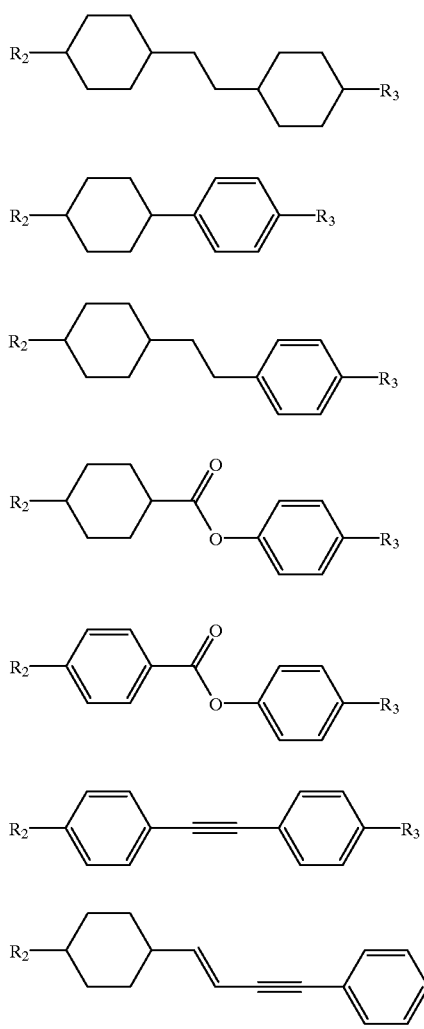

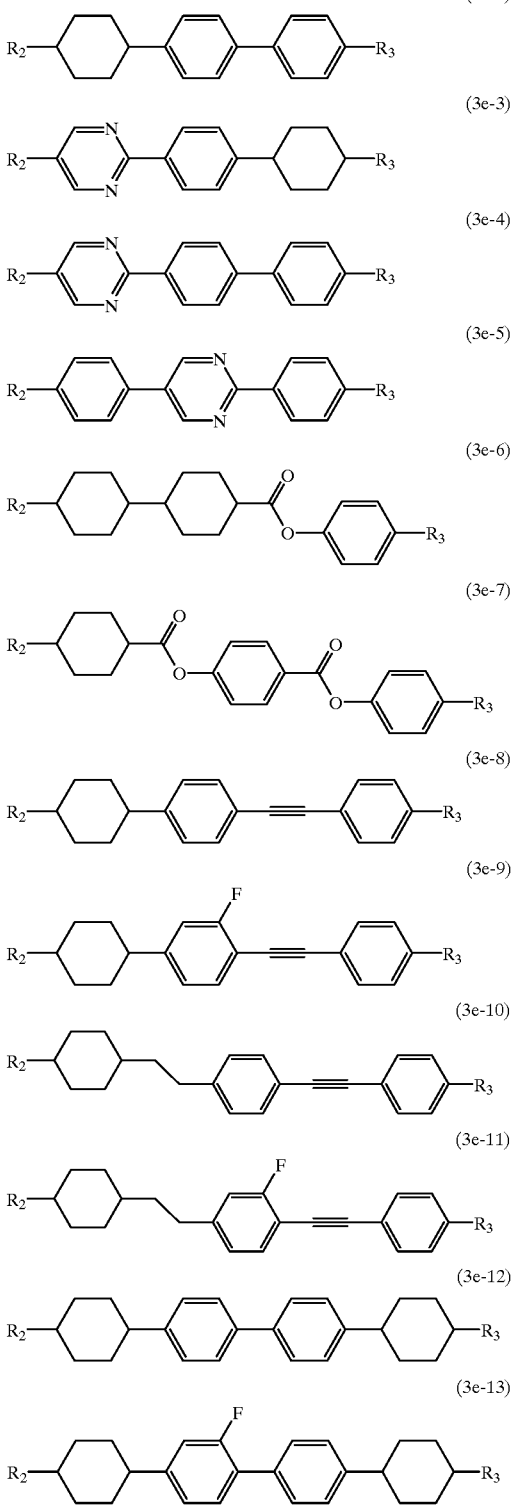

In formula (3e), e is 0 or 1, A5 represents a trans-1,4-cyclohexylene, 1,4-phenylene or 1,3-pyrimidine-2,5-diyl, A6 represents a trans-1,4-cyclohexylene, 1,4-phenylene which may be substituted by one or more fluorine atoms or 1,3-pyrimidine-2,5-diyl, A8 represents a trans-1,4-cyclohexylene or 1,4-phenylene, Z6 and Z8 each independently represent carbonyloxy, ethylene or a single bond, Z7 represents ethenylene, ethynylene, carbonyloxy or a single bond, and $R_2$ and $R_3$ each independently represent a saturated aliphatic hydrocarbyl radical of 1–10 carbons optionally having one or more ether linkages (—O—) in the chain or an unsaturated aliphatic hydrocarbyl radical of 2–10 carbons optionally having an ethenylene group in the terminal vinyl group and/or the chain and optionally having one or more ether linkages (—O—) in the chain. More specific compounds of formula (3e) are represented by the following formulas (3e-1) to (3e-13) in which $R_2$ has the same meaning as defined above.

(3e-1)

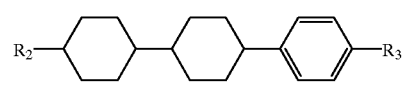

The compounds of formulas (3a) to (3c) have a positive and high dielectric anisotropy and are used as the ingredient of the liquid crystal composition especially for the purpose of reducing a threshold voltage. Further, those compounds are used for the purpose of adjusting the viscosity and optical anistropy of the composition and broadening the temperature range of liquid crystal phase and improving the steepness.

The compounds of formulas (3d) and (3e) are those in which the dielectric anisotropy is negative or a little positive. In particular, the compounds of formula (3d) are used mainly for the purpose of lowering the viscosity and/or adjusting the optical anistropy. The compounds of formula (3e) are used for the purpose of broadening the nematic range such as increasing the clearing point and/or adjusting the optical anisotropy. Those compounds are essential for the preparation of the liquid crystal compositions for the STN and usual TN display modes.

The liquid crystal composition of the present invention contains 0.1 to 99.9% by weight, based on the total weight of the composition, of at least one of the propiolonitrile derivatives of formula (1) and 1 to 99% by weight, preferably 10 to 97% and more preferably 40 to 95% by weight of at least one of the compounds of formula (2).

Another liquid crystal composition of the invention, for instance, for conventional TN and STN display modes, contains 0.1 to 99.9% by weight, based on the total weight of the composition, of at least one of the propiolonitrile derivatives of formula (1) and 1 to 99% by weight, preferably 10 to 97% and more preferably 40 to 95% by weight of at least one of the compounds of formula (3). In this composition, the compound of formula (3) may be partially replaced by that of formula (2).

The liquid crystal compositions of the invention can contain known compounds as a third ingredient for the purpose of adjusting the threshold voltage, temperature range of liquid crystal phase, optical anistropy and viscosity, etc.

The use of the present liquid crystal compositions in the TFT liquid crystal display elements can improve the steepness and an angle of view. The compounds of formula (1) have low viscosity and so the response rate of the liquid crystal display element is greatly improved by using said compounds.

The liquid crystal compositions of the present invention are prepared by conventional methods. In general, there is employed a method wherein different ingredients are dissolved in each other at an elevated temperature, but they may be dissolved in an organic solvent capable of dissolving a liquid crystal dissolve and mixed, and the solvent may be distilled away under reduced pressure.

In case where the present liquid crystal compositions are used as the liquid crystal materials for display element, they are improved and optimized with any suitable additives, depending on the intended applications. Such additives are well known to a person skilled in the art and described in detail in the literatures.

In general, an optically active compound, e.g. the below-recited compounds (C-1) to (C-8) may be added as a chiral dopant to the composition to induce a helical structure of the liquid crystal, thus adjusting a required twist angle and preventing a reverse twist.

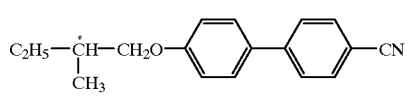
(C-1)

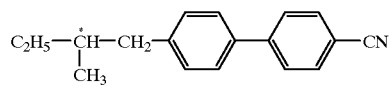
(C-2)

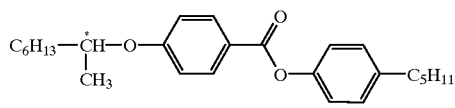
(C-3)

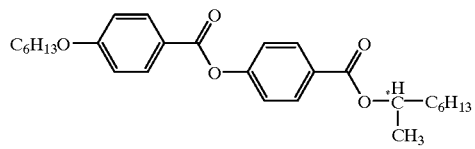
(C-4)

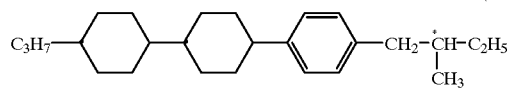
(C-5)

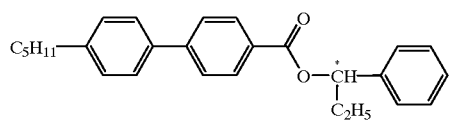
(C-6)

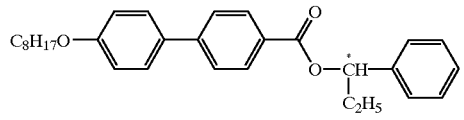
(C-7)

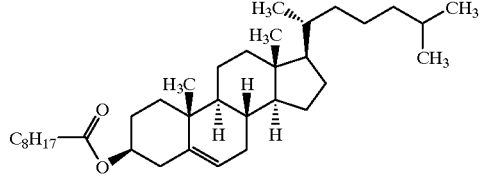
(C-8)

For example, the liquid crystal compositions of the invention can be used as liquid crystal materials for guest-host (GH) mode by incorporating therein dichroic dyes such as merocyanines, styryls, azo, azomethines, quinophthalones, anthraquinones, tetrazines or the like. Further, they can be used as liquid crystal materials for NPCA formed by microcapsulation of nematic liquid crystals, or as liquid crystal materials for polymer dispersion type If liquid crystal display elements (PDLCD), a typical example of which is a polymer network liquid crystal display element (PNLCD) wherein a three-dimensional network polymer is formed in the liquid crystal. In addition, they can be used as liquid crystal materials for electrically controlled birefringence (ECB) mode and dynamic scattering (DS) mode.

The invention is further illustrated by the following examples.

EXAMPLE 1

3-fluoro-4-cyanoethynyl-1-(trans-4-propylcyclohexyl)benzene (Compound No. 2)

A solution of 15 mmol of 3-fluoro-4-ethynyl-1-(trans-4-propylcyclohexyl)benzene in 5 ml of tetrahydrofuran was cooled to −78° C. and to the cooled solution was added dropwise 30 mmol of n-butyl lithium. After completion of the addition, the reaction solution was stirred for a further two hours and a solution of 20 mmol of iodine in 3 ml of tetrahydrofuran was added dropwise. After completion of the addition, the reaction solution was elevated to room temperature and poured into an aqueous solution of sodium thiosulfate. The solution was extracted with heptane, the resultant organic layer was washed with water, dried over anhydrous magnesium sulfate and concentratred under reduced pressure. The resulting yellow, oily product was isolated and purified by a silica gel column chromatography to afford colourless crystal which was identifed as 3-fluoro-4-iodoethynyl-1-(trans-4-propylcyclohexyl)benzene by analytical results.

To a solution of 10 mmol of 3-fluoro-4-iodoethynyl-1-(trans-4-propylcyclohexyl)benzene in 3 ml of tetrahydrofuran were added 11 mmol of copper cyanide and 3 mmol of lithium bromide, and the solution was stirred for 5 hours under reflux. To the reaction solution were added 10 ml of 6N hydrochloric acid saturated solution of ferric chloride and the solution was stirred at room temperature for one hour. After completion of the agitation, the reaction solution was extracted with toluene, the organic layer was washed with water, dried over anhydrous magnesium sulfate and concentratred under reduced pressure. The resulting brown, oily product was isolated and purified by a silica gel column chromatography to afford a colourless oily substance which was recrystallized from ethanol to afford colourless crystal. This was identified as the title compound by analytical results.

Using a similar method as in Example 1, there could be synthesized Compounds Nos. 1-5, 11-15, 21-29, 41-45, 51-55, 61-65, 71-75, 81-85, 91-95, 101-105, 111-114, 121-125, 131-135 and 221-240.

EXAMPLE 2

3-fluoro-4-cyanoethynyl-1-(4-propylphenyl) carbonyloxybenzene (Compound No. 153)

To a solution of 100 ml of 3-fluoro-4-cyanophenol in 200 ml of dimethylformamide were added 110 mmol of dimethylbutylsilyl chloride and 110 mmol of imidazole while cooling with an ice bath and stirring, the solution was elevated to room temperature and stirred for 3 hours. The solution was placed into water and extracted with toluene. The organic layer was dried over anhydrous magnesium sulfate and concentrated under reduced pressure to afford a colourless oily product. Distillation of the product under reduced pressure gave 100 mmol of 2-fluoro-4-dimethylbutylsilyloxy benzonitrile.

To a solution of 72 mmol of 2-fluoro-4-dimethylbutylsilyloxy benzonitrile in 100 ml of toluene were added dropwise 100 ml of a solution of di-isobutyl aluminum hydride (1M) in toluene, while cooling to −70° C. After completion of the addition, the reaction solution was stirred at the same temperature for one hour, poured into an ammonium chloride solution and extracted with toluene. The organic layer was dried over anhydrous magnesium sulfate and concentrated under reduced pressure to afford 26 mmol of 2-fluoro-4-dimethylbutylsilyloxy benzaldehyde as a yellow oily product. This product was used for subsequent reaction without purification.

To a solution of 26 mmol of 2-fluoro-4-dimethylbutylsilyloxy benzaldehyde in 50 ml of methylene chloride were added dropwise under ice-cooling 110 mmol of triphenyl phosphine and 52 mmol of carbon tetrabromide and the solution was stirred at the same temperature for one hour. The insoluble matter was removed from the reaction solution which was concentrated under reduced pressure to provide a yellow oily product. Purification of the product by a silica gel column chromatography gave 26 mmol of 2-fluoro-4-dimethylbutylsilyloxyphenyl-2,2-dibromoethylene as a colourless oily product.

To a solution of 26 mmol of 1-(2-fluoro-4-dimethylbutylsilyloxyphenyl)-2,2-dibromoethylene in 50 ml of tetrahydrofurane were added dropwise 134 ml of n-butyl lithium (1.6M), while stirring at −70° C. After completion of the addition, the reaction solution was stirred for 3 hours, 10 ml tetrahydrofuran solution of 30 mmol of iodine were added dropwise and the solution was gradually elevated to room temperature. Afer completion of the agitation, the solution was poured into a sodium thiosulfate solution and extracted with heptane. The organic layer was dried over anhydrous magnesium sulfate and concentrated under reduced pressure to afford a brown solid. Purification of the solid by a silica gel column chromatography gave 25 mmol of 1-(2-fluoro-4-dimethylbutylsilyloxyphenyl)-2-iodoethyne as a yellow solid.

To a solution of 25 mmol of 1-(2-fluoro-4-dimethylbutylsilyloxyphenyl)-2-iodoethyne in 50 ml of tetrahydrofuran were added copper cyanide and lithium bromide and the solution was reacted under reflux heating for 3 hours. After completion of the reaction, the solution was poured into a hydrochloric acid solution of ferric chloride and extracted with toluene. The organic layer was dried over anhydrous magnesium sulfate and concentrated under reduced pressure to afford 20 mmol of 2-fluoro-4-hydroxyphenylpropiolonitrile as a colourless solid.

To a solution of 20 mmol of 2-fluoro-4-hydroxyphenylpropiolonitrile and 21 mmol of 4-propylbenzoyl chloride in 50 ml of methylene chloride were added dropwise 25 mmol of pyridine, while stirring under ice-cooling and the solution was stirred for a further 3 hours. Water was added to the reaction solution which was extracted with toluene. The organic layer was washed with water, dried over anhydrous magnesium sulfate and concentrated under reduced pressure to afford a brown oily product. Purification of the product by a silica gel column chromatography and recrystallization from ethanol gave 8 mmol of the title compound.

Using a similar method as in Example 2, Compounds Nos. 141–220 could be synthesized.

EXAMPLE 3

4-[2-[trans-4-(3-butenyl)cyclohexyl]ethyl]-phenylpropiolonitrile (Compound No. 32)

To a solution of 42 mmol of 4-[2-[trans-4-(3-butenyl) cyclohexyl]ethyl]benzonitrile in 100 ml of toluene were added dropwise 45 ml of a toluene solution of isobutyl aluminum hydride (1M), while stirring under ice-cooling. The reaction solution was stirred at room temperature for a further 2 hours, poured into an aqueous solution of ammonium chloride and extracted with toluene. The organic layer was washed with water, dried over anhydrous magnesium sulfate and concentrated under reduced pressure to afford 35 mmol of 4-[2-[trans-4-(3-butenyl)cyclohexyl]ethyl] benzaldehyde as a colourless oily product. This product was used for subsequent reaction without purification.

To a solution of 10 mmol of carbon tetrabromide and 138 mmol of triphenylphosphine in 100 ml of methylene chloride was added dropwise a solution of 35 mmol of 4-[2-[trans-4-(3-butenyl)cyclohexyl]ethyl]benzaldehyde in methylene chloride. After completion of the addition, the reaction solution was stirred at room temperature for 3 hours, the insoluble matter was removed from the reaction system which was concentrated. Purification of the resultant brown oily product by a silica gel column chromatography gave 30 mmol of 2',2'-dibromo-4-[2-[trans- 4-(3-butenyl) cyclohexyl]ethyl]styrene as colourless crystal.

To a solution of 30 mmol of 2',2'-dibromo-4-[2-[trans-4-(3-butenyl)cyclohexyl]ethyl]styrene in 100 ml of tetrahydrofurane were added dropwise under ice-cooling 37.5 ml of a hexane solution of n-butyl lithium (1.6M). After completion of the addition, a tetrahydrofuran solution of iodine were added dropwise to the reaction solution, the solution was gradually elevated to room temperature and stirred for 3 hours. Afer completion of the reaction, the solution was placed into a sodium thiosulfate solution and extracted with heptane. The organic layer was washed with water, dried over anhydrous magnesium sulfate and concentrated under reduced pressure to afford a brown oily product. Purification of the product by a silica gel column chromatography gave 18 mmol of 2-[4-[2-trans-4-(3-butenyl)-cyclohexyl]ethyl] phenyl]iodoethyne as colourless crystal.

To a solution of 13.7 mmol of 2-[4-[2-trans-4-(3-butenyl) cyclohexyl]ethyl]phenyl]iodoethyne in tetrahydrofuran were added 1 mmol of lithium bromide and 22 mmol of copper cyanide and the solution was reacted under reflux for 5 hours. After completion of the reaction, the solution was poured into a 6 N hydrochloric acid solution of ferric chloride and extracted with toluene. The organic layer was washed with water, dried over anhydrous magnesium sulfate and concentrated under reduced pressure to afford a brown oily product. Isolation and purification of the product by a silica gel column chromatography and recrystallization from ethanol gave 4.1 mmol of the title compound.

Using a similar method as in Example 3, there could be synthesized Compounds Nos. 6-10, 16-20, 31-39, 46-49, 56-59, 66-69, 76-79, 86-90, 96-100, 106-110, 116-119, 126-127, 129-130, 136-137 and 139-140.

EXAMPLE 4

3-fluoro-4-[2-(4-propylphenyl)ethynyl]-phenylpropiolonitrile (Compound No. 30)

To a solution of 33 mmol of 3-fluoro-4-bromo iodobenzene, 0.6 mmol of copper iodide and 1.1 mmol of dichlorobistriphenylphosphine palladium in 100 ml of diethylamine were added dropwise 33 mmol of 4-propyl phenylacetylene under an argon stream while stirring. After completion of the addition, the solution was stirred at room temperature for a further 2 hours and placed into water. The solution was extracted with heptane, washed with water and concentrated under reduced pressure to afford a brown oily product. The product was isolated and purified by a silica gel column chromatography to afford 33 mmol of 2-fluoro-4-[2-(4-propylphenyl)ethynyl]bromobenzene as a pale yellow oily product.

33 mmol of 2-fluoro-4-[2-(4-propylphenyl)ethynyl] bromobenzene, 1.2 mmol of copper iodide and 1.2 mmol of dichlorobistriphenylphosphine palladium were dissolved in 100 ml of diethylamine and the solution was stirred under an argon stream. To the reaction solution were added dropwise 20 ml of a diethylamine solution of 50 mmol of trimethylsilylacetylene and the solution was stirred at room -temperature for 5 hours. After completion of the agitation, water was added to the reaction solution which was extracted with heptane. The organic layer was washed with water, dried over anhydrous magnesium sulfate and concentrated under reduced pressure to afford a brown oily product. This product was isolated and purified by a silica gel column chromatography to afford 7 g of 1-[2-fluoro-4-[2-(4-propylphenyl)ethynyl]phenyl]-2-trimethylsilylacetylene as a colourless solid.

22 mmol of 1-[2-fluoro-4-[2-(4-propylphenyl)-ethynyl] phenyl]-2-trimethylsilylacetylene and 10 g of potassium hydroxide were dissolved in 100 ml of ethanol and 10 ml of water, and the solution was stirred at 40° C. for 6 hours. After completion of the agitation, the reaction solution was poured into dilute hydrochloric acid and extracted with toluene. The organic layer was washed with water, dried over anhydrous magnesium sulfate and concentrated under reduced pressure to afford a brown oily product. This product was isolated and purified by a silica gel column chromatography to afford 5.7 g of 2-fluoro-4-[2-(4-propylphenyl)ethynyl]phenyl acetylene as a colourless solid.

To a solution of 22 mmol of 2-fluoro-4-[2-(4-propylphenyl)ethynyl]phenyl acetylene in 50 ml of tetrahydrofuran were added dropwise 30 ml of n-butyl lithium (1.6 M) while stirring at −78° C. After completion of the addition, the reaction solution was stirred for 2 hours and 50 ml of a tetrahydrofuran solution of 28 mmol of iodine were added dropwise. The solution was elevated to room temperature, poured into a sodium thiosulfate solution and extracted with heptane. The organic layer was washed with water, dried over anhydrous magnesium sulfate and concentrated under reduced pressure to afford a brown oily product. This product was isolated and purified by a silica gel column chromatography to afford 22 mmol of 1-[2-fluoro-4-[2-(4-propylphenyl)ethynyl]phenyl-2-iodoacetylene as yellow crystal.

22 mmol of 1-[2-fluoro-4-[2-(4-propylphenyl)-ethynyl] phenyl-2-iodoacetylene, 2 g of lithium bromide and 56 mmol of copper cyanide were dissolved in 100 ml of tetrahydrofuran and the solution was stirred under reflux heating for 5 hours. After completion of the reaction, the reaction solution was placed into a 6N hydrochloric acid solution of ferric chloride and extracted with toluene. The organic layer was washed with water, dried over anhydrous magnesium sulfate and concentrated under reduced pressure to afford a brown oily product. This product was isolated and purified by a silica gel column chromatography to give 0.6 g of the title compound as colourless crystal.

Using a similar method as in Example 4, there could be synthesized Compounds Nos. 30, 40, 50, 60, 70, 80, 115, 120, 128 and 138.

The liquid crystal compositions comprising the propiolonitrile derivatives of the present invention are further illustrated by the following examples with the nematic phase transition temperature (TN1), viscosity (7720) at 20° C., optical anisotropy (Δn) at 25° C., dielectric anisotropy (Δε) at 25° C. and threshold voltage (Vth) as determined.

In the examples, the chemical structure of the compound is shown by the following abbreviations, but only the carbon number is designated where the terminal group is alkyl.
Hx: trans-1,4-cyclohexylene
Be: 1,4-phenylene
Be (F): 1,4-phenylene which is substituted at 3-position by fluorine atoms
Be (F,F): 1,4-phenylene which is substituted at 3,5-positions by fluorine atoms
Py: 1,3.-pyrimidine-2,5-diyl
Do: 1,3-dioxane-2,5-diyl
Tr: ethynylene

EXAMPLE 5

| | |
|---|---|
| 3-Hx—Be(F)—Tr—CN (Compound No. 2) | 17.0% |
| 3-Hx—Be—CN | 15.0% |
| 3-Hx—Be—OC$_2$H$_5$ | 5.0% |
| 3-Hx—Hx-4 | 11.0% |
| 3-Hx—Hx-5 | 5.0% |
| 5-Hx—Hx-2 | 4.0% |
| 3-Hx—Hx—Be-1 | 10.0% |
| 3-Hx—Hx—Be-3 | 16.0% |
| 3-Hx—Be(F)—Tr—Be-2 | 5.0% |
| 3-Hx—C$_2$H$_4$—Be—Tr—Be-2 | 4.0% |
| 3-Hx—C$_2$H$_4$—Be—Tr—Be-3 | 4.0% |
| 3-Hx—C$_2$H$_4$—Be—Tr—Be-4 | 4.0% |
| T$_{NI}$ = 104.8[° C.] | |
| η = 14.0[mPa · s] | |
| Δn = 0.137 | |
| Δε = 7.8 | |
| V$_{th}$ = 2.23[V] | |

EXAMPLE 6

| | |
|---|---|
| 3-Hx—Be(F)—Tr—CN (Compound No. 2) | 15.0% |
| CH$_3$CH=CHC$_2$H$_4$—Be—COO—Be(F,F)—CN | 3.0% |
| 3-Hx—Be—CN | 14.0% |
| 3-Hx—Be—OC$_2$H$_5$ | 7.0% |
| 3-Hx—Hx-4 | 11.0% |
| 3-Hx—Hx-5 | 5.0% |
| 5-Hx—Hx-2 | 4.0% |
| 3-Hx—Hx-Be-1 | 10.0% |
| 3-Hx—Hx—Be-3 | 16.0% |
| 3-Hx—Be(F)—Tr—Be-2 | 3.0% |
| 3-Hx—C$_2$H$_4$—Be—Tr—Be-2 | 4.0% |
| 3-Hx—C$_2$H$_4$—Be—Tr—Be-3 | 4.0% |
| 3-Hx—C$_2$H$_4$—Be—Tr—Be-4 | 4.0% |
| T$_{NI}$ = 100.2[° C.] | |
| η = 14.7[mPa · s] | |
| Δn = 0.132 | |
| Δε = 8.8 | |
| V$_{th}$ = 2.13[V] | |

EXAMPLE 7

| | |
|---|---|
| CH$_2$=CHC$_2$H$_4$—Hx—Be—Tr—CN (Compound No. 7) | 10.0% |
| 3-Hx—Be(F)—Tr—CN (Compound No. 2) | 9.0% |
| CH$_2$=CHC$_2$H$_4$—Hx—Be—CN | 10.0% |
| CH$_3$CH=CHC$_2$H$_4$—Hx—Be—CN | 13.0% |
| 3-Hx—Hx-4 | 11.0% |
| 3-Hx—Hx-5 | 10.0% |
| 3-Hx—Hx—Be-1 | 10.0% |
| 3-Hx—Be(F)—Tr—Be-2 | 7.0% |
| 3-Hx—Be(F)—Tr—Be-3 | 7.0% |
| 3-Hx—Be(F)—Tr—Be-4 | 7.0% |
| 3-Hx—C$_2$H$_4$—Be—Tr—Be-3 | 6.0% |
| T$_{NI}$ = 111.7[° C.] | |
| η = 15.6[mPa · s] | |
| Δn = 0.164 | |
| Δε = 8.1 | |
| V$_{th}$ = 2.20[V] | |

EXAMPLE 8

| | |
|---|---|
| CH$_2$=CHC$_2$H$_4$—Hx—Be(F,F)—Tr—CN (Compound No. 8) | 8.0% |
| 3-Hx—Be—CN | 20.0% |
| CH$_2$=CHC$_2$H$_4$—Hx—Be—CN | 9.0% |
| 3-Hx—Hx-4 | 9.0% |
| 2-Be—Tr—Be-1 | 10.0% |
| 2-Be—Tr—Be-3 | 8.0% |
| 3-Hx—Hx—Be-1 | 8.0% |
| 3-Hx—Hx—Be—OCH$_3$ | 5.0% |
| 3-Hx—Hx—Be—F | 4.0% |
| 3-Hx—Hx—Be-3 | 7.0% |
| 3-Hx—C$_2$H$_4$—Be—Tr—Be-2 | 4.0% |
| 3-Hx—C$_2$H$_4$—Be—Tr—Be-3 | 4.0% |
| 3-Hx—C$_2$H$_4$—Be—Tr—Be-4 | 4.0% |
| T$_{NI}$ = 81.3[° C.] | |
| η = 13.1[mPa · s] | |
| Δn = 0.155 | |
| Δε = 7.1 | |
| V$_{th}$ = 1.96[V] | |

EXAMPLE 9

| | |
|---|---|
| 3-Be—COO—Be(F)—Tr—CN (Compound No. 153) | 12.0% |
| 3-Hx—Be—COO—Be(F)—Tr—CN (Compound No. 162) | 8.0% |
| C$_3$H$_7$OCH$_2$—Be—COO—Be(F)—CN | 12.0% |
| 2-Hx—Be—CN | 12.0% |
| 3-Hx—Be—CN | 19.0% |
| 3-Hx—Be—OC$_2$H$_5$ | 7.0% |
| 3-Hx—Hx—Be-1 | 7.0% |
| 3-Hx—Hx—Be—OCH$_3$ | 4.0% |
| 3-Hx—C$_2$H$_4$—Be—Tr—Be-2 | 4.0% |
| 3-Hx—C$_2$H$_4$—Be—Tr—Be-3 | 3.0% |
| 3-Hx—C$_2$H$_4$—Be—Tr—Be-4 | 3.0% |
| 2-Hx—Hx—Be—CN | 4.0% |
| 3-Hx—Hx—Be—CN | 5.0% |
| T$_{NI}$ = 91.4[° C.] | |
| η = 33.7[mPa · s] | |
| Δn = 0.163 | |
| Δε = 20.9 | |
| V$_{th}$ = 1.13[V] | |

EXAMPLE 10

| | |
|---|---|
| 3-Be—Tr—Be(F)—Tr—CN (Compound No. 30) | 10.0% |
| 3-Hx—Be—CN | 20.0% |
| 1-Be—Tr—Be-3 | 8.0% |
| 2-Be—Tr—Be-1 | 10.0% |
| 2-Be—Tr—Be—OCH$_3$ | 1.6% |
| 3-Be—Tr—Be—OCH$_3$ | 1.6% |
| 4-Be—Tr—Be—OCH$_3$ | 1.6% |
| 4-Be—Tr—Be—OC$_2$H$_5$ | 1.6% |
| 5-Be—Tr—Be—OCH$_3$ | 1.6% |
| 3-Hx—Hx—Be-1 | 11.0% |
| 3-Hx—Hx—Be-3 | 9.0% |
| 3-Hx—C$_2$H$_4$—Be—Tr—Be-2 | 4.0% |
| 3-Hx—C$_2$H$_4$—Be—Tr—Be-3 | 4.0% |
| 3-Hx—C$_2$H$_4$—Be—Tr—Be-4 | 4.0% |
| 3-Hx—Be(F)—Tr—Be-2 | 6.0% |
| 3-Hx—Be(F)—Tr—Be-3 | 6.0% |
| T$_{NI}$ = 98.1[° C.] | |
| η = 16.3[mPa · s] | |
| Δn = 0.220 | |
| Δε = 7.3 | |
| V$_{th}$ = 2.07[V] | |

EXAMPLE 11

| | |
|---|---|
| 3-Hx—Be(F)—Tr—CN (Compound No. 2) | 10.0% |
| 2-Hx—Be(F)—CN | 10.0% |
| 3-Hx—Be(F)—CN | 10.0% |
| 3-Hx—Be—OC$_2$H$_5$ | 10.0% |
| 3-Hx—Hx-4 | 10.0% |
| 2-Be—Tr—Be—OCH$_3$ | 10.0% |
| 3-Hx—Hx—Be-1 | 8.0% |
| 3-Hx—Hx—Be-3 | 16.0% |
| 3-Hx—Hx—Be—OCH$_3$ | 4.0% |

-continued

| | |
|---|---|
| 3-Hx—C₂H₄—Be—Tr—Be-2 | 4.0% |
| 3-Hx—C₂H₄—Be—Tr—Be-3 | 4.0% |
| 3-Hx—Hx—Be—CN | 4.0% |
| $T_{NI}$ = 88.7[° C.] | |
| η = 16.1[mPa · s] | |
| Δn = 0.136 | |
| Δε = 7.7 | |
| $V_{th}$ = 1.86[V] | |

EXAMPLE 12

| | |
|---|---|
| CH₂=CHC₂H₄—Hx—Be(F,F)—Tr—CN (Compound No. 8) | 8.0% |
| CH₃CH=CHC₂H₄—Be—COO—Be(F,F)—CN | 4.0% |
| C₃H₇OCH₂—Be—COO—Be(F)—CN | 8.0% |
| 2-Hx—Be(F)—CN | 8.0% |
| 5-Py—Be—F | 3.0% |
| 3-Py—Be(F)—F | 3.0% |
| 3-Hx—Be—OC₂H₅ | 10.0% |
| 3-Hx—Hx-4 | 10.0% |
| 2-Be—Tr—Be—OCH₃ | 10.0% |
| 3-Hx—Hx—Be-1 | 10.0% |
| 3-Hx—Hx—Be-3 | 14.0% |
| 3-Hx—Hx—Be—OCH₃ | 4.0% |
| 3-Hx—C₂H₄—Be—Tr—Be-2 | 4.0% |
| 3-Hx—C₂H₄—Be—Tr—Be-3 | 4.0% |
| $T_{NI}$ = 69.2[° C.] | |
| η = 17.6[mPa · s] | |
| Δn = 0.133 | |
| Δε = 10.3 | |
| $V_{th}$ = 1.40[V] | |

EXAMPLE 13

| | |
|---|---|
| CH₂=CHC₂H₄—Hx—Be(F,F)—Tr—CN (Compound No. 8) | 10.0% |
| 3-Hx—Be—CN | 20.0% |
| 3-Hx—Be(F)—CN | 5.0% |
| 2-Hx—Hx—Be(F)—CN | 7.0% |
| 3-Hx—Hx—Be(F)—CN | 7.0% |
| 3-Hx—Hx-4 | 10.0% |
| 3-Hx—Be—OC₂H₅ | 11.0% |
| 3-Hx—Hx—Be-1 | 7.0% |
| 3-Hx—Hx—Be—OCH₃ | 4.0% |
| 3-Hx—Hx—Be-3 | 4.0% |
| 3-Hx—C₂H₄—Be—Tr—Be-2 | 3.0% |
| 3-Hx—C₂H₄—Be—Tr—Be-3 | 3.0% |
| 3-Hx—C₂H₄—Be—Tr—Be-4 | 3.0% |
| CH₃OCH₂—Hx—Be—Be—Hx-3 | 6.0% |
| $T_{NI}$ = 101.0[° C.] | |
| η = 20.3[mPa · s] | |
| Δn = 0.134 | |
| Δε = 9.1 | |
| $V_{th}$ = 1.91[V] | |

EXAMPLE 14

| | |
|---|---|
| 3-Be—Tr—Be(F)—Tr—CN (Compound No. 30) | 13.0% |
| 3-Hx—Be—CN | 15.0% |
| CH₂=CHC₂H₄—Hx—Be—CN | 9.0% |
| CH₃CH=CHC₂H₄—Be—COO—Be(F,F)—CN | 2.0% |
| 3-Hx—Hx—COO—CH₃ | 2.0% |
| 3-Hx—Hx-4 | 9.0% |
| 2-Be—Tr—Be-1 | 10.0% |
| 2-Be—Tr—Be-3 | 6.0% |
| 3-Hx—Hx—Be-1 | 5.0% |
| 3-Hx—Hx—Be—OCH₃ | 5.0% |
| 3-Hx—Be—Be—F | 5.0% |
| 3-Hx—Hx—Be-3 | 15.0% |
| 3-Hx—COO—Be—COO—Be-2 | 2.0% |
| 3-Hx—COO—Be—COO—Be—F | 2.0% |

-continued

| | |
|---|---|
| $T_{NI}$ = 84.2[° C.] | |
| η = 16.6[mPa · s] | |
| Δn = 0.170 | |
| Δε = 8.7 | |
| $V_{th}$ = 1.69[V] | |

EXAMPLE 15

| | |
|---|---|
| 3-Be—COO—Be(F)—Tr—CN (Compound No. 153) | 11.0% |
| CH₂=CHC₂H₄—Hx—Be—Tr—CN (Compound No. 7) | 11.0% |
| 3-Hx—Be—OC₂H₅ | 3.0% |
| 2-Be—Tr—Be—OCH₃ | 6.8% |
| 3-Be—Tr—Be—OCH₃ | 6.8% |
| 4-Be—Tr—Be—OCH₃ | 6.8% |
| 4-Be—Tr—Be—OC₂H₅ | 6.8% |
| 5-Be—Tr—Be—OCH₃ | 6.8% |
| 3-Hx—Hx—Be—OCH₃ | 3.0% |
| 3-Hx—C₂H₄—Be—Tr—Be-2 | 2.0% |
| 3-Hx—C₂H₄—Be—Tr—Be-3 | 3.0% |
| 3-Hx—C₂H₄—Be—Tr—Be-4 | 3.0% |
| 3-Hx—Be(F)—Tr—Be-2 | 6.0% |
| 3-Hx—Be(F)—Tr—Be-3 | 6.0% |
| 3-Hx—Be(F)—Tr—Be-4 | 6.0% |
| 2-Py—Be—H-3 | 4.0% |
| 3-Py—Be—Hx-3 | 4.0% |
| 3-Py—Be—Be-2 | 4.0% |
| $T_{NI}$ = 108.8[° C.] | |
| η = 27.4[mPa · s] | |
| Δn = 0.246 | |
| Δε = 9.6 | |
| $V_{th}$ = 1.93[V] | |

EXAMPLE 16

| | |
|---|---|
| CH₂=CHC₂H₄—Hx—Be—Tr—CN (Compound No. 7) | 9.0% |
| 3-Hx—Be—COO—Be(F)—Tr—CN (Compound No. 162) | 10.0% |
| CH₃CH=CHC₂H₄—Hx—Be—CN | 9.0% |
| 3-Hx—Be—CN | 14.0% |
| CH₃OCH₂—Hx—Be—CN | 8.0% |
| C₂H₅OCH₂—Hx—Be—CN | 4.0% |
| 3-Hx—Hx-4 | 10.0% |
| CH₃OCH₂—Hx—Hx-5 | 8.0% |
| 2-Be—Tr—Be—OCH₃ | 11.0% |
| 3-Hx—Hx—Be-1 | 8.0% |
| 3-Hx—Hx—Be-3 | 9.0% |
| $T_{NI}$ = 84.0[° C.] | |
| η = 16.8[mPa · s] | |
| Δn = 0.143 | |
| Δε = 12.0 | |
| $V_{th}$ = 1.64[V] | |

EXAMPLE 17

| | |
|---|---|
| 3-Be—COO—Be(F)—Tr—CN (Compound No. 153) | 12.0% |
| CH₃CH=CHC₂H₄—Be—COO—Be(F,F)—CN | 6.0% |
| C₃H₇OCH₂—Be—COO—Be(F)—CN | 6.0% |
| 2-Hx—Be—CN | 12.0% |
| 3-Hx—Be—CN | 16.0% |
| 2-Hx—Hx—Be—CN | 4.0% |
| 3-Hx—Hx—Be—CN | 5.0% |
| 4-Hx—Hx—Be—CN | 4.0% |
| 5-Hx—Hx—Be—CN | 4.0% |
| 3-Hx—Be—OC₂H₅ | 10.0% |
| 3-Hx—Hx—Be-1 | 7.0% |
| 3-Hx—Hx—Be—OCH₃ | 4.0% |
| 3-Hx—C₂H₄—Be—Tr—Be-2 | 4.0% |
| 3-Hx—C₂H₄—Be—Tr—Be-3 | 3.0% |
| 3-Hx—C₂H₄—Be—Tr—Be-4 | 3.0% |
| $T_{NI}$ = 90.4[° C.] | |

-continued $\eta = 28.5[\text{mPa} \cdot \text{s}]$
$\Delta n = 0.155$
$\Delta \epsilon = 19.0$
$V_{th} = 1.20[V]$

EXAMPLE 18

| | |
|---|---|
| 3-Be—COO—Be(F)—Tr—CN (Compound No. 153) | 10.0% |
| C$_3$H$_7$OCH$_2$—Be—COO—Be(F)—CN | 8.0% |
| C$_5$H$_{11}$OCH$_2$—Be—COO—Be(F)—CN | 4.0% |
| CH$_3$CH=CHC$_2$H$_4$—Be—COO—Be(F,F)—CN | 10.0% |
| C$_2$H$_5$OCH$_2$—Hx—Be—COO—Be(F)—CN | 2.0% |
| 3-Hx—Be(F)—COO—Be(F)—CN | 2.0% |
| 2-Hx—Be—COO—Be(F,F)—CN | 2.0% |
| 3-Hx—Hx—COO—Be—F | 5.0% |
| 5-Hx—Hx—COO—Be—F | 4.0% |
| 3-Hx—Be—COO—Be—F | 6.0% |
| 3-Hx—Be—OC$_2$H$_5$ | 10.0% |
| 3-Hx—Hx-4 | 10.0% |
| 3-Hx—Hx—Be-1 | 8.0% |
| 3-Hx-Hx—Be-3 | 10.0% |
| 3-Hx—Hx—Be—OCH$_3$ | 4.0% |
| 3-Hx—Be(F)—CH=CH—Be-2 | 5.0% |

$T_{NI} = 99.0[° C.]$
$\eta = 36.8[\text{mPa} \cdot \text{s}]$
$\Delta n = 0.135$
$\Delta \epsilon = 23.6$
$V_{th} = 1.10[V]$

EXAMPLE 19

| | |
|---|---|
| CH$_2$=CHC$_2$H$_4$—Hx—Be—Tr—CN (Compound No. 7) | 10.0% |
| 3-Hx—Be(F)—Tr—CN (Compound No. 2) | 7.0% |
| 2-Hx—Be(F)—CN | 10.0% |
| 3-Hx—Be(F)—CN | 10.0% |
| 5-Hx—Be(F)—CN | 9.0% |
| 2-Be—COO—Be—CN | 10.0% |
| 3-Be—COO—Be—CN | 4.0% |
| 2-Hx—Hx—Be(F)—CN | 9.0% |
| 3-Hx—Hx—Be(F)—CN | 12.0% |
| 3-Py—Be—Be—F | 8.0% |
| 2-Hx—Hx—Be—CN | 3.0% |
| 3-Hx—Hx—Be—CN | 3.0% |
| 3-Hx—Be—COO—Be—Be—CN | 3.0% |
| 5-Hx—Hx—COO—Be—Be—CN | 2.0% |

$T_{NI} = 91.5[° C.]$
$\eta = 52.8[\text{mPa} \cdot \text{s}]$
$\Delta n = 0.164$
$\Delta \epsilon = 19.3$
$V_{th} = 1.00[V]$

EXAMPLE 20

| | |
|---|---|
| 3-Hx—Be(F)—Tr—CN (Compound No. 2) | 13.0% |
| CH$_2$=CHC$_2$H$_4$—Hx—Be(F,F)—Tr—CN (Compound No. 8) | 10.0% |
| 2-Be—Be—CN | 8.0% |
| 4-Be—Be—CN | 6.0% |
| 3-Hx—Hx—Be—F | 5.0% |
| 2-Hx—Hx—Be—CN | 4.0% |
| 3-Hx—Hx—Be—CN | 6.0% |
| 5-Py—Be—F | 6.0% |
| 3-Py—Be—Be—F | 6.0% |
| 2-Be—Tr—Be—OCH$_3$ | 2.0% |
| 2-Hx—Hx—Be-1 | 6.0% |
| 3-Hx—Hx—Be-1 | 8.0% |
| 3-Hx—Hx—Be-3 | 15.0% |
| 3-Hx—Hx—Be—OCH$_3$ | 5.0% |

$T_{NI} = 105.6[° C.]$
$\eta = 21.6[\text{mPa} \cdot \text{s}]$

-continued $\Delta n = 0.169$
$\Delta \epsilon = 11.3$
$V_{th} = 1.66[V]$

EXAMPLE 21

| | |
|---|---|
| 3-Hx—Be—COO—Be(F)—Tr—CN (Compound No. 162) | 11.0% |
| 3-Hx—Be—OC$_2$H$_5$ | 14.0% |
| 3-Hx—Be—OC$_4$H$_9$ | 13.0% |
| 3-Py—Be-4 | 3.1% |
| 4-Py—Be-4 | 3.1% |
| 6-Py—Be-4 | 3.2% |
| 3-Py—Be-5 | 3.2% |
| 4-Py—Be-5 | 3.2% |
| 6-Py—Be-5 | 3.2% |
| 6-Py—Be—OC$_5$H$_{11}$ | 4.0% |
| 6-Py—Be—OC$_6$H$_{13}$ | 4.0% |
| 6-Py—Be—OC$_7$H$_{15}$ | 4.0% |
| 6-Py—Be—OC$_8$H$_{17}$ | 4.0% |
| 2-Hx—Hx—Be-1 | 4.0% |
| 3-Hx—Hx—Be-1 | 8.0% |
| 3-Hx—Hx—Be-3 | 10.0% |
| 3-Hx—Hx—Be—OCH$_3$ | 5.0% |

$T_{NI} = 78.8[° C.]$
$\eta = 35.3[\text{mPa} \cdot \text{s}]$
$\Delta n = 0.130$
$\Delta \epsilon = 5.4$
$V_{th} = 2.47[V]$

EXAMPLE 22

| | |
|---|---|
| 3-Be—COO—Be(F)—Tr—CN (Compound No. 153) | 10.0% |
| 3-Do—Be—CN | 10.0% |
| 4-Do—Be—CN | 12.0% |
| 5-Do—Be—CN | 8.0% |
| 5-Py—Be(F)—F | 10.0% |
| 2-Py—Be-2 | 1.4% |
| 3-Py—Be-2 | 1.3% |
| 4-Py—Be-2 | 1.3% |
| 3-Hx—COO—Be—OC$_4$H$_9$ | 5.0% |
| 4-Hx—COO—Be—OC$_2$H$_5$ | 3.7% |
| 3-Hx—COO—Be—OC$_2$H$_5$ | 3.1% |
| 1O—Be—COO—Be-2 | 2.5% |
| 5-Hx—COO—Be-1 | 3.7% |
| 4-Hx—COO—Be-4 | 5.0% |
| 3-Hx—Hx—Be—OCH$_3$ | 4.0% |
| 3-Hx—Hx—Be-3 | 13.0% |
| 2-Py—Be—Hx-3 | 6.0% |

$T_{NI} = 63.5[° C.]$
$\eta = 30.2[\text{mPa} \cdot \text{s}]$
$\Delta n = 0.123$
$\Delta \epsilon = 15.6$
$V_{th} = 1.25[V]$

EXAMPLE 23

| | |
|---|---|
| 3-Be—COO—Be(F)—Tr—CN (Compound No. 153) | 6.0% |
| CH$_2$=CHC$_2$H$_4$—Hx—Be—Tr—CN (Compound No. 7) | 4.0% |
| 3-Be—COO—Be(F)—CN | 8.0% |
| 5-Py—Be—CN | 8.0% |
| CH$_2$=CH—Hx—Be—CN | 4.0% |
| CH$_3$CH=CH—Hx—Be—CN | 4.0% |
| 5-Hx—Hx—CH=CH$_2$ | 10.0% |
| 3-Hx—Hx—C$_2$H$_4$CH=CH$_2$ | 7.0% |
| 3-Hx—Hx—C$_2$H$_4$CH=CHCH$_3$ | 7.0% |
| CH$_2$=CH—Hx—Hx—Be-1 | 8.0% |
| CH$_2$=CHC$_2$H$_4$-Hx—Hx—Be-1 | 15.0% |
| 3-Hx—Hx—COO—Be(F)—F | 5.0% |
| 3-Hx—Be—Tr—Be-1 | 5.0% |

| | |
|---|---|
| 3-Hx—Be—Tr—Be-2 | 5.0% |
| 3-Hx—Be—Tr—Be-3 | 4.0% |
| $T_{NI} = 101.0[°C.]$ | |
| $\eta = 15.8[mPa \cdot s]$ | |
| $\Delta n = 0.143$ | |
| $\Delta \epsilon = 11.1$ | |
| $V_{th} = 1.86[V]$ | |

EXAMPLE 24

| | |
|---|---|
| CH$_2$=CHC$_2$H$_4$—Hx—Be—Tr—CN (Compound No. 7) | 5.0% |
| 7-Hx—Be(F,F)—F | 4.0% |
| 3-Hx—C$_2$H$_4$—Hx—Be(F,F)—F | 12.0% |
| 4-Hx—C$_2$H$_4$—Hx—Be(F,F)—F | 10.0% |
| 5-Hx—C$_2$H$_4$—Hx—Be(F,F)—F | 10.0% |
| 3-Hx—Hx—Be(F,F)—F | 10.0% |
| 3-Hx—Hx—C$_2$H$_4$—Be(F,F)—F | 11.0% |
| 5-Hx—Hx—C$_2$H$_4$—Be(F,F)—F | 10.0% |
| 3-Hx—Be—Be(F,F)—F | 12.0% |
| 5-Hx—Be—Be(F,F)—F | 12.0% |
| 3-Hx—Hx—Be—Be(F,F)—F | 2.0% |
| 5-Hx—Hx—C$_2$H$_4$—Be—Be(F,F)—F | 2.0% |
| $T_{NI} = 78.9[°C.]$ | |
| $\eta = 26.9[mPa \cdot s]$ | |
| $\Delta n = 0.097$ | |
| $\Delta \epsilon = 9.2$ | |
| $V_{th} = 1.53[V]$ | |

EXAMPLE 25

| | |
|---|---|
| CH$_2$=CHC$_2$H$_4$—Hx—Be(F,F)—Tr—CN (Compound No. 8) | 15.0% |
| 7-Hx—Be(F,F)—F | 5.0% |
| 3-Hx—C$_2$H$_4$—Hx—Be(F,F)—F | 9.0% |
| 4-Hx—C$_2$H$_4$—Hx—Be(F,F)—F | 8.0% |
| 5-Hx—C$_2$H$_4$—Hx—Be(F,F)—F | 8.0% |
| 3-Hx—Hx—C$_2$H$_4$—Be(F,F)—F | 10.0% |
| 3-Hx—Be—Be(F,F)—F | 9.0% |
| 5-Hx—Be—Be(F,F)—F | 9.0% |
| 3-Hx—Hx—Be(F,F)—F | 6.0% |
| 4-Hx—Hx—Be(F,F)—F | 5.0% |
| 3-Hx—Be—COO—Be(F,F)—F | 3.0% |
| 5-Hx—Be—COO—Be(F,F)—F | 3.0% |
| 3-Hx—Hx—COO—Be(F,F)—F | 10.0% |
| $T_{NI} = 68.2[°C.]$ | |
| $\eta = 25.4[mPa \cdot s]$ | |
| $\Delta n = 0.105$ | |
| $\Delta \epsilon = 13.7$ | |
| $V_{th} = 1.17[V]$ | |

EXAMPLE 26

| | |
|---|---|
| 3-Hx—Be(F)—Tr—CN (Compound No. 2) | 7.0% |
| 3-Hx—Be—COO—Be(F)—Tr—CN (Compound No. 162) | 6.0% |
| 5-Hx—C$_2$H$_4$—Be(F)—F | 4.0% |
| 7-Hx—Be(F)—F | 7.0% |
| 2-Hx—Hx—Be(F)—F | 9.0% |
| 3-Hx—Hx—Be(F)—F | 9.0% |
| 5-Hx—Hx—Be(F)—F | 9.0% |
| 2-Hx—C$_2$H$_4$—Hx—Be(F)—F | 4.0% |
| 3-Hx—C$_2$H$_4$—Hx—Be(F)—F | 2.0% |
| 5-Hx—C$_2$H$_4$—Hx—Be(F)—F | 4.0% |
| 3-Hx—C$_2$H$_4$—Hx—Be(F,F)—F | 6.0% |
| 4-Hx—C$_2$H$_4$—Hx—Be(F,F)—F | 5.0% |
| 5-Hx—C$_2$H$_4$—Hx—Be(F,F)—F | 5.0% |
| 3-Hx—Hx—Be(F,F)—F | 8.0% |
| 3-Hx—Hx—C$_2$H$_4$—Be(F,F)—F | 8.0% |
| 5-Hx—Hx—C$_2$H$_4$—Be(F,F)—F | 7.0% |
| $T_{NI} = 82.4[°C.]$ | |
| $\eta = 25.0[mPa \cdot s]$ | |

| | |
|---|---|
| $\Delta n = 0.093$ | |
| $\Delta \epsilon = 7.6$ | |
| $V_{th} = 1.60[V]$ | |

EXAMPLE 27

| | |
|---|---|
| 3-Be—Tr—Be(F)—Tr—CN (Compound No. 30) | 10.0% |
| 3-Hx—Be—Cl | 7.0% |
| 4-Hx—C$_2$H$_4$—Be—Be(F)—F | 3.0% |
| 2-Hx—Be—Be(F)—F | 6.0% |
| 3-Hx—Be—Be(F)—F | 6.0% |
| 5-Hx—Be—Be(F)—F | 12.0% |
| 2-Hx—Hx—Be—Cl | 5.0% |
| 4-Hx—Hx—Be—Cl | 10.0% |
| 5-Hx—Hx—Be—Cl | 4.0% |
| 3-Hx—Be—Be(F,F)—F | 17.0% |
| 5-Hx—Be—Be(F,F)—F | 12.0% |
| 5-Hx—C$_2$H$_4$—Be—Be(F,F)—F | 5.0% |
| 3-Hx—Hx—Be-1 | 3.0% |
| $T_{NI} = 93.7[°C.]$ | |
| $\eta = 24.9[mPa \cdot s]$ | |
| $\Delta n = 0.160$ | |
| $\Delta \epsilon = 7.8$ | |
| $V_{th} = 1.60[V]$ | |

EXAMPLE 28

| | |
|---|---|
| 3-Be—COO—Be(F)—Tr—CN (Compound No. 153) | 5.0% |
| 5-Hx—COO—Be—F | 2.0% |
| 7-Hx—COO—Be—F | 2.0% |
| 2-Hx—Hx—Be(F)—F | 10.0% |
| 3-Hx—Hx—Be(F)—F | 10.0% |
| 5-Hx—Hx—Be(F)—F | 10.0% |
| 2-Hx—Be—Be(F)—F | 7.0% |
| 3-Hx—Be—Be(F)—F | 7.0% |
| 5-Hx—Be—Be(F)—F | 14.0% |
| 2-Hx—Be—Be—F | 4.0% |
| 3-Hx—Be—Be—F | 4.0% |
| 5-Hx—Be—Be—F | 3.0% |
| 3-Hx—Be—Be(F,F)—F | 5.0% |
| 5-Hx—Be—Be(F,F)—F | 10.0% |
| 3-Hx—Be—OC$_2$H$_5$ | 7.0% |
| $T_{NI} = 87.4[°C.]$ | |
| $\eta = 25.7[mPa \cdot s]$ | |
| $\Delta n = 0.121$ | |
| $\Delta \epsilon = 7.8$ | |
| $V_{th} = 1.72[V]$ | |

EXAMPLE 29

| | |
|---|---|
| CH$_2$=CHC$_2$H$_4$—Hx—Be(F,F)—Tr—CN (Compound No. 8) | 7.0% |
| 5-Hx—Be—F | 12.0% |
| 6-Hx—Be—F | 9.0% |
| 2-Hx—Hx—Be—OCF$_3$ | 7.0% |
| 3-Hx—Hx—Be—OCF$_3$ | 11.0% |
| 4-Hx—Hx—Be—OCF$_3$ | 7.0% |
| 5-Hx—Hx—Be—OCF$_3$ | 10.0% |
| 3-Hx—Be—Be(F)—F | 13.0% |
| 5-Hx—Be—Be(F)—F | 10.0% |
| 3-Hx—Hx—C$_2$H$_4$—Be—OCF$_3$ | 4.0% |
| 5-Hx—Hx—C$_2$H$_4$—Be—OCF$_3$ | 4.0% |
| 3-Hx—Be(F)—Be—Hx-3 | 2.0% |
| 5-Hx—Be(F)—Be—Hx-3 | 2.0% |

-continued

| | |
|---|---|
| 5-Hx—Be(F)—Be—Hx-5 | 2.0% |
| $T_{NI}$ = 99.4[° C.] | |
| $\eta$ = 16.1[mPa · s] | |
| $\Delta n$ = 0.109 | |
| $\Delta \epsilon$ = 6.1 | |
| $V_{th}$ = 1.94[V] | |

EXAMPLE 30

| | |
|---|---|
| 3-Hx—Be(F)—Tr—CN (Compound No. 2) | 6.0% |
| 5-Hx—Be—F | 5.0% |
| 7-Hx—Be—F | 6.0% |
| 2-Hx—Hx—Be—$OCF_3$ | 8.0% |
| 3-Hx—Hx—Be—$OCF_3$ | 9.0% |
| 5-Hx—Hx—Be—$OCF_3$ | 11.0% |
| 3-Hx—Hx—Be—$OCF_2H$ | 5.0% |
| 5-Hx—Hx—Be—$OCF_2H$ | 4.0% |
| 3-Hx—Hx—Be(F,F)—$OCF_2H$ | 7.0% |
| 5-Hx—Hx—Be(F,F)—$OCF_2H$ | 13.0% |
| 3-Hx—Hx—$C_2H_4$—Be(F)—F | 11.0% |
| 5-Hx—Hx—$C_2H_4$—Be(F)—F | 5.0% |
| 3-Hx—Hx—COO—Be(F)—F | 5.0% |
| 5-Hx—Hx—COO—Be(F)—F | 5.0% |
| $T_{NI}$ = 101.0[° C.] | |
| $\eta$ = 21.1[mPa · s] | |
| $\Delta n$ = 0.093 | |
| $\Delta \epsilon$ = 7.0 | |
| $V_{th}$ = 2.11[V] | |

EXAMPLE 31

| | |
|---|---|
| 3-Be—COO—Be(F)—Tr—CN (Compound No. 153) | 10.0% |
| 3-Hx—Be—COO—Be(F)—Tr—CN (Compound No. 162) | 5.0% |
| 3-Hx—Be(F)—CN | 5.0% |
| $CH_2$=CH—Hx—Be—CN | 10.0% |
| $CH_3$CH=CH—Hx—Be—CN | 10.0% |
| 2-Be—Tr—Be—$OCH_3$ | 10.0% |
| 3-Hx—Be—$OC_2H_5$ | 10.0% |
| $CH_2$=$CHC_2H_4$—Hx—Hx-3 | 5.0% |
| $CH_2$=CH—Hx—Hx-4 | 5.0% |
| $CH_2$=CH—Hx—Hx—Be-1 | 10.0% |
| $CH_3$CH=$CHC_2H_4$—Hx—Be—Be-2 | 10.0% |
| 3-Hx—Hx—Be-1 | 10.0% |
| $T_{NI}$ = 83.1[° C.] | |
| $\eta$ = 19.0[mPa · s] | |
| $\Delta n$ = 0.151 | |
| $\Delta \epsilon$ = 10.3 | |
| $V_{th}$ = 1.40[V] | |

EXAMPLE 32

| | |
|---|---|
| $CH_3$CH=CH—Hx—Hx—Be—Tr—CN (Compound No. 87) | 10.0% |
| $CH_2$=$CHC_2H_4$—Hx—Be—CN | 11.0% |
| $CH_3$CH=$CHC_2H_4$—Hx—Be—CN | 10.0% |
| $CH_3OCH_2$—Hx—Be—CN | 10.0% |
| 2-Hx—Be—CN | 5.0% |
| 3-Hx—Be—CN | 5.0% |
| 3-Hx—Hx-4 | 11.0% |
| 2-Be—Tr—Be—$OCH_3$ | 4.2% |
| 3-Be—Tr—Be—$OCH_3$ | 4.2% |
| 4-Be—Tr—Be—$OCH_3$ | 4.2% |
| 4-Be—Tr—Be—$OC_2H_5$ | 4.2% |
| 5-Be—Tr—Be—$OCH_3$ | 4.2% |
| 3-Hx—Hx—Be—CN | 5.0% |
| 5-Hx—Hx—Be—CN | 5.0% |
| 3-Hx—Hx—Be-1 | 4.0% |
| 3-Hx—Hx—Be—F | 3.0% |

EXAMPLE 33

| | |
|---|---|
| 5-Be—COO—Be(F,F)—Tr—CN (Compound No. 155) | 12.0% |
| $CH_3$CH=$CHC_2H_4$—Be—COO—Be(F,F)—CN | 6.0% |
| $C_3H_7OCH_2$—Be—COO—Be(F)—CN | 6.0% |
| 2-Hx—Be—CN | 12.0% |
| 3-Hx—Be—CN | 19.0% |
| 2-Hx—Hx—Be—CN | 4.0% |
| 3-Hx—Hx—Be—CN | 5.0% |
| 4-Hx—Hx—Be—CN | 4.0% |
| 5-Hx—Hx—Be—CN | 4.0% |
| 3-Hx—Be—$OC_2H_5$ | 7.0% |
| 3-Hx—Hx—Be-1 | 7.0% |
| 3-Hx—Hx—Be—$OCH_3$ | 4.0% |
| 3-Hx—$C_2H_4$—Be—Tr—Be-2 | 4.0% |
| 3-Hx—$C_2H_4$—Be—Tr—Be-3 | 3.0% |
| 3-Hx—$C_2H_4$—Be—Tr—Be-4 | 3.0% |

EXAMPLE 34

| | |
|---|---|
| $CH_3$O—Be—COO—Be(F)—Tr—CN (Compound No. 151) | 4.0% |
| 5-Hx—CH=CH—Hx—Be—Tr—CN (Compound No. 63) | 3.0% |
| $CH_2$=CH—Hx—CH=CH—Hx—Be—Tr—CN (Compound No. 66) | 3.0% |
| 3-Hx—Be—CN | 20.0% |
| 1-Be—Tr—Be-3 | 5.0% |
| 2-Be—Tr—Be-1 | 10.0% |
| 3-Hx—Hx-4 | 11.0% |
| 3-Hx—Hx—Be-1 | 11.0% |
| 3-Hx—Hx—Be-3 | 9.0% |
| 3-Hx—$C_2H_4$—Be—Tr—Be-2 | 4.0% |
| 3-Hx—$C_2H_4$—Be—Tr—Be-3 | 4.0% |
| 3-Hx—$C_2H_4$—Be—Tr—Be-4 | 4.0% |
| 3-Hx—Be(F)—Tr—Be-2 | 6.0% |
| 3-Hx—Be(F)—Tr—Be-3 | 6.0% |

EXAMPLE 35

| | |
|---|---|
| 3-Be—COO—Be(F,F)—Tr—CN (Compound No. 154) | 6.0% |
| 5-Be—COO—Be(F,F)—Tr—CN (Compound No. 155) | 4.0% |
| 3-Hx—Be(F,F)—Tr—CN (Compound No. 3) | 5.0% |
| 3-Hx—Be—CN | 17.0% |
| 3-Hx—Be—$OC_2H_5$ | 4.0% |
| 3-Hx—Hx-4 | 11.0% |
| 3-Hx—Hx-5 | 5.0% |
| 2-Hx—Hx—Be-1 | 2.0% |
| 3-Hx—Hx—Be-1 | 10.0% |
| 3-Hx—Hx—Be-3 | 15.0% |
| 3-Hx—Be(F)—Tr—Be-2 | 5.0% |
| 3-Hx—Be(F)—Tr—Be-3 | 4.0% |
| 3-Hx—$C_2H_4$—Be—Tr—Be-2 | 4.0% |
| 3-Hx—$C_2H_4$—Be—Tr—Be-3 | 4.0% |
| 3-Hx—$C_2H_4$—Be—Tr—Be-4 | 4.0% |

EXAMPLE 36

| | |
|---|---|
| $CH_2$=CH—Hx—Be—Tr—CN | 15.0% |
| 3-Hx—Be—CN | 20.0% |
| 5-Hx—Be—CN | 31.0% |
| 7-Hx—Be—CN | 21.0% |
| 7-Hx—Be—Be—CN | 13.0% |
| $T_{NI}$ = 75.0 [° C.] | |
| $\eta$ = 23.6 [mPa · s] | |
| $\Delta n$ = 0.155 | |
| $\Delta \epsilon$ = 13.1 | |
| $V_{th}$ = 1.58 [V] | |

EXAMPLE 37

| | |
|---|---|
| 3-Hx—Be(F,F)—Tr—CN | 15.0% |
| 3-Hx—Be—CN | 20.0% |
| 5-Hx—Be—CN | 31.0% |
| 7-Hx—Be—CN | 21.0% |
| 7-Hx—Be—Be—CN | 13.0% |
| $T_{NI}$ = 66.0 [° C.] | |
| $\eta$ = 26.4 [mPa · s] | |
| $\Delta n$ = 0.145 | |
| $\Delta \epsilon$ = 15.2 | |
| $V_{th}$ = 1.44 [V] | |

EXAMPLE 38

| | |
|---|---|
| $CH_2$=CH—Hx—Be—Tr—CN | 5.0% |
| $CH_3CH$=$CHC_2H_4$—Be—COO—Be(F,F)—CN | 5.0% |
| 3-Hx—Be—CN | 20.0% |
| 1-Be—Tr—Be-3 | 5.0% |
| 2-Be—Tr—Be-1 | 10.0% |
| 3-Hx—Hx-4 | 11.0% |
| 3-Hx—Hx—Be-1 | 11.0% |
| 3-Hx—Hx—Be-3 | 9.0% |
| 8-Hx—$C_2H_4$—Be—Tr—Be-2 | 4.0% |
| 3-Hx—$C_2H_4$—Be—Tr—Be-3 | 4.0% |
| 3-Hx—$C_2H_4$—Be—Tr—Be-4 | 4.0% |
| 3-Hx—Be(F)—Tr—Be-2 | 6.0% |
| 3-Hx—Be(F)—Tr—Be-3 | 6.0% |
| $T_{NI}$ = 94.8 [° C.] | |
| $\eta$ = 14.0 [mPa · s] | |
| $\Delta n$ = 0.166 | |
| $\Delta \epsilon$ = 7.2 | |
| $V_{th}$ = 2.13 [V] | |

0.8 part of CM33 was added as a chiral dopant to 100 parts of the above composition to provide 11.2 μm of a twist pitch.

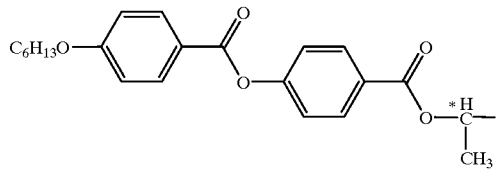

(C-4)

CM33:

| | |
|---|---|
| $CH_2$=CH—Hx—Be—Tr—CN | 7.0% |
| 5-Py—Be—F | 4.0% |
| 3-Py—Be(F)—F | 4.0% |
| 2-Be—Be—CN | 5.0% |
| 4-Be—Be—CN | 4.0% |
| 2-Py—Be-2 | 2.0% |
| 3-Py—Be-2 | 2.0% |
| 4-Py—Be-2 | 2.0% |
| 6-Py—Be—$OC_5H_{11}$ | 3.0% |
| 6-Py—Be—$OC_6H_{13}$ | 3.0% |
| 6-Py—Be—$OC_7H_{15}$ | 3.0% |
| 6-Py—Be—$OC_8H_{17}$ | 3.0% |
| 3-Py—Be—Be—F | 6.0% |
| 4-Py—Be—Be—F | 6.0% |
| 5-Py—Be—Be—F | 6.0% |
| 3-Hx—Hx—Be-1 | 6.0% |
| 3-Hx—Hx—Be-3 | 6.0% |
| 2-Hx—$C_2H_4$—Be—Tr—Be-2 | 4.0% |
| 2-Hx—$C_2H_4$—Be—Tr—Be-3 | 4.0% |
| 2-Hx—$C_2H_4$—Be—Tr—Be-4 | 5.0% |
| 3-Hx—$C_2H_4$—Be—Tr—Be-2 | 5.0% |

-continued

| | |
|---|---|
| 3-Hx—$C_2H_4$—Be—Tr—Be-3 | 5.0% |
| 3-Hx—$C_2H_4$—Be—Tr—Be-4 | 5.0% |
| $T_{NI}$ = 97.7 [° C.] | |
| $\eta$ = 33.1 [mPa · s] | |
| $\Delta n$ = 0.206 | |
| $\Delta \epsilon$ = 6.6 | |
| $V_{th}$ = 2.24 [V] | |

EXAMPLE 40

| | |
|---|---|
| $CH_2$=CH—Hx—Be—Tr—CN | 7.0% |
| $C_2H_5OCH_2$—Be—COO—Be(F)—CN | 5.0% |
| $C_3H_7OCH_2$—Be—COO—Be(F)—CN | 12.0% |
| $C_5H_{11}OCH_2$—Be—COO—Be(F)—CN | 4.0% |
| $CH_3CH$=$CHC_2H_4$—Be—COO—Be(F,F)—CN | 14.0% |
| 3-Hx—Be—$OC_2H_5$ | 10.0% |
| 3-Hx—Hx-4 | 3.0% |
| 3-Hx—Hx—Be—F | 3.0% |
| 3-Hx—Hx—Be-1 | 3.0% |
| 3-Hx—Hx—Be—$OCH_3$ | 4.0% |
| 3-Hx—Be—COO—Be—F | 4.0% |
| 3-Hx—Hx—COO—Be—F | 7.0% |
| 5-Hx—Hx—COO—Be—F | 7.0% |
| 3-Hx—$C_2H_4$—Be—Tr—Be-2 | 4.0% |
| 3-Hx—$C_2H_4$—Be—Tr—Be-3 | 4.0% |
| 3-Hx—$C_2H_4$—Be—Tr—Be-4 | 4.0% |
| 3-Hx—Be(F)—Tr—Be-2 | 5.0% |
| $T_{NI}$ = 88.9 [° C.] | |
| $\eta$ = 38.9 [mPa · s] | |
| $\Delta n$ = 0.150 | |
| $\Delta \epsilon$ = 28.1 | |
| $V_{th}$ = 1.01 [V] | |

EXAMPLE 41

| | |
|---|---|
| $CH_2$=CH—Hx—Be—Tr—CN | 7.0% |
| 2-Hx—Be—CN | 5.0% |
| 3-Hx—Be—CN | 12.0% |
| 3-Hx—Be—$OC_2H_5$ | 12.0% |
| 2-Be—Tr—Be-1 | 3.0% |
| 3-Hx—Hx—Be-1 | 8.0% |
| 3-Hx—Hx—Be—F | 4.0% |
| 3-Hx—Hx—Be—$OCH_3$ | 5.0% |
| 3-Hx—Hx—Be-3 | 10.0% |
| 3-Hx—Hx—COO—Be—F | 4.0% |
| 5-Hx—Hx—COO—Be—F | 4.0% |
| 2-Hx—Hx—Be(F)—F | 7.0% |
| 3-Hx—Hx—Be(F)—F | 7.0% |
| 5-Hx—Hx—Be(F)—F | 7.0% |
| 3-Hx—Hx—Be(F,F)—F | 5.0% |
| $T_{NI}$ = 100.9 [° C.] | |
| $\eta$ = 18.1 [mPa · s] | |
| $\Delta n$ = 0.110 | |
| $\Delta \epsilon$ = 6.0 | |
| $V_{th}$ = 2.15 [V] | |

EXAMPLE 42

| | |
|---|---|
| $CH_2$=CH—Hx—Be—Tr—CN | 5.0% |
| 3-Hx—Be(F,F)—Tr—CN | 5.0% |
| 3-Be—COO—Be(F)—CN | 8.0% |
| 3-Hx—Be—CN | 8.0% |
| $CH_2$=CH—Hx—Be—CN | 8.0% |
| $CH_3CH$=CH—Hx—Be—CN | 3.0% |
| 3-Hx—Be—$OC_2H_5$ | 3.0% |
| 3-Hx—Hx—$C_2H_4CH$=$CH_2$ | 14.0% |
| 3-Hx—Hx—$C_2H_4CH$=$CHCH_3$ | 7.0% |
| $CH_2$=$CHC_2H_4$—Hx—Hx—Be-1 | 10.0% |
| 3-Hx—Hx—Be-1 | 5.0% |

-continued

| | |
|---|---|
| 3-Hx—Hx—COO—Be—F | 7.0% |
| 3-Hx—C₂H₄—Be—Tr—Be-2 | 6.0% |
| 3-Hx—C₂H₄—Be—Tr—Be-3 | 6.0% |
| 3-Hx—C₂H₄—Be—Tr—Be-4 | 5.0% |
| $T_{NI}$ = 96.2 [° C.] | |
| η = 14.9 [mPa · s] | |
| Δn = 0.141 | |
| Δε = 10.7 | |
| $V_{th}$ = 98 [V] | |

EXAMPLE 43

| | |
|---|---|
| 3-Hx—Be(F,F)—Tr—CN | 5.0% |
| C₂H₅OCH₂—Be—COO—Be(F)—CN | 5.0% |
| C₃H₇OCH₂—Be—COO—Be(F)—CN | 5.0% |
| C₄H₉OCH₂—Be—COO—Be(F)—CN | 5.0% |
| C₅H₁₁OCH₂—Be—COO—Be(F)—CN | 5.0% |
| 2-Hx—Hx—Be(F)—C | 15.0% |
| 3-Hx—Hx—Be(F)—C | 15.0% |
| 3-Hx—Be(F)—Tr—Be-2 | 4.0% |
| 3-Hx—Be(F)—Tr—Be-3 | 4.0% |
| 3-Hx—Be(F)—Tr—Be-4 | 4.0% |
| 3-Hx—Hx—Be-1 | 8.0% |
| 3-Hx—Hx—Be—OCH₃ | 4.0% |
| $T_{NI}$ = 79.8 [° C.] | |
| η = 82.9 [mPa · s] | |
| Δn = 0.166 | |
| Δε = 32.0 | |
| $V_{th}$ = 0.84 [V] | |

EXAMPLE 44

| | |
|---|---|
| 3-Hx—Be(F,F)—Tr—CN | 7.0% |
| C₂H₅OCH₂—Be—COO—Be(F)—CN | 5.0% |
| C₃H₇OCH₂—Be—COO—Be(F)—CN | 12.0% |
| C₅H₁₁OCH₂—Be—COO—Be(F)—CN | 4.0% |
| CH₃CH=CHC₂H₄—Be—COO—Be(F,F)—CN | 10.0% |
| 3-Hx—Hx—COOCH₃ | 10.0% |
| 3-Hx—Be—OC₂H₅ | 16.0% |
| 7-Hx—COO—Be—F | 2.0% |
| 3-Hx—Hx—COO—Be—F | 2.0% |
| 5-Hx—Hx—COO—Be—F | 2.0% |
| 3-Hx—Hx—Be—COO—Be—F | 4.0% |
| C₂H₅OCH₂—Hx—Be—COO—Be(F)—CN | 2.0% |
| 3-Hx—Be(F)—COO—Be(F)—CN | 2.0% |
| 3-Hx—Be—COO—Be(F,F)—CN | 2.0% |
| 3-Hx—Hx—Be—F | 4.0% |
| 3-Hx—Hx—Be—OCH₃ | 4.0% |
| 3-Hx—Hx—Be-3 | 8.0% |
| 3-Hx—COO—Be—COO—Be—F | 2.0% |
| 3-Hx—COO—Be—COO—Be-1 | 2.0% |
| $T_{NI}$ = 70.1 [° C.] | |
| η = 36.0 [mPa · s] | |
| Δn = 0.121 | |
| Δε = 25.9 | |
| $V_{th}$ = 0.95 [V] | |

EXAMPLE 45

| | |
|---|---|
| CH₂=CH—Hx—Be—Tr—CN | 6.0% |
| 2-Hx—Hx—Be(F)—F | 2.0% |
| 3-Hx—Hx—Be(F)—F | 2.0% |
| 5-Hx—Hx—Be(F)—F | 2.0% |
| 2-Hx—Be—Be(F)—F | 6.0% |
| 3-Hx—Be—Be(F)—F | 6.0% |
| 5-Hx—Be—Be(F)—F | 4.0% |
| 2-Hx—C₂H₄—Be—Be(F)—F | 9.0% |
| 3-Hx—C₂H₄—Be—Be(F)—F | 9.0% |
| 3-Hx—Be—Be(F,F)—F | 25.0% |
| 5-Hx—Be—Be(F,F)—F | 19.0% |
| CH₃OCH₂—Hx—Be—Be—Hx-4 | 5.0% |
| CH₃OCH₂—Hx—Be—Be—Hx-4 | 5.0% |
| $T_{NI}$ = 97.3 [° C.] | |
| η = 34.1 [mPa · s] | |
| Δn = 0.141 | |
| Δε = 8.1 | |
| $V_{th}$ = 1.85 [V] | |

EXAMPLE 46

| | |
|---|---|
| CH₂=CH—Hx—Be—Tr—CN | 6.0% |
| 3-Hx—Be(F,F)—Tr—CN | 6.0% |
| 3-Hx—C₂H₄—Hx—Be(F,F)—F | 7.0% |
| 5-Hx—C₂H₄—Hx—Be(F,F)—F | 8.0% |
| 3-Hx—Hx—Be(F,F)—F | 10.0% |
| 4-Hx—Hx—Be(F,F)—F | 5.0% |
| 3-Hx—Hx—C₂H₄—Be(F,F)—F | 3.0% |
| 5-Hx—Hx—C₂H₄—Be(F,F)—F | 3.0% |
| 3-Hx—Be—Be(F,F)—F | 15.0% |
| 5-Hx—Be—Be(F,F)—F | 15.0% |
| 3-Hx—Be—COO—Be(F,F)—F | 2.0% |
| 4-Hx—Be—COO—Be(F,F)—F | 2.0% |
| 5-Hx—Be—COO—Be(F,F)—F | 2.0% |
| 3-Hx—Hx—COO—Be(F,F)—F | 10.0% |
| 4-Hx—Hx—COO—Be(F,F)—F | 3.0% |
| 5-Hx—Hx—COO—Be(F,F)—F | 3.0% |
| $T_{NI}$ = 79.0 [° C.] | |
| η = 29.5 [mPa · s] | |
| Δn = 0.110 | |
| Δε = 13.7 | |
| $V_{th}$ = 1.57 [V] | |

EXAMPLE 47

| | |
|---|---|
| CH₂=CH—Hx—Be—Tr—CN | 10.0% |
| 3-Hx—Be(F)—Tr—CN | 5.0% |
| 3-Hx—Be(F,F)—Tr—CN | 2.0% |
| CH₃CH=CHC₂H₄—Be—COO—Be(F,F)—CN | 6.0% |
| 3-Hx—Be—OC₂H₅ | 4.0% |
| 3-Hx—Hx—CH=CF₂ | 18.0% |
| 5-Hx—Hx—CH=CF₂ | 20.0% |
| CF₂=CH—Hx—Hx—Be-1 | 8.0% |
| CF₂=CHC₂H₄—Hx—Hx—Be-1 | 10.0% |
| 3-Hx—C₂H₄—Be—Tr—Be-2 | 4.0% |
| 3-Hx—C₂H₄—Be—Tr—Be-3 | 4.0% |
| 3-Hx—C₂H₄—Be—Tr—Be-4 | 4.0% |
| 3-Hx—Be(F)—Tr—Be-2 | 5.0% |
| $T_{NI}$ = 100.4 [° C.] | |
| η = 11.2 [mPa · s] | |
| Δn = 0.136 | |
| Δε = 7.9 | |
| $V_{th}$ = 2.14 [V] | |

EXAMPLE 48

| | |
|---|---|
| CH₂=CH—Hx—Be—Tr—CN | 2.0% |
| 3-Hx—Be(F)—Tr—CN | 11.0% |
| 3-Hx—Be(F,F)—Tr—CN | 2.0% |
| CH₃CH=CHC₂H₄—Be—COO—Be(F,F)—CN | 6.0% |
| CH₂=CHC₂H₄—Hx—Hx—CH=CF₂ | 35.0% |
| 5-Hx—Hx—CH=CF₂ | 3.0% |
| CF₂=CH—Hx—Hx—Be-1 | 8.0% |
| CF₂=CHC₂H₄—Hx—Hx—Be-1 | 18.0% |
| 3-Hx—C₂H₄—Be—Tr—Be-2 | 4.0% |
| 3-Hx—C₂H₄—Be—Tr—Be-3 | 4.0% |
| 3-Hx—C₂H₄—Be—Tr—Be-4 | 4.0% |
| 3-Hx—Be(F)—Tr—Be-2 | 3.0% |
| $T_{NI}$ = 100.7 [° C.] | |

$\eta = 10.7$ [mPa · s]
$\Delta n = 0.132$
$\Delta \epsilon = 8.1$
$V_{th} = 2.09$ [V]

EXAMPLE 49

Comparative tests on the characteristics were made with regard to the following compositions 1 and 2 each containing different first ingredients. Each compound constituting the composition is designated by the foregoing abbreviations.

| Ingredients | Composition 1 | Composition 2 |
| --- | --- | --- |
| 3-Hx—Be—Tr—CN | 15 wt % | — |
| 3-Hx—Be(F)—Tr—CN (Compound No. 2) | — | 15 wt % |
| 3-Hx—Be—CN | 20 wt % | 20 wt % |
| 5-Hx—Be—CN | 31 wt % | 31 wt % |
| 7-Hx—Be—CN | 21 wt % | 21 wt % |
| 5-Hx—Be—Be—CN | 13 wt % | 13 wt % |

The characteristics as determined are shown in the following table.

| Characteristics | Composition 1 | Composition 2 |
| --- | --- | --- |
| $T_{NI}$ [° C.] | 76.8 | 72.7 |
| $\eta$ [mPa · s] | 26.5 | 23.0 |
| $\Delta n$ [—] | 0.150 | 0.150 |
| $\Delta \epsilon$ [—] | 12.0 | 13.5 |
| Vth [v] | 1.63 | 1.43 |

What is claimed is:

1. A propiolonitrile derivative of formula (I)

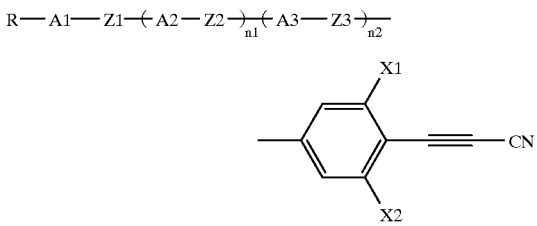

(1)

wherein n1 and n2 each independently stand for 0 or 1; A1, A2 and A3 each independently represent a 1,4-phenylene, a 1,4-phenylene substituted by one or more fluorine atoms, a trans-1,4-cyclohexylene, a 1,3-dioxane-2,5-diyl or a 1,3-pyrimidine-2,5-diyl; Z1, Z2 and Z3 each independently represent a single bond, ethylene, ethenylene, ethynylene, carbonyloxy, oxycarbonyl, methyleneoxy, oxymethylene, 1,4-butylene or 1,4-butenylene; R represents a saturated, aliphatic hydrocarbyl radical of 1–10 carbons, an unsaturated, aliphatic hydrocarbyl radical of 2–10 carbons, a saturated or unsaturated, aliphatic hydrocarbyl radical of 1–10 carbons containing one or more ether linkages (—O—) in the chain and a saturated or unsaturated, fluoro-substituted aliphatic hydrocarbyl radical of 1–10 carbons containing one or more fluorine atoms in the chain; X1 and X2 each independently represent H, F or Cl;

provided that at least one of X1 and X2 is F or Cl, when both n1 and n2 are 0 or when n1 is 0 and n2 is 1, Z1 represents a single bond, ethylene, carbonyloxy or oxycarbonyl and R represents alkyl or alkoxy; or when n1 is 1, n2 is 1 or 0, Z1 and Z2 each independently represent a single bond or ethylene, Z3 represents ethylene and R represents alkyl or alkoxy.

2. The derivative of claim 1 wherein n1 and n2 are 0.

3. The derivative of claim 1 wherein n1 is 1 and n2 is 0.

4. The derivative of claim 1 wherein n1 and n2 are 1.

5. The derivative of claim 1 wherein R is alkenyl of 2–10 carbons.

6. The derivative of claim 1 wherein R is alkenyl of 2–10 carbons, both X1 and X2 are hydrogen.

7. The derivative of claim 1 wherein n1 and n2 are 0 and R is alkenyl of 2–10 carbons.

8. The derivative of claim 1 wherein n1 is 1, n2 is 0 and R is alkenyl of 2–10 carbons.

9. The derivative of claim 1 wherein n1 and n2 are 0, Z1 is a single bond and R is alkenyl of 2–10 carbons.

10. The derivative of claim 1 wherein n1 is 1, n2 is 0, Z1 is a single bond and R is alkenyl of 2–10 carbons.

11. The derivative of claim 1 wherein one or both of X1 and X2 represent F or Cl and R is alkyl of 1–10 carbons.

12. The derivative of claim 1 wherein one of Z1, Z2 and Z3 is ethylene, 1,4-butylene, oxymethylene or methyleneoxy, and the other is a single bond or ethylene.

13. The derivative of claim 1 wherein n1 and n2 are 0 and Z1 is ethylene, 1,4-butylene, oxyethylene or methyleneoxy.

14. The derivative of claim 1 wherein n1 is 1, n2 is 0 and one of Z1 and Z2 is ethylene, 1,4-butylene, oxymethylene or methyleneoxy, and the other is a single bond or ethylene.

15. The derivative of claim 1 wherein n1 and n2 are 1, and one of Z1, Z2 and Z3 is ethenylene, 1,4-butenylene or ethynylene, and the other is a single bond or ethylene.

16. The derivative of claim 1 wherein n1 and n2 are 0, and Z1 is ethenylene, 1,4-butenylene or ethynylene.

17. The derivative of claim 1 wherein n1 is 1, n2 is 0 and one of Z1 and Z2 is ethenylene, 1,4-butenylene or ethynylene, and the other is a single bond or ethylene.

18. The derivative of claim 1 wherein n1 and n2 are 1, one of Z1, Z2 and Z3 is carbonyloxy or hydroxycarbonyl, and the other is a single bond or ethylene.

19. The derivative of claim 1 wherein n1 and n2 are 1, one of Z1, Z2 and Z3 is carbonyloxy or oxycarbonyl, and the other is a single bond or ethylene and one or both of X1 and X2 represent F.

20. The derivative of claim 1 wherein n1 and n2 are 0 and Z1 is carbonyloxy or hydroxycarbonyl.

21. The derivative of claim 1 wherein n1 and n2 are 0 and Z1 is carbonyloxy or hydroxycarbonyl, and one or both of X1 and X2 represent F.

22. The derivative of claim 1 wherein n1 is 1, n2 is 0 and one of Z1 and Z2 is carbonyloxy or oxycarbonyl, and the other is a single bond or ethylene.

23. The derivative of claim 1 wherein n1 is 1, n2 is 0, one of Z1 and Z2 is carbonyloxy or oxycarbonyl, and the other is a single bond or ethylene and one or both of X1 and X2 represent F.

24. The derivative of claim 1 wherein n1 and n2 are 0, and A1 is 1,4-cyclohexylene.

25. The derivative of claim 1 wherein n1 and n2 are 0, and A1 is 1,4-phenylene which may be substituted by one or more fluorine atoms.

26. The derivative of claim 1 wherein n1 is 1, n2 is 0 and one or both of A1 and A2 represent trans-1,4-cyclohexylene.

27. The derivative of claim 1 wherein n1 is 1, n2 is 0 and one or both of A1 and A2 represent 1,4-phenylene.

28. A liquid crystal composition comprising at least two ingredients containing at least one of the propiolonitrile derivatives of claim 1.

29. A liquid crystal composition comprising as a first ingredient, at least one of the propiolonitrile derivatives of claim 1 and as a second ingredient, at least one of a compound of formula (2)

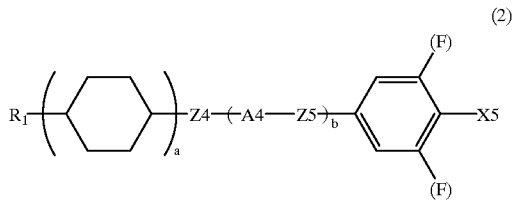
(2)

wherein a is 1 or 2; b is 0 or 1; A4 represents a trans-1,4-cyclohexylene or a 1,4-phenylene which may be substituted by one or more fluorine atoms; Z4 and Z5 each independently represent a single bond, ethylene or ethenylene; $R_1$ respresents an alkyl group of 1–10 carbons and X5 represents F, $CF_3$, $OCF_3$, $OCF_2H$ or Cl; and (F) stands for the case which the phenyl ring may be substituted by F.

30. A liquid crystal composition comprising as a first ingredient, at least one of the propiolonitrile derivatives of claim 1 and as a second ingredient, at least one of a compound of formula (3)

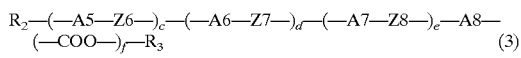
(3)

wherein c, d, e and f each independently stand for 0 or 1; A5, A6 and A7 each independently represent a trans-1,4-cyclohexylene, a 1,4-phenylene which may be substituted by one or more fluorine atoms, a trans-1,4-cyclohexylene, a 1,3-dioxane-2,5-diyl and a 1,3-pyrimidine-2,5-diyl; A8 represents a trans-1,4-cyclohexylene or 1,4-phenylene which may be substituted by one or two fluorine atoms; Z6, Z7 and Z8 each independently represent a single bond, ethylene, ethenylene, ethynylene, 1-butene-3-ynylene or carbonyloxy; $R_2$ represents a saturated or unsaturated aliphatic hydrocarbyl radical of 1–10 carbons optionally having one or more ether linkages (—O—) in the chain and $R_3$ represents —CN, —F, —$OCF_3$, —$OCF_2H$, —$CF_3$, —$CF_2H$, —$CFH_2$ or a saturated or unsaturated aliphatic hydrocarbyl radical of 1 to 10 carbons optionally containing one or more ether linkages (—O—) in the chain.

31. A liquid crystal display element composed of the liquid crystal composition as defined in any one of claims 28–30.

32. The liquid crystal composition of claim 30, further comprising at least one compound of a formula (2)

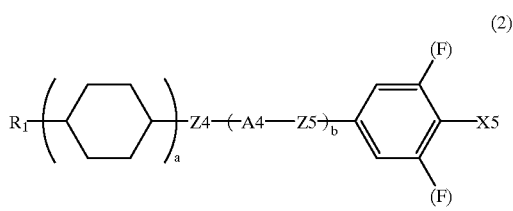
(2)

wherein a is 1 or 2; b is 0 or 1; A4 represents a trans-1,4-cyclohexylene or a 1,4-phenylene which may be substituted by one or more fluorine atoms; Z4 and Z5 each independently represent a single bond, ethylene or ethenylene; $R_1$, represents an alkyl group of 1–10 carbons and X5 represents F, $CF_3$, $OCF_3$, $OCF_2H$ or Cl; and (F) stands for the case in which the phenyl ring may be substituted by F.

33. A liquid crystal display element composed of the liquid crystal composition as defined in claim 32.

\* \* \* \* \*

UNITED STATES PATENT AND TRADEMARK OFFICE
CERTIFICATE OF CORRECTION

PATENT NO. : 6,017,467
DATED : January 25, 2000
INVENTOR(S) : Atsuko FUJITA, ET AL.

It is certified that error appears in the above-identified patent and that said Letters Patent is hereby corrected as shown below:

Column 134, line 28 "$R_{,,}$" should be --$R_1$--.

Signed and Sealed this

Twenty-second Day of May, 2001

*Attest:*

NICHOLAS P. GODICI

*Attesting Officer*     *Acting Director of the United States Patent and Trademark Office*